(12) United States Patent
Ohkubo et al.

(10) Patent No.: US 6,380,215 B1
(45) Date of Patent: Apr. 30, 2002

(54) BETA-ALANINE DERIVATIVE AND A PROCESS FOR THE PREPARATION THEREOF

(75) Inventors: Mitsuru Ohkubo, Kawabe-gun; Fumie Takahashi, Higashiosaka; Toshio Yamanaka, Osaka; Hiroyoshi Sakai, Uji; Masayuki Kato, Kyoto, all of (JP)

(73) Assignee: Fujisawa Pharmaceutical Co., Ltd, Osaka (JP)

( * ) Notice: Subject to any disclaimer, the term of this patent is extended or adjusted under 35 U.S.C. 154(b) by 0 days.

(21) Appl. No.: 08/495,572

(22) PCT Filed: Sep. 21, 1994

(86) PCT No.: PCT/JP97/01550

§ 371 Date: Aug. 4, 1995

§ 102(e) Date: Aug. 4, 1995

(87) PCT Pub. No.: WO95/08536

PCT Pub. Date: Mar. 30, 1995

(30) Foreign Application Priority Data

Sep. 22, 1993 (GB) ................................ 9319561
Jul. 11, 1994 (GB) ................................ 9413936

(51) Int. Cl.$^7$ .................... A61K 31/4545; C07D 401/06
(52) U.S. Cl. .................. 514/316; 546/189; 546/188; 546/190; 546/208; 544/180; 544/224
(58) Field of Search ................. 514/316, 326; 546/188, 189, 190, 193, 198, 199, 200, 201, 208, 209, 210, 211, 261, 262, 263, 264, 265, 267; 544/224, 180

(56) References Cited

U.S. PATENT DOCUMENTS 5,770,575 A * 6/1998 Beavers et al. ............... 514/19

FOREIGN PATENT DOCUMENTS

| CA | 2037153 | * | 9/1991 |
| EP | 498941 | * | 8/1992 |
| WO | WO 95/25091 | * | 9/1995 |

* cited by examiner

Primary Examiner—Charanjit S. Aulakh
(74) Attorney, Agent, or Firm—Oblon, Spivak, McClelland, Maier & Neustadt, P.C.

(57) ABSTRACT

This invention relates to β-alanine derivatives represented by the following formula:

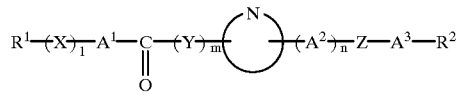

wherein each symbol is as defined in the specification and pharmaceutically acceptable salt thereof which is glycoprotein IIb/IIIa antagonist, inhibitor of blood platelets aggregation and inhibitor of the binding of fibrinogen to blood platelets, to processes for the preparation thereof, to a pharmaceutical composition comprising the same and to a method for the prevention and/or treatment diseases indicated in the specification to a human being or an animal.

12 Claims, No Drawings

BETA-ALANINE DERIVATIVE AND A PROCESS FOR THE PREPARATION THEREOF

TECHNICAL FIELD

The present invention relates to β-alanine derivative and a pharmaceutically acceptable salt thereof. More particularly, it relates to β-alanine derivative and a salt thereof which is glycoprotein IIb/IIIa antagonist, inhibitor of blood platelets aggregation and inhibitor of the binding of fibrinogen to blood platelets.

BACKGROUND ART

In European Patent Application No. 512,831 A1, there are disclosed fibrinogen receptor antagonists.

In European Patent Application No. 445,796 A2, there are disclosed inhibitor of blood platelets aggregation.

DISCLOSURE OF INVENTION

The present invention relates to β-alanine derivative and a salt thereof. More particularly, it relates to β-alanine derivative and a salt thereof which is glycoprotein IIb/IIIa antagonist and inhibitor of platelet aggregation, and useful as:

- a drug for the prevention and/or the treatment of diseases caused by thrombus formation such as arterial thrombosis; arterial sclerosis; ischemic heart diseases [e.g. angina pectoris (e.g. stable angina pectoris, unstable angina pectoris including imminent infarction, etc.), myocardial infarction (e.g. acute myocardial infarction, etc.), coronary thrombosis, etc.]; ischemic brain diseases [e.g. cerebral infarction {e.g. cerebral thrombosis (e.g. acute cerebral thrombosis, etc.), cerebral embolism, etc.}, transient cerebral ischemia (e.g. transient ischemic attack, etc.), cerebrovascular spasm after cerebral hemorrhage (e.g. cerebrovascular spasm after subarachnoid hemorrhage, etc.), etc.]; pulmonary vascular diseases (e.g. pulmonary thrombosis, pulmonary embolism etc.); peripheral circulatory disorder [e.g. arteriosclerosis obliterans, thromboangiitis obliterans (i.e. Bürger's disease), Raynaud's disease, complication of diabetes mellitus (e.g. diabetic angiopathy, diabetic neuropathy, etc.), phlebothrombosis (e.g. deep vein thrombosis, etc.), etc.] or the like;
- a drug for the prevention and/or the treatment of restenosis and/or reocclusion such as restenosis and/or reocclusion after percutaneous transluminal coronary angioplasty (PTCA), restenosis and/or reocclusion after the administration of thrombolytic drug (e.g. tissue plasminogen activator (TPA), etc.) or the like;
- a drug for the adjuvant therapy with thrombolytic drug (e.g. TPA, etc.) or anticoagulant (e.g. heparin, etc.);
- a drug for the prevention and/or the treatment of the thrombus formation in case of vascular surgery, valve replacement, extracorporeal circulation [e.g. surgery (e.g. open heart surgery, pump-oxygenator, etc.) hemodialysis, etc.], transplantation, or the like;
- a drug for the prevention and/or the treatment of disseminated intravascular coagulation (DIC), thrombotic thrombocytopenia, essential thrombocytosis, inflammation (e.g. nephritis, etc.), immune diseases, or the like;
- a drug for inhibiting of metastasis; or the like.

The β-alanine derivative of the present invention is expected to be useful as an inhibitor of cell adhesion and so is expected to be useful as

- a drug for the prevention and/or the treatment of disseminated intravascular coagulation (DIC), thrombotic thrombocytopenia, essential thrombocytosis, inflammation (e.g. nephritis, etc.), immune diseases, or the like;
- a drug for inhibiting of metastasis; or the like.

Accordingly, one object of the present invention is to provide β-alanine derivative or a salt thereof which is useful as stated above.

Another object of the present invention is to provide processes for preparation of said β-alanine derivative or a salt thereof.

A further object of the present invention is to provide a pharmaceutical composition comprising, as an active ingredient, said β-alanine derivative or a salt thereof.

Still further object of this invention is to provide methods of using said β-alanine derivative or a salt thereof for the prevention and/or the treatment of aforesaid diseases in a human being or an animal.

The object β-alanine derivative of the present invention can be shown by the following formula (I):

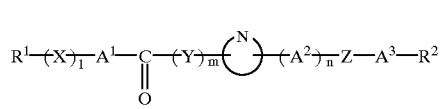

wherein
- $R^1$ is N-containing cycloalkyl which may have one or more suitable substituent(s),
- $R^2$ is carboxy or protected carboxy,
- $A^1$ is lower alkylene, lower alkanyl-ylidene or lower alkenylene, each of which may have one or more suitable substituent(s),
- $A^2$ is lower alkylene,
- $A^3$ is lower alkylene which may have one or more suitable substituent(s),

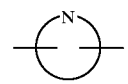

is a group of the formula:

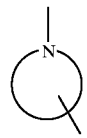

(wherein

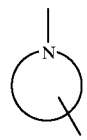

is N-containing heterocyclic group which may have one or more suitable substituent(s)),
- X is O, S or NH,
- Y is NH, Z is

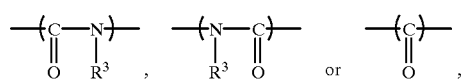

(wherein R³ is hydrogen or lower alkyl), l, m and n are each the same or different an integer of 0 or 1, or a pharmaceutically acceptable salt thereof.

The object compound (I) or a salt thereof can be prepared by the following processes.

Process 1

(II)
or its reactive derivative
at the carboxy group
or a salt thereof (III)
or its reactive derivative
at the amino group
or a salt thereof

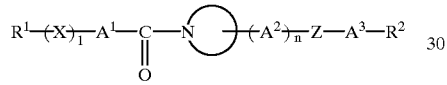

(Ia)
or a salt thereof

Process 2

(IV)
or its reactive derivative
at the carboxy group
or a salt thereof

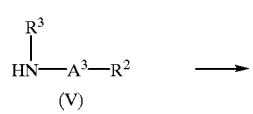

(V)
or its reactive derivative
at the amino group
or a salt thereof

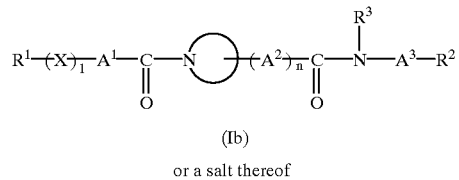

(Ib)
or a salt thereof

Process 3

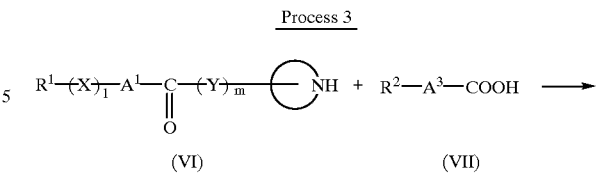

(VI)
or its reactive derivative
at the amino group
or a salt thereof (VII)
or its reactive derivative
at the carboxy group
or a salt thereof

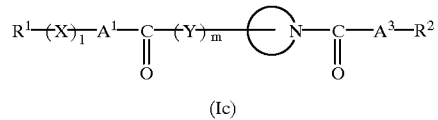

(Ic)
or a salt thereof

Process 4

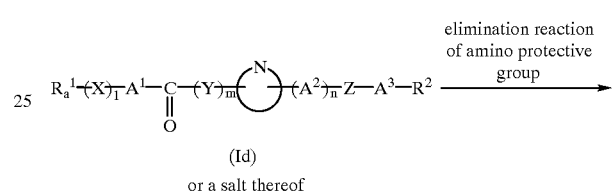

elimination reaction
of amino protective
group (Id)
or a salt thereof

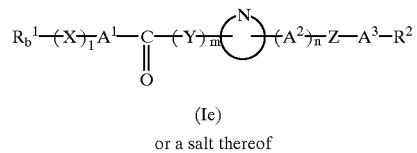

(Ie)
or a salt thereof

Process 5

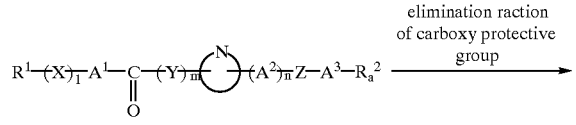

elimination reaction
of carboxy protective
group (If)
or a salt thereof

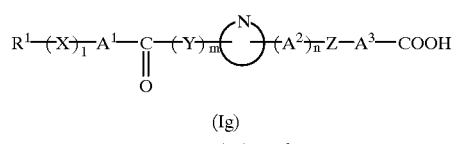

(Ig)
or a salt thereof

Process 6

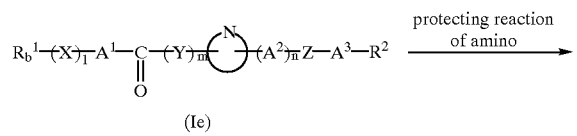

protecting reaction
of amino (Ie)
or its reactive derivative
at the amino group
or a salt thereof

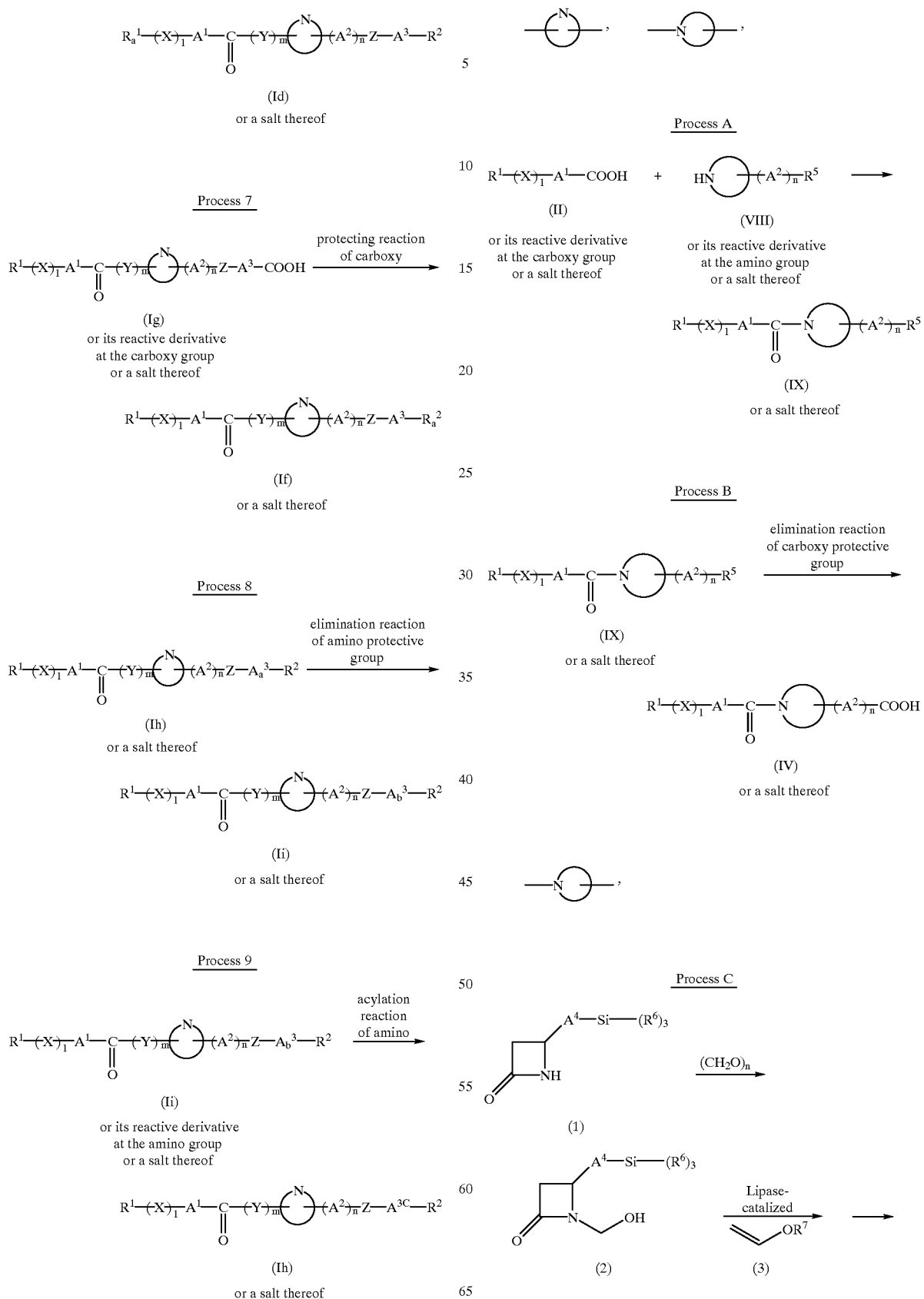

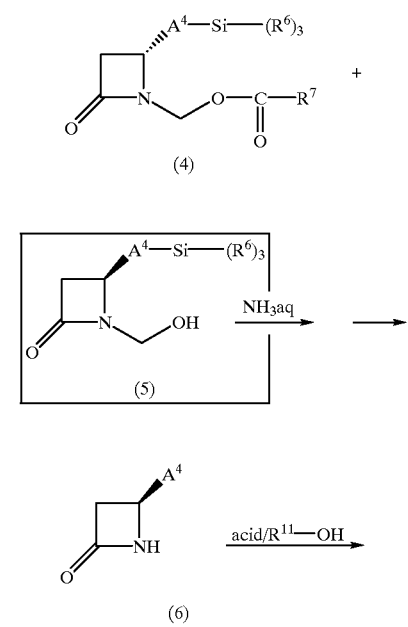

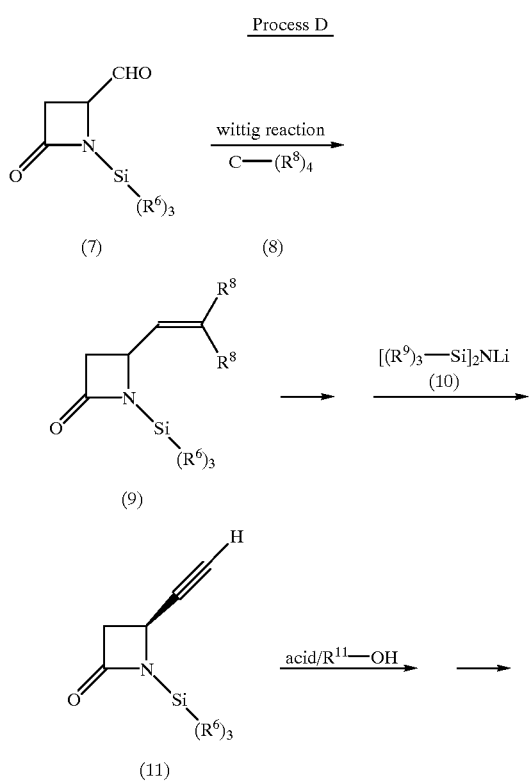

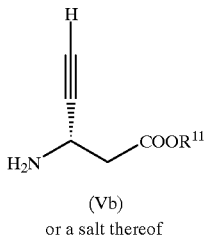

(Vb)
or a salt thereof wherein $A^4$ is lower alkynylene,

Three $R^6$ are independently lower alkyl, $R^7$ is lower alkyl,

Two $R^8$ are independently halogen,

Three $R^9$ are independently lower alkyl, and $R^{11}$ is lower alkyl.

Among the starting compounds (II), (III), (IV), (V), (VI), (VII), (VIII), and (IX), there are novel compounds. They can be prepared from the known compounds in a conventional manner in this field of the art or the similar manners to those disclosed in Preparations and/or Examples mentioned later in the present specification.

Suitable pharmaceutically acceptable salts of the object compound (I) are conventional non-toxic salts and include a metal salt such as an alkali metal salt [e.g. sodium salt, potassium salt, etc.] and an alkaline earth metal salt [e.g. calcium salt, magnesium salt, etc.] an ammonium salt, an organic base salt [e.g. trimethylamine salt, triethylamine salt, pyridine salt, picoline salt dicyclohexylamine salt, N,N-dibenzylethylenediamine salt, etc.], an organic acid addition salt [e.g. formate, acetate, trifluoroacetate, maleate, tartrate, methanesulfonate, benzenesulfonate, toluenesulfonate, etc.], an inorganic acid addition salt [e.g. hydrochloride, hydrobromide, hydroiodide, sulfate, phosphate, etc.], a salt with an amino acid [e.g. arginine salt, aspartic acid salt, glutamic acid salt, etc.] and the like.

In the above and subsequent descriptions of this specification, suitable examples of the various definitions are explained in detail as follows:

The term "lower" is intended to mean 1 to 6 carbon atom(s), unless otherwise indicated.

The term "higher" is used to intend a group having 7 to 20 carbon atoms, unless otherwise provided.

The preferable number of the "one or more" in the term "one or more suitable substituent(s)" may be 1 to 4.

Suitable "lower alkyl" may be straight or branched ones such as methyl, ethyl, isopropyl, propyl, butyl, isobutyl, sec-butyl, t-butyl, pentyl, hexyl or the like.

Suitable "protected carboxy" may be a conventional protecting group such as an esterified carboxy group, or the like, and concrete examples of the ester moiety in said esterified carboxy group may be the ones such as lower alkyl ester [e.g. methyl ester, ethyl ester, propyl ester, isopropyl ester, butyl ester, isobutyl ester, tert-butyl ester, pentyl ester, hexyl ester, 1-cyclopropylethyl ester, etc.] which may have suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, 1-acetoxyethyl ester, 1-propionyloxyethyl ester, pivaloyloxyethyl ester, 2-propionyloxyethyl ester, hexanoyloxymethyl ester, etc.], lower-alkanesulfonyl(lower)alkyl ester [e.g. 2-mesylethyl ester, etc.] or mono(or di or tri)halo(lower)alkyl ester [e.g. 2-iodoethyl ester, 2,2,2-trichloroethyl ester, etc.];

higher alkyl ester [e.g. heptyl ester, octyl ester, 3,5-dimethyloctyl ester, 3,7-dimethyloctyl ester, nonyl ester, decyl ester, undecyl ester, dodecyl ester, tridecyl ester, tetradecyl ester, pentadecyl ester, hexadecyl ester, heptadecyl ester, octadecyl ester, nonadecyl ester, adamantyl ester, etc.];

lower alkenyl ester [e.g. (C2–C6)alkenyl ester,(e.g. vinyl ester, allyl ester, etc.)];

lower alkynyl ester [e.g. (C2–C6)alkynyl ester (e.g. ethynyl ester, propynyl ester, etc.)];

ar(lower)alkyl ester which may have one or more suitable substituent(s) [e.g. phenyl(lower)alkyl ester which may have 1 to 4 lower alkoxy, halogen, nitro, hydroxy, lower alkyl, phenyl, or halo(lower)alkyl, (e.g. benzyl ester, 4-methoxybenzyl ester, 4-chlorobenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, 4-trifluoromethylbenzyl ester, etc.)];

aryl ester which may have one or more suitable substituent(s) [e.g. phenyl ester which may have 1 to 4 lower alkyl, or halogen, (e.g. phenyl ester, 4-chlorophenyl ester, tolyl ester, 4-tert-butylphenyl ester, xylyl ester, mesityl ester, cumenyl ester, etc.)];

cycloalkyloxycarbonyloxy(lower)alkyl ester which may have lower alkyl (e.g., cyclopentyloxycarbonyloxymethyl ester, cyclohexyloxycarbonyloxymethyl ester, cycloheptyloxycarbonyloxymethyl ester, 1-methylcyclohexyloxycarbonyloxymethyl ester, 1-(or 2-)-[cyclopentyloxycarbonyloxy]ethyl ester, 1-(or 2-)-[cyclohexyloxycarbonyloxy]ethyl ester, 1-(or 2-)-[cycloheptyloxycarbonyloxy]ethyl ester, etc.), etc.];

(5-(lower)alkyl-2-oxo-1,3-dioxol-4-yl)(lower)alkyl ester [e.g., (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)methyl ester, 1-(or 2-)(5-methy-2-oxo-1,3-dioxol-4-yl)ethyl ester, 1-(or 2-)(5-ethyl-2-oxo-1,3-dioxol-4-yl)ethyl ester, 1-(or 2-)(5-propyl-2-oxo-1,3-dioxol-4-yl)ethyl ester, etc.]; or the like, in which the preferred one may be lower alkyl ester, lower alkanoyloxy(lower)alkyl ester, ar(lower)alkyl ester which may have one or more suitable substituent(s), cycloalkyloxycarbonyloxy(lower)alkyl ester which may have lower alkyl, higher alkyl ester, and [5-(lower)alkyl-2-oxo-1,3-dioxol-4-yl](lower)alkyl ester;

and the more preferred one may be methyl ester, ethyl ester, isobutyl ester, butyl ester, pentyl ester, hexyl ester, benzyl ester, 4-trifluoromethylbenzyl ester, 4-chlorobenzyl ester, adamantyl ester, (5-methyl-2-oxo-1,3-dioxol-4-yl)methyl ester, (1-cyclohexyloxycarbonyloxy)ethyl ester and pivaloyloxymethyl ester.

Suitable "lower alkanyl-ylidene" may include straight or branched one such as methine, 1-ethanyl-2-ylidene, 1-propanyl-3-ylidene, 2-methyl-1-propanyl-3-ylidene, 7-pentanyl-5-ylidene, 1-hexanyl-6-ylidene and the like, in which the preferred one may be (C1–C4)alkanyl-ylidene; and the more preferred one may be methine.

Suitable "lower alkylene" may include straight or branched one such as methylene, ethylene, trimethylene, tetramethylene, pentamethylene, hexamethylene, methylmethylene, 1-ethylethylene, 2-ethylpropylene, and the like, in which the preferred one may be $(C_1-C_4)$alkylene; and the more preferred one may be methylene, ethylene and trimethylene.

Suitable "lower alkenylene" may include straight or branched one having 2 to 6 carbon atom(s) such as vinylene, propenylene, butenylene, 1 or 2 or 3-pentenylene, 1 or 2 or 3-hexenylene, methylvinylene, ethylvinylene, 1 or 2 or 3-methylpropenylene, 1 or 2 or 3-ethylpropenylene, 1 or 2 or 3 or 4-methyl-1 or 2-butenylene, or the like.

Suitable "amino protective group" may include acyl group as explained below, a conventional protecting group such as ar(lower)alkyl which may have 1 to 3 suitable substituent(s) (e.g. benzyl, phenethyl, 1-phenylethyl, benzhydryl, trityl, etc.), [5-(lower)alkyl-2-oxo-1,3-dioxol-4-yl](lower)alkyl [e.g. (5-methyl-2-oxo-1,3-dioxol-4-yl)methyl, etc.] or the like; and the like.

Suitable "acyl group" and "acyl" may include aliphatic acyl, aromatic acyl, arylaliphatic acyl and heterocyclic-aliphatic acyl derived from carboxylic acid, carbonic acid, carbamic acid, sulfonic acid, and the like.

Suitable example of said "acyl group" may be illustrated as follows.

Aliphatic acyl such as lower or higher alkanoyl (e.g., formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.);

lower, or higher alkoxycarbonyl (e.g., methoxycarbonyl, ethoxycarbonyl, t-butoxycarbonyl, t-pentyloxycarbonyl, heptyloxycarbonyl, etc.);

lower or higher alkylsulfonyl (e.g., methylsulfonyl, ethylsulfonyl, etc.);

lower or higher alkoxysulfonyl (e.g., methoxysulfonyl, ethoxysulfonyl, etc.); or the like;

Aromatic acyl such as aroyl (e.g., benzoyl, toluoyl, naphthoyl, etc.);

ar(lower)alkanoyl [e.g., phenyl(C1–C6)alkanoyl (e.g., phenylacetyl, phenylpropanoyl, phenylbutanoyl, phenylisobutanoyl, phenylpentanoyl, phenylhexanoyl, etc.), naphthyl(C1–C6)alkanoyl (e.g., naphthylacetyl, naphthylpropanoyl, naphthylbutanoyl, etc), etc.];

ar(lower)alkenoyl [e.g., phenyl(C3–C6)alkenoyl (e.g., phenylpropenoyl, phenylbutenoyl, phenylmethacryloyl, phenylpentenoyl, phenylhexenoyl, etc.), naphthyl (C3–C6)alkenoyl (e.g., naphthylpropenoyl, naphthylbutenoyl, etc.), etc.];

ar(lower)alkoxycarbonyl [e.g., phenyl(C1–C6) alkoxycarbonyl (e.g., benzyloxycarbonyl, etc.), etc.];

aryloxycarbonyl (e.g., phenoxycarbonyl, naphthyloxycarbonyl, etc.);

aryloxy(lower)alkanoyl (e.g., phenoxyacetyl, phenoxypropionyl, etc.);

arylcarbamoyl (e.g., phenylcarbamoyl, etc.);

arylthiocarbamoyl (e.g., phenylthiocarbamoyl, etc.);

arylglyoxyloyl (e.g., phenylglyoxyloyl, naphthylglyoxyloyl, etc.);

arylsulfonyl which may have 1 to 4 lower alkyl (e.g., phenylsulfonyl, p-tolylsulfonyl, etc.); or the like;

Heterocyclic acyl such as heterocycliccarbonyl;

heterocyclic(lower)alkanoyl (e.g., heterocyclicacetyl, heterocyclicpropanoyl, heterocyclicbutanoyl, heterocyclicpentanoyl, heterocyclichexanoyl, etc.);

heterocyclic(lower)alkenoyl (e.g., heterocyclicpropenoyl, heterocyclicbutenoyl, heterocyclicpentenoyl, heterocyclichexenoyl, etc.);

heterocyclicglyoxyloyl; or the like;

in which suitable "heterocyclic moiety" in the terms "heterocycliccarbonyl", "heterocyclic(lower)alkyl", heterocyclic(lower)alkenoyl" and "heterocyclicglyoxyloyl" as mentioned above means, in more detail, saturated or unsaturated monocyclic or polycyclic heterocyclic group containing at least one hetero-atom such as an oxygen, sulfur, nitrogen atom and the like.

And, especially preferable heterocyclic group may be heterocyclic group such as unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

saturated 3 to 8-membered (more preferably 5 or 6-membered) heteromonocyclic group containing 1 to 4 nitrogen atom(s), for example, pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, indolizinyl, benzimidazolyl, quinolyl, dihydroquinolyl, isoquinolyl, indazolyl, quinoxalinyl, dihydroquinoxalinyl, benzotriazolyl, etc.;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc), etc.;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, dihydrodithionyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered (more preferably 5 or 6-membered) heteromonocyclic group containing an oxygen atom, for example, furyl, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc.; and the like.

The acyl moiety as mentioned above may have one to ten, same or different, suitable substituent(s) such as lower alkyl (e.g., methyl, ethyl, propyl, etc.);

lower alkoxy (e.g., methoxy, ethoxy, propoxy, etc.);

lower alkylthio (e.g., methylthio, ethylthio, etc.);

lower alkylamino (e.g., methylamino, ethylamino, propylamino, etc.);

cyclo(lower)alkyl [e.g. cyclo(C3–C6)alkyl (e.g., cyclopentyl, cyclohexyl, etc.]);

cyclo(lower)alkenyl [e.g. cyclo(C3–C6)alkenyl (e.g., cyclohexenyl, cyclohexadienyl, etc);

halogen (e.g., fluorine, chlorine, bromine, iodine); amino; amino protective group as mentioned above; hydroxy; protected hydroxy as mentioned below; cyano; nitro; carboxy; protected carboxy as mentioned above; sulfo; sulfamoyl; imino; oxo;

amino(lower)alkyl (e.g., aminomethyl, aminoethyl, etc.); carbamoyloxy; hydroxy(lower)alkyl (e.g., hydroxymethyl, 1 or 2-hydroxyethyl, 1 or 2 or 3-hydroxypropyl, etc.), or the like.

Suitable "protected hydroxy" may include acyl as mentioned above, phenyl(lower)alkyl which may have one or more suitable substituent(s) (e.g., benzyl, 4-methoxybenzyl, trityl, etc.), trisubstituted silyl [e.g., tri(lower)alkylsilyl (e.g., trimethylsilyl, t-butyldimethylsilyl, etc.), etc.], tetrahydropyranyl and the like.

The more preferred example of "amino protective group" may be lower alkoxycarbonyl or ar(lower)alkoxycarbonyl and the most preferred one may be t-butoxycarbonyl or benzyloxycarbonyl.

Suitable "lower alkylene" in the term "lower alkylene which may have one or more suitable substituent(s)" can be referred to the ones as exemplified above.

Suitable example of "suitable substituent(s)" in the term "lower alkylene which may have one or more suitable substituent(s)" may include lower alkyl (e.g., methyl, ethyl, propyl, isopropyl, butyl, isobutyl, t-butyl, pentyl, neopentyl, t-pentyl, hexyl, etc.);

lower alkoxy (e.g., methoxy, ethoxy, propoxy, isopropoxy, isobutoxy, t-butoxy, pentyloxy, neopentyloxy, t-pentyloxy, hexyloxy, etc.);

lower alkenyl [e.g. (C2–C6)alkenyl (e.g., vinyl,.1-propenyl, allyl, 1-methylallyl, 1 or 2 or 3-butenyl, 1 or 2 or 3 or 4-pentenyl, 1 or 2 or 3 or 4 or 5-hexenyl, etc.)];

lower alkynyl [e.g. (C2–C6)alkynyl (e.g., ethynyl, 1propynyl, propargyl, 1-methylpropargyl, 1-ethylpropargyl, 1 or 2 or 3-butynyl, 1 or 2 or 3 or 4-pentynyl, 1 or 2 or 3 or 4 or 5 hexynyl, etc.);

mono(or di or tri)halo(lower)alkyl (e.g., fluoromethyl, difluoromethyl, trifluoromethyl, chloromethyl, dichloromethyl, trichloromethyl, bromomethyl, dibromomethyl, tribromomethyl, 1 or 2-fluoroethyl, 1 or 2-bromoethyl, 1 or 2-chloroethyl, 1,1-difluoroethyl, 2,2-difluoroethyl, etc.);

halogen (e.g., chlorine, bromine, fluorine, iodine);

carboxy; protected carboxy as mentioned above; hydroxy; protected hydroxy as mentioned above;

aryl (e.g., phenyl, naphthyl, etc.);

heterocyclic group as mentioned above [e.g. unsaturated condensed heterocyclic group containing 1 to 4 nitrogen atom(s) (e.g. indolyl, isoindolyl, indolynyl, indolizinyl, benzimidazolyl, quinolyl, dihydroquinolyl, isoquinolyl, indazolyl, quinoxalinyl, dihydroquinoxalinyl, benzotriazolyl, etc.)];

ar(lower)alkyl such as phenyl(lower)alkyl (e.g., benzyl, phenethyl, phenylpropyl, etc.);

ar(lower)alkyl having one or more suitable substituent(s) such as ar(lower)alkyl having one or more (preferably 1 to 4) lower alkoxy, halogen, cyano, halo(lower)alkyl, lower alkylene dioxy or the like;

carboxy(lower)alkyl; protected carboxy(lower)alkyl; nitro; amino;

protected amino, i.e. amino protected by aforesaid "amino protective group", preferably, acylamino, in which acyl moiety can be aforementioned "acyl", such as aliphatic acylamino such as lower or higher alkanoylamino (e.g., formylamino, acetylamino, propanoylamino, butanoylamino, 2-methylpropanoylamino, pentanoylamino, 2,2-dimethylpropanoylamino, hexanoylamino, heptanoylamino, octanoylamino, nonanoylamino, decanoylamino, undecanoylamino, dodecanoylamino, tridecanoylamino, tetradecanoylamino, pentadecanoylamino, hexadecanoylamino, heptadecanoylamino, octadecanoylamino, nonadecanoylamino, icosanoylamino, etc.), cyclo(lower)alkylcarbonylamino [e.g. cyclo(C3–C6)alkylcarbonylamino (e.g. cyclopropylcarbonylamino, cyclobutylcarbonylamino, cyclopentylcarbonylamino, cyclohexylcarbonylamino, etc.)], lower or higher alkoxycarbonylamino (e.g., methoxycarbonylamino, ethoxycarbonylamino, t-butoxycarbonylamino, pentyloxycarbonylamino, heptyloxycarbonylamino, etc.), lower alkoxy(lower)alkanoylamino (e.g. methoxyacetylamino, 2- or 3-methoxypropionylamino, ethoxyacetylamino, 2- or 3-ethoxypropionylamino, etc.), lower alkynylcarbonylamino [e.g. (C2–C6)alkynylcarbonylamino (e.g. propargylcarbonylamino, 1-methylpropargylcarbonylamino, 1- or 2- or 3-butynylcarbonylamino, etc.), lower or higher alkylsulfonylamino (e.g., methylsulfonylamino, ethylsulfonylamino, propylsulfonylamino, n-butylsulfonylamino, sec-butylsulfonylamino, t-butylsulfonylamino, n-pentylsulfonylamino, neopentylsulfonylamino, hexylsulfonylamino, etc.), lower or higher alkoxysulfonylamino (e.g., methoxysulfonylamino, ethoxysulfonylamino, etc.), aroylamino which may have one or more (preferably 1 to 3) suitable substituent(s) (e.g. benzoylamino, toluoylamino, naphthoylamino, 2- or 3- or 4-hydroxybenzoylamino, 2- or 3- or 4-methoxybenzoylamino, 2- or 3- or 4-chlorobenzoylamino, phenylbenzoylamino, etc.), ar(lower)alkanoylamino [e.g., phenyl(C1–C6)alkanoylamino (e.g., phenylacetylamino, phenylpropanoylamino, phenylbutanoylamino, phenylisobutanoylamino, phenylpentanoylamino, phenylhexanoylamino, etc.), naphthyl(lower)alkanoylamino (e.g., naphthylacetylamino, naphthylpropanoylamino, naphthylbutanoylamino, etc.), etc.], ar(lower)alkenoylamino [e.g., phenyl(C3–C6)alkenoylamino (e.g., phenylpropenoylamino, phenylbutenoylamino, phenylmethacryloylamino, phenylpentenoylamino, phenylhexenoylamino, etc.), naphthyl(C3–C6)alkenoylamino (e.g., naphthylpropenoylamino, naphthylbutenoylamino, etc.], ar(lower)alkoxycarbonylamino [e.g., phenyl(C1–C6)alkoxy-carbonylamino (e.g. benzyloxycarbonylamino, phenethyloxycarbonylamino, etc.), etc.], aryloxycarbonylamino (e.g., phenoxycarbonylamino, naphthyloxycarbonylamino, etc.), aryloxy(lower)alkanoylamino (e.g., phenoxyacetylamino, phenoxypropionylamino, etc.), arylcarbamoylamino (e.g., phenylcarbamoylamino, etc.), arylthiocarbamoylamino (e.g., phenylthiocarbamoylamino, etc.), arylglyoxyloylamino (e.g., phenylglyoxyloylamino, naphthylglyoxyloylamino, etc.), arylsulfonylamino (e.g. phenylsulfonylamino, p-tolylsulfonylamino, etc.), or the like;

di(lower)alkylamino (e.g., dimethylamino, diethylamino, diisopropylamino, ethylmethylamino, isopropylmethylamino, ethylmethylamino, ethylpropylamino, etc.);

hydroxy(lower)alkyl; protected hydroxy(lower)alkyl; acyl as mentioned above; cyano; mercapto; oxo;

lower alkylthio(lower)alkyl (e.g. methylthiomethyl, ethylthiomethyl, propylthiomethyl, isopropylthiomethyl, butylthiomethyl, methylthioethyl, ethylthioethyl, etc.);

arylthio(lower)alkyl (e.g. phenylthiomethyl, phenylthioethyl, etc.);

arylsulfonyl(lower)alkyl (e.g. phenylsulfonylmethyl, phenylsulfonylethyl, p-tolylsulfonylmethyl, p-tolylsulfonylethyl, etc.);

lower alkylsulfonyl(lower)alkyl (e.g. methylsulfonylmethyl, ethylsulfonylmethyl, propylsulfonylmethyl, etc.);

acylamino(lower)alkyl, in which acyl moiety can be aforementioned "acyl" [e.g., arylsulfonylamino(lower)alkyl (e.g., phenylsulfonylaminomethyl, phenylsulfonylaminoethyl, p-tolylsulfonylaminomethyl, p-tolylsulfonylethyl, etc.), lower alkylsulfonylamino(lower)alkyl (e.g., methylsulfonylaminomethyl, ethylsulfonylaminomethyl, propylsulfonylaminomethyl, butylsulfonylaminomethyl, t-butylsulfonylaminomethyl, pentylsulfonylaminoethyl, etc.), etc.];

lower alkylcarbonyl(lower)alkyl (e.g. methylcarbonylmethyl, ethylcarbonylmethyl, propylcarbonylmethyl, etc.);

aroyl(lower)alkyl (e.g. benzoylmethyl, naphthoylmethyl, toluoylmethyl, anisoylmethyl, etc.);

heterocyclic(lower)alkyl such as (lower)alkyl having heterocyclic group as exemplified above [e.g. (C1–C6)alkyl having unsaturated condensed heterocyclic group containing 1 to 4 nitrogen atom(s) (e.g. indolylethyl, isoindolylethyl, indolyinylmethyl, indolizinylethyl, benzimidazolylmethyl, quinolylethyl, dihydroquinolylmethyl, isoquinolylethyl, indazolylethyl, quinoxalinylethyl, dihydroquinoxalinylmethyl, benzotriazolylethyl, etc.)];

lower alkyl sulfamoyl(lower)alkyl (e.g. methylsulfamoylmethyl, ethylsulfamoylmethyl, n-propylsulfamoylmethyl, isopropylsulfamoylmethyl, n-butylsulfamoylmethyl, t-butylsulfamoylmethyl, methylsulfamoylethyl, etc.);

arylsulfamoyl(lower)alkyl (e.g. phenylsulfamoylmethyl, tolylsulfamoylmethyl, phenylsulfamoylethyl, naphthylsulfamoylmethyl, etc.);

lower alkylcarbamoyl(lower)alkyl (e.g. methylcarbamoylmethyl, ethylcarbamoylmethyl, n-propylcarbamoylmethyl, isopropylcarbamoylmethyl, n-butylcarbamoylmethyl, t-butylcarbamoylmethyl, methylcarbamoylethyl, etc.);

arylcarbamoyl(lower)alkyl (e.g. phenylcarbamoylmethyl, tolylcarbamoylmethyl, phenylcarbamoylethyl, naphthylcarbamoylmethyl, etc.); ar(lower)alkylcarbamoyl which may have one or more suitable substituent(s) (e.g. phenyl(C1–C6)alkylcarbamoyl which may have 1 to 3 lower alkoxy (e.g. 2-methoxyphenethylcarbamoyl, 3-methoxyphenethylcarbamoyl, 4-methoxyphenethylcarbamoyl, etc.) and the like, in which the more preferred one may be (C1–C6)alkyl; (C2–C6)alkenyl; (C2–C6)alkynyl; phenyl; phenyl (C1–C6)alkyl; phenyl(C1–C6)alkyl having 1 to 4 (C1–C6)alkoxy, halo(C1–C6)alkyl or (C1–C6)alkylene dioxy; (C1–C6)alkyl having unsaturated condensed heterocyclic group containing 1 to 4 nitrogen atom(s); cyano; amino; (C1–C6)alkanoylamino; aroylamino which may have 1 to 3 hydroxy, (C1–C6)alkoxy, halogen or phenyl; cyclo(C3–C6)alkylcarbonylamino; (C1–C6)alkoxy (C1–C6)alkylcarbonylamino; (C2C6) alkynylcarbonylamino; (C1–C6)alkylsulfonylamino; phenylsulfonylamino; phenyl(C1–C6)alkylcarbamoyl;

and the more preferred one may be methyl, ethyl, vinyl, ethynyl, cyano, phenyl, phenethyl, 2-methoxyphenethyl, 3-methoxyphenethyl, 4-methoxyphenethyl, 3,4-dimethoxyphenethyl, 3-trifluoromethylphenethyl, 3,4-methylenedioxyphenethyl, 2-indolylethyl, 4-methoxyphenethylcarbamoyl, phenylsulfonylamino, n-butylsulfonylaminomethyl, benzoylamino, amino, acetylamino, p-hydroxybenzoylamino, p-methoxybenzoylamino, p-chlorobenzoylamino, n-butanoylamino, cyclopropylcarbonylamino, 3-methoxypropionylamino, biphenylcarbonylamino and propargylcarbonylamino.

Suitable "N-containing heterocyclic group" may include saturated or unsaturated monocyclic or polycyclic heterocyclic group containing at least nitrogen atom and which may also contain the other hetero-atom such as an oxygen, sulfur atom or the like.

And, especially preferable N-containing heterocyclic group may be heterocyclic group such as unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl, dihydropyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), etc.;

saturated 3 to 8-membered (more preferably 5 or 6-membered heteromonocyclic group containing 1 to 4 nitrogen atom(s), for example, pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, indolizinyl, benzimidazolyl, quinolyl, tetrahydroquinolyl (e.g. 1,2,3,4-tetrahydroquinolyl, etc.), dihydroquinolyl, isoquinolyl, indazolyl, quinoxalinyl, dihydroquinoxalinyl, benzotriazolyl, etc.;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl, etc.), etc.;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered heteromonocyclic group containing 1 to 2 sulfur atom(s) and 1 to 3 nitrogen atom(s), for example, thiomorpholinyl, thiazolidinyl, etc.;

unsaturated condensed heterocyclic group containing 1 to 2 sulfur atom(s) and 1 to 3 nitrogen atom(s), for example, benzothiazolyl, benzothiadiazolyl, etc. and the like, in which the preferred one may be saturated 5 or 6-membered heteromonocyclic group containing 1 to 4 nitrogen atom(s), unsaturated condensed heterocyclic group containing 1 to 4 nitrogen atom(s), or saturated 5 or 6-membered heteromonocyclic group containing 1 to 2 oxygen atom(s) and 1 to 3 nitrogen atom(s);

and the more preferred one may be piperidyl, pyrrolidinyl, morpholinyl and 1,2,3,4-tetrahydroquinolyl.

Suitable "N-containing cyclo(lower)alkyl" in-the term "N-containing cyclo(lower)alkyl which may have one or more suitable substituent(s)" may include 3 to 8-membered cycloalkyl containing 1 to 3 nitrogen atom(s), for example, azetidinyl, pyrrolidinyl, piperidyl, piperazinyl, etc.

Suitable "suitable substituent(s)" in the term "N-containing cyclo(lower)alkyl which may have one or more suitable substituent(s)" may include oxo, amino protective group as mentioned above.

Suitable "suitable substituent(s)" in the term "lower alkylene, lower alkanyl-ylidene or lower alkenylene each of which may have one or more suitable substituent(s)", may include lower alkyl or oxo.

Suitable "suitable substituent(s)" in the term "N-containing heterocyclic group which may have one or more suitable substituent(s)" may include lower alkyl, phenyl, halogen or oxo.

Suitable "lower alkynylene" may include the ones having 2 to 6 carbon atoms such as ethynylene, 2-propynylene, 2- or 3-butynylene, 2- or 3- or 4-pentynylene or 2- or 3- or 4- or 5-hexynylene.

In the compound (I) as explained above, the preferred one is the following compound (I-A):

Compound (I-A):

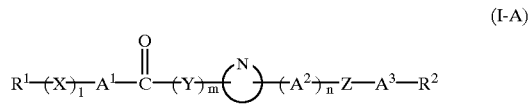

(I-A)

wherein $R^1$ is 3 to 8 membered cycloalkyl containing 1 to 3 nitrogen atom(s) which may have one or more suitable substituent(s), $R^2$ is carboxy or esterified carboxy, $A^1$ is lower alkylene, lower alkanyl-ylidene or lower alkenylene, each of which may have one or more suitable substituent(s), $A^2$ is lower alkylene, $A^3$ is lower alkylene which may have one or more suitable substituent(s),

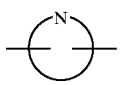

is a group of the formula:
wherein

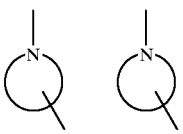

is saturated 3 to 8 membered heteromonocyclic group containing 1 to 4 nitrogen atom(s) which may have one or more suitable substituent(s), unsaturated condensed heterocyclic group containing 1 to 4 nitrogen atom(s) which may have one or more suitable substituent(s) or saturated 3 to 8-membered heteromonocyclic group containing 1 to 2 oxygen atom(s) and 1 to 3 nitrogen atom(s) which may have one or more suitable substituent(s), X is O, S, or NH,
Y is NH,
Z is

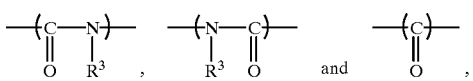

(wherein $R^3$ is hydrogen or lower alkyl),
l is an integer of 0 or 1,
m is an integer of 0 or 1,
n is an integer of 0 or 1,
and the more preferred one is the aforementioned compound (I-A),
wherein
$R^1$ is piperidyl which may have 1 or 2 oxo or [5(lower)alkyl-2-oxo-1,3-dioxol-4-yl]-(lower)alkyl,

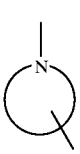

is piperidyl, morpholinyl, tetrahydroquinolyl or pyrrolydinyl,
$A^3$ is lower alkylene which may have 1 to 3 suitable substituent(s) selected from the group consisting of (C1–C6)alkyl;, (C2–C6)alkenyl; (C2–C6)alkynyl; phenyl; phenyl(C1–C6)alkyl; phenyl(C1–C6)alkyl having 1 to 4 (C1–C6)alkoxy, halo(C1–C6)alkyl or (C1–C6)alkylene dioxy; (C1–C6)alkyl having unsaturated condensed heterocyclic group containing 1 to 4 nitrogen atom(s); cyano; amino; (C1–C6)alkanoylamino; aroylamino which may have 1 to 3 hydroxy, (C1–C6)alkoxy, halogen or phenyl; cyclo(C3–C6)alkylcarbonylamino; (C1–C6)alkoxy(C1–C6)alkylcarbonylamino; (C2–C6)alkynylcarbonylamino; (C1–C6)alkylsulfonylamino; phenylsulfonylamino; and phenyl(C1–C6)alkylcarbamoyl;

$R^2$, $R^3$, $A^1$, $A^2$, X, Y or Z are each as defined above,
l is an integer of 0,
m is an integer of 0,
n is an integer of 0,
and the much more preferred one is the aforementioned compound (I-A),
wherein
$R^1$ is piperidyl,
$A^1$ is lower alkylene or lower alkanyl-ylidene,
$A^3$ is lower alkylene which may have lower alkyl, lower alkynyl or lower alkanoylamino,

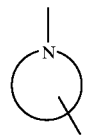

is piperidyl,
Z is

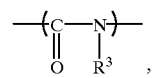

$R^2$, $R^3$, $A^2$, Y, l, m and n are each as defined in the more preferred one,
and the another much more preferred one is the aformentioned compound (I-A),
wherein
$R^1$ is piperidyl,
$A^1$ is lower alkylene or lower alkanyl-ylidene,
$A^3$ is lower alkylene which may have lower alkyl, lower alkynyl or lower alkanoylamino,

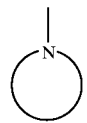

is morpholinyl,
Z is

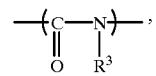

$R^2$, $R^3$, $A^2$, Y, l, m and n are each as defined in the more preferred one.

In the compound (I) as explained above, another preferred one is the following compound (I-B):
Compound (I-B):

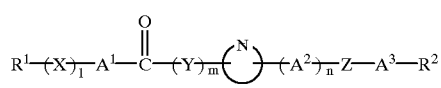

(I-B)

wherein
$R^1$ is N-containing cycloalkyl which may have one or more suitable substituent(s), R² is carboxy or esterified carboxy,
A¹ is lower alkylene, lower alkanyl-ylidene or lower alkenylene, each of which may have one or more suitable substituent(s),
A² is lower alkylene,
A³ is lower alkylene which may have one or more suitable substituent(s),

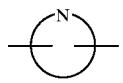

is a group of the formula:

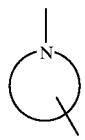

wherein

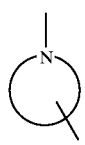

is N-containing heterocyclic group which may Wave one or more suitable substituent(s),
X is O,
Y is NH,
Z is

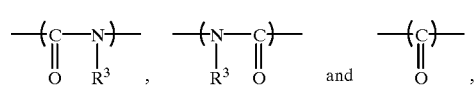

(wherein R³ is hydrogen or lower alkyl),
l is an integer of 1,
m is an integer of 0 or 1,
n is an integer of 0 or 1,
and the more preferred one is the aforementioned compound (I-B),
wherein
R¹ is piperidyl, piperazinyl or azetidinyl, each of which may have 1 or 2 oxo or [5-(lower)alkyl-2-oxo-1,3-dioxol-4-yl]-(lower)alkyl,

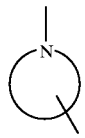

is piperidyl, morpholinyl, tetrahydroquinolyl or pyrrolydinyl,
A³ is lower alkylene which may have 1 to 3 suitable substituent(s) selected from the group consisting of (C1–C6)alkyl; (C2–C6)alkenyl; (C2–C6)alkynyl; phenyl; phenyl(C1–C6)alkyl; phenyl(C1–C6)alkyl having 1 to 4 (C1–C6)alkoxy, halo(C1–C6)alkyl or (C1–C6)alkylene dioxy;. (C1–C6)alkyl having unsaturated condensed heterocyclic group containing 1 to 4 nitrogen atom(s); cyano; amino; (C1–C6)alkanoylamino; aroylamino which may have 1 to 3 hydroxy, (C1–C6)alkoxy, halogen or phenyl; cyclo(C3–C6)alkanoylamino; (C1–C6)alkoxy(C1–C6)alkylcarbonylamino; (C2–C6)alkynylcarbonylamino; (C1–C6)alkysulfonylamino; phenylsulfonylamino; and phenyl(C1–C6)alkylcarbamoyl;
R², R³, A¹, A², X, Y, Z or l are each as defined above,
m is an integer of 0,
n is an integer of 0,
and the much more preferred one is the aforementioned compound (I-B),
wherein
R¹ is piperidyl,
A¹ is lower alkylene,
A³ is lower alkylene which may have lower alkyl, lower alkynyl or lower alkanoylamino,

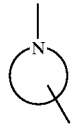

is piperidyl,
Z is

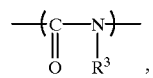

R², R³, A², X, Y, l, m and n are each as defined in the more preferred one,
and the much more preferred one is the aforementioned compound (I-B),
wherein
R¹ is piperidyl,
A¹ is lower alkylene,
A³ is lower alkylene which may have lower alkyl, lower alkynyl or lower alkanoylamino,

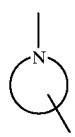

is morpholinyl,
Z is

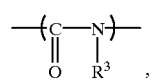

R², R³, A², X, Y, l, m and n are each as defined in the more preferred one.
In the compound (I) as explained above, another preferred one is the following compound (I-C):

Compound (I-C):

$$R^1-(X)_l-A^1-\overset{O}{\underset{\|}{C}}-(Y)_m-\underset{\underset{}{\bigcirc}}{\overset{N}{\diagup}}-(A^2)_n-Z-A^3-R^2 \quad \text{(I-C)}$$

wherein
- $R^1$ is piperidyl which may have 1 or 2 oxo or [5-(lower) alkyl-2-oxo-1,3-dioxol-4-yl]-(lower)alkyl,
- $R^2$ is carboxy or esterified carboxy,
- $A^1$ is lower alkanyl-ylidene or lower alkenylene,
- $A^2$ is lower alkylene,
- $A^3$ is lower alkylene which may have lower alkyl, lower alkynyl or lower alkanoylamino, $$-\underset{\bigcirc}{\overset{N}{\diagup}}-$$

is a group of the formula:
wherein $$-\underset{\bigcirc}{\overset{|}{\underset{}{N}}} \quad -\underset{\bigcirc}{\overset{|}{\underset{}{N}}}$$

is piperidyl, morpholinyl, tetrahydroquinolyl or pyrrolydinyl,
Y is NH,
Z is $$-(\underset{\overset{\|}{O}}{C}-\underset{\overset{|}{R^3}}{N})-,$$

(wherein $R^3$ is hydrogen),
l is 0,
m is an integer of 0 or 1,
n is an integer of 0 or 1,
and the other preferred one is the aforementioned compound (I-C),
wherein
- $A^3$ is lower alkylene having lower alkynyl or lower alkanoylamino, $$-\underset{\bigcirc}{\overset{|}{\underset{}{N}}}$$

is piperidyl or morpholinyl,
$R^1$, $R^2$, $R^3$, $A^1$, $A^2$, X, Y, Z, and l are each as defined above,
m is an integer of 0,
n is an integer of 0, The processes for preparing the object compound (I) of the present invention are explained in detail in the following.

Process 1

The object compound (Ia) or a salt thereof can be prepared by reacting a compound (II) or its reactive derivative at the carboxy group or a salt thereof with a compound (III) or its reactive derivative at the amino group or a salt thereof.

Suitable reactive derivative at the carboxy group of the compound (II) may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole, tetrazole or 1-hydroxy-1H-benzotriazole; or an activated ester [e.g. cyanomethyl ester, methoxymethyl ester, dimethyliminomethyl $$[(CH_3)_2\overset{+}{N}=C-]$$

ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivative can optionally be selected from them according to the kind of the compound (II) to be used.

Suitable salts of the compound (II) and its reactive derivative can be referred to the ones as exemplified for the compound (I).

Suitable reactive derivative at the amino group of the compound (III) may include Schiff's base type imino or its tautomeric enamine type isomer formed by the reaction of the compound (III) with a carbonyl compound such as aldehyde, ketone or the like; a silyl derivative formed by the reaction of the compound (III) with a silyl compound such as bis(trimethylsilyl)acetamide, mono(trimethylsilyl)acetamide, bis(trimethylsilyl)urea or the like; a derivative formed by reaction of the compound (III) with phosphorus trichloride or phosgene, and the like.

Suitable salts of the compound (III) and its reactive derivative can be referred to the ones as exemplified for the compound (I).

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (II) in used in a free acid form or its salt form, the reaction is preferable carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkylphosphite; ethyl polyphosphate; isopropyl polyphosphate; phosphorous oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl) isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, methanesulfonyl chloride, etc.; or the like.

The reaction may also be carried out in the presence of an inorganic or organic base such as an alkali metal carbonate, alkali metal bicarbonate, tri(lower)alkylamine, pyridine, N-(lower)alkylmorpholine, N,N-di(lower) alkylbenzylamine, or the like.

The reaction temperature is not critical, and the reaction is usually carried out under cooling to warming.

Process 2

The object compound (Ib) or a salt thereof can be prepared by reacting a compound (IV) or its reactive derivative at the carboxy group or a salt thereof with a compound (V) or its reactive derivative at the amino group or a salt thereof.

This reaction can be carried out in a similar manner to that of Process 1 mentioned in the above, and therefore the reaction mode and reaction conditions [e.g. reactive derivative, solvent, reaction temperature, etc.] of this reaction are to be referred to those as explained in Process 1.

Process 3

The object compound (IC) or a salt thereof can be prepared by reacting a compound (VII) or its reactive derivative at the carboxy group or a salt thereof with a compound (VI) or its reactive derivative at the amino group or a salt thereof.

This reaction can be carried out in a similar manner to that of Process 1 mentioned in the above, and therefore the reaction mode and reaction conditions [e.g. reactive derivative, solvent, reaction temperature, etc.] of this reaction are to be referred to those as explained in Process 1.

Process 4

The object compound (Ie) or a salt thereof can be prepared by subjecting a compound (Id) or a salt thereof to elimination reaction of amino protective group.

This reaction is carried out in accordance with a conventional method such as hydrolysis, reduction or the like.

The hydrolysis is preferably carried out in the presence of a base or an acid including Lewis acid.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.].

The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium, sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

The present invention includes within the scope of the invention the case that protected carboxy in $R^2$ is transformed into carboxy.

Process 5

The object compound (Ig) or a salt thereof can be prepared by subjecting a compound (If) or a salt thereof to elimination reaction of the carboxy protective group.

This reaction can be carried out in a similar manner to that of Process 4 mentioned in the above, and therefore the reaction mode and reaction conditions [e.g. base, acid, catalyst, solvent, reaction temperature, etc.] of this reaction are to be referred to those as explained in Process 4.

Process 6

The object compound (Id) or a salt thereof can be prepared by reacting the compound (Ie) or a salt thereof to protecting reaction of amino.

This reaction can be carried out according to a conventional manner such as the one described in Examples or the similar manners thereto.

Process 7

The object compound (If) or a salt thereof can be prepared by subjecting the compound (Ig) or a alt thereof to protecting reaction of carboxy.

This reaction can be carried out according to a conventional manner such as the ones described in Examples or the similar manners thereto.

Process 8

The object compound (Ii) or a salt thereof can be prepared by subjecting a compound (Ih) or a salt thereof to elimination reaction of amino protective group.

This reaction can be carried out in a similar manner to that of Process 4 mentioned in the above, and therefore the reaction mode and reaction conditions [e.g. reactive derivative, solvent, reaction temperature, etc.] of this reaction are to be referred to those as explained in Process 4.

Process 9

The object compound (Ih) or a salt thereof can be prepared by subjecting the compound (Ii) or its reactive derivative at the amino group, or a salt thereof to acylation reaction.

Suitable acylating agent to be used in the present acylation reaction may include the compound of the formula:

$$R^{10}\text{—OH} \qquad (X)$$

(wherein $R^{10}$ is acyl as mentioned before) or its reactive derivative, or a salt thereof.

Suitable reactive derivative at the amino group of the compound (Ii) may include Schiff's base type imino or its tautomeric enamine type isomer formed by the reaction of the compound (Ii) with a carbonyl compound such as aldehyde, ketone or the like; a silyl derivative formed by the reaction of the compound (Ii) with a silyl compound such as N,O-bis(trimethylsilyl)acetamide, N-trimethylsilylacetamide or the like; a derivative formed by the reaction of the compound (Ii) with phosphorus trichloride or phosgene, and the like.

Suitable reactive derivative of the compound (X) may include an acid halide, an acid anhydride, an activated ester, and the like. The suitable example may be an acid chloride; acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, alkanesulfonic acid (e.g., methanesulfonic acid, ethanesulfonic acid, etc.), sulfuric acid, alkylcarbonic acid, aliphatic carboxylic acid (e.g., pivalic acid, pentanoic acid, isopentanoic acid, 2-ethylbutyric acid, trichloroacetic acid, etc.); aromatic carboxylic acid (e.g., benzoic acid, etc.); a symmetrical acid anhydride; an activated amide with imidazole, 4-substituted imidazole, dimethylpyrazole, triazole or tetrazole; an activated ester (e.g., cyanomethyl ester, methoxymethyl ester, dimethyliminomethyl $[(CH_3)_2{}^+N=CH—]$ ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenylthio ester, p-nitrophenyl thioester, p-cresyl thioester, carboxymethyl thioester, pyranyl ester, pyridyl ester, piperidyl ester, 8-quinolyl thioester, etc.); an ester with a N-hydroxy compound (e.g., N,N-dimethylhydroxylamine, 1-hydroxy-2-(1H)-pyridone, N-hydroxysuccinimide, N-hydroxybenzotriazole, N-hydroxyphthalimide, 1-hydroxy-6-chloro-1H-benzotriazole, etc.); and the like. These reactive derivatives can optionally be selected from them accordingly to the kind of the compound (Ii) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely affect the reaction, or the mixture thereof.

When the compound (Ii) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diisopropylcarbodiimide; N-ethyl-N'-(3-dimethylaminopropyl)carbodiimide; N,N-carbonyl-bis(2-methylimidazole); pentamethyleneketene-N-cyclohexylimine; diphenylketene-N-cyclohexylimine; ethoxyacetylene; 1-alkoxy-1-chloroethylene; trialkyl phosphate; isopropyl polyphosphate; phosphorous oxychloride (phosphoryl chloride); phosphorous trichloride; thionyl chloride; oxalyl chloride; triphenylphosphite; 2-ethyl-7-hydroxybenzisoxazolium salt; 2-ethyl-5-(m-sulfophenyl) isoxazolium hydroxide intra-molecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorous oxychloride, etc.; or the like.

The reaction may also be carried out in the presence of an organic or inorganic base such as an alkali metal bicarbonate, tri(lower)alkylamine, pyridine, N-(lower) alkylmorphorine, N,N-di(lower)alkylbenzylamine, or the like.

The reaction temperature is not critical, and the reaction is usually carried out under cooling to heating.

The processes for preparing the starting compounds (IV) and (V) are explained in detail in the following.

Process A

The object compound (IX) or a salt thereof can be prepared by reacting a compound (II) or its reactive derivative at the carboxy group or a salt thereof with a compound (VIII) or its reactive derivative at the amino group or a salt thereof.

This reaction can be carried out in a similar manner to that of Process 1 mentioned in the above, and therefore the reaction mode and reaction conditions [e.g. reactive derivative, solvent, reaction temperature, etc.] of this reaction are to be referred to those as explained in Process 1.

Process B

The object compound (IV) or a salt thereof can be prepared by subjecting a compound (IX) or a salt thereof to elimination reaction of the carboxy protective group.

This reaction can be carried out in a similar manner to that of Process 4 mentioned in the above, and therefore the reaction mode and reaction conditions [e.g. base, acid, catalyst, solvent, reaction temperature, etc.] of this reaction are to be referred to those as explained in Process 4.

The present invention includes within the scope of the invention the case that amino protective group in $R^1$ is transformed into amino.

Process C

The object compound (Va) or a salt thereof can be prepared by reacting a compound (6) with acid.

Compound (6) can be prepared as follows.

Compound (2) can be prepared by reacting a compound (1) with formalin, and both compound (4) and compound (5) can be prepared by reacting a compound (2) with a compound (3) to Lipase-catalyzed reaction, and compound (6) can be prepared by reacting compound (5) with aqueous ammonia.

The reaction of each step can be carried out in a conventional manner such as the ones described in Preparations.

Process D

The object compound (Vb) or a salt thereof can be prepared by reacting a compound (11) with acid.

Compound (11) can be prepared as follows.

Compound (9) can be prepared by reacting a compound (7) with a compound (8) (wittig reaction), and compound (11) can be prepared by reacting a compound (9) with a compound (10).

The reaction of each step can be carried out in a conventional manner such as the ones described in Preparations.

When the object compound (I) obtained by the above-mentioned processes is in a free form, it can be converted into a salt form in a conventional manner. On the other hand, when the object compound (I) thus obtained is in a salt form, it can be converted into a free form or another salt form also in a conventional manner.

The compounds obtained by the above Processes 1 to 9 and A to D can be isolated and purified by a conventional method such as pulverization, recrystallization, column-chromatography, reprecipitation of the like.

It is to be noted that each of the object compound (I) may include one or more stereoisomer such as optical isomer(s) and geometrical isomer(s) due to asymmetric carbon atom(s) and double bond(s) and all such isomers and mixture thereof are included within the scope of this invention.

Now in order to show the utility of the object compound (I), some pharmacological test data of the representative compound (I) of the present invention are shown in the following.

Test 1: Effect on Platelet Aggregation Induced by Adenosine Diphosphate (ADP)

Test Compound (1) the compound of Example 21 (3)

Test Method

Platelet rich plasma (PRP) which contains $3\times10^8$ platelets/ml was prepared from human blood. To the 225 μl of PRP, 25 μl of drug solution* was added, and then stirred for 2 minutes at 37° C. To the solution 5 μl of ADP (final 2.5 μM) was added as an aggregation inducer. Aggregation was measured by using an aggregometer (NBS HEMA-TRACER 801). Activity of inhibitor (test compound) was expressed as $IC_{100}$ value i.e. dose required for complete inhibition of platelet aggregation.

Drug solution* ——— Test compound was dissolved in water.

Test Result

| Test Compound | $IC_{100}$ (M) |
|---|---|
| (1) | $1.0 \times 10^{-6}$ |

The pharmaceutical composition of the present invention can be used in the form of a pharmaceutical preparation, for example, in solid, semisolid or liquid form, which contains the object compound (I) or a pharmaceutically acceptable salt thereof, as an active ingredient in admixture with an organic or inorganic carrier or excipient suitable for rectal, pulmonary (nasal or buccal inhalation), nasal, ocular, external (topical), oral or parenteral (including subcutaneous, intravenous and intramuscular) administrations or insufflation.

The active ingredient may be compounded, for example, with the usual non-toxic, pharmaceutically acceptable carriers for tablets, pellets, troches, capsules, suppositories, creams, ointments, aerosols, powders for insufflation, solutions, emulsions, suspensions, and any other form suitable for use. And, if necessary, in addition, auxiliary, stabilizing, thickening and coloring agents and perfumes may be used.

The object compound (I) or a pharmaceutically acceptable salt thereof is/are included in the pharmaceutical composition in an amount sufficient to produce the desired effect upon the process or condition of the diseases.

The pharmaceutical composition of the present invention can be manufactured by the conventional method in this field of the art. If necessary, the technique generally used in this field of the art for improving the bioavailability of a drug can be applied to the pharmaceutical composition of the present invention.

For applying the composition to a human being or an animal, it is preferable to apply it by intravenous (including i.v. infusion), intramuscular, pulmonary, or oral administration, or insufflation including aerosols from metered dose inhalator, nebulizer or dry powder inhalator.

While the dosage of therapeutically effective amount of the object compound (I) varies from and also depends upon the age and condition of each individual patient to be treated, in the case of intravenous administration, a daily dose of 0.001–100 mg of the object compound (I) per kg weight of a human being or an animal, in the case of intramuscular administration, a daily dose of 0.001–100 mg of the object compound (I) per kg weight of a human being or an animal, in case of oral administration, a daily dose of 0.001–200 mg of the object compound (I) per kg weight of a human being or an animal in generally given for the prevention and/or the treatment of aforesaid diseases in a human being or an animal.

The following Preparations and Examples are given for the purpose of illustrating the present invention in more detail.

PREPARATION 1

(1) To a mixture of (R)-ethyl nipecotinate (1.86 g), 3-(1-tert-butoxycarbonyl-4-piperidyl)propionic acid (3.04 g) and 1-hydroxybenztriazole (1.60 g) in N,N-dimethylformamide (20 ml) was added 1-ethyl-3-(3-dimethylaminopropyl)carbodiimide (2.16 ml) under stirring at 0° C. After stirring at ambient temperature overnight, the mixture was poured into water and extracted with ethyl acetate. The extract was washed with water, brine and dried over $MgSO_4$, and evaporated in vacuo. The residue was purified by chromatography on silica gel eluting with ($CHCl_3$:MeOH)=(100:1) to give (R)-ethyl 1-[3-(1-tert-butoxycarbonyl-4-piperidyl) propionyl]-3-piperidinecarboxylate as an oil (4.01 g).

IR (Film): 2960, 2900, 2840, 1710, 1665, 1630 $cm^{-1}$

NMR ($CDCl_3$, δ): 1.00–1.20 (1H, m), 1.28 (3H, t, J=7.1 Hz), 1.45 (9H, s), 1.48–1.88 (9H, m), 1.98–2.15 (1H, m), 2.31–2.51 (3H, m), 2.62–3.12 (4H, m), 3.35–3.47 (1/2H, m), 3.65–3.85 (1H, m), 4.00–4.22 (4H, m), 4.56–4.69 (1/2H, m)

Mass (m/z): 397 ($M^+$+1)

The following compounds were obtained according to a similar manner to that of Preparation 1 (1).

(2) Ethyl 1-[2-(1-benzyloxycarbonyl-4-piperidyloxy) acetyl]-3-piperidinecarboxylate IR (Film): 2930, 2860, 1720, 1690, 1640 $cm^{-1}$ NMR ($CDCl_3$, δ): 1.25 (3H, t, J=7.1 Hz), 1.46–1.94 (7H, m), 2.00–2.16 (1H, m), 2.40–2.59 (1H, m), 2.85–3.40 (4H, m), 3.56–3.64 (1H, m), 3.73–3.98 (3H, m), 4.04–4.32 (2+1/2H, m), 4.15 (2H, q, J=7.7 Hz), 4.49–4.60 (1/2H, m), 5.12 (2H, s), 7.30–7.37 (5H, m)

Mass (m/z): 433 (M⁺+1)

(3) (R)-Ethyl 1-[3-(1-benzyloxycarbonyl-4-piperidyl)-propionyl]-3-piperidinecarboxylate IR (Film): 2980, 2920, 2840, 1715, 1690, 1630 cm⁻¹

NMR (CDCl₃, δ): 1.05–1.30 (5H, m), 1.40–1.88 (8H, m), 1.98–2.15 (1H, m), 2.30–2.50 (3H, m), 2.70–3.10 and 3.35–3.47 (total 4H, m), 3.67–3.83 (1H, m), 3.98–4.21 and 4.55–4.66 (total 5H, m), 5.12 (2H, s), 7.29–7.37 (5H, m)

Mass (m/z): 431 (M⁺+1)

(4) Methyl 1-[3-(1-tert-butoxycarbonyl-4-piperidyl) propionyl]-3-pyrrolidinecarboxylate IR (Film): 3450, 1730, 1680, 1630 cm⁻¹

NMR (CDCl₃, δ): 1.07–1.18 (2H, m), 1.453 (9H, s), 1.57–1.69 (3H, m), 1.63 (3H, s), 2.12–2.31 (3H, m), 2.61–2.73 (2H, m), 3.02–3.20 (1H, m), 3.45–3.75 (7H, m), 4.05–4.15 (2H, m)

Mass (m/z): 369 (M⁺+1)

(5) 3-[3-(1-tert-butoxycarbonyl-4-piperidyl)propionyl] aminopyridine mp: 152–153° C.

IR (Nujol): 1680, 1600 cm⁻¹

NMR (CDCl₃, δ): 1.00–1.20 (2H, m), 1.45 (9H, s), 1.40–1.51 (1H, m), 1.61–1.75 (4H, m), 2.43 (2H, t, J=7.6 Hz), 2.39–2.46 (2H, m), 4.03–4.14 (2H, m), 7.28 (1H, t, J=7.0 Hz), 8.22 (1H, dd, J=5.7 and 2.3 Hz), 8.32 (1H, dd, J=4.7 and 1.4 Hz), 8.59 (1H, d, J=2.4 Hz), 8.65 (1H, s)

Mass (m/z): 334 (M⁺+1)

(6) Ethyl (S)-1-[3-(1-tert-butoxycarbonyl-4-piperidyl)-propionyl]-3-piperidinecarboxylate IR (Film): 2930, 2860, 1720, 1680, 1635 cm⁻¹

NMR (CDCl₃, δ): 1.03–1.23 (2H, m), 1.27 (3H, t, J=7.1 Hz), 1.45 (9H, s), 1.53–1.74 (9H, m), 1.98–2.15 (1H, m), 2.32–2.51 (3H, m), 2.60–3.11 (4H, m), 3.68–3.86 (1H, m), 4.03–4.22 (4H, m)

Mass (m/z): 397 (M⁺+1)

(7) N-[(R)-(1-benzyloxycarbonyl)-3-piperidylcarbonyl]-2 (S)-tert-butoxycarbonylamino-β-alanine ethyl ester IR (Film): 3320, 2975, 2930, 2860, 1700, 1680, 1660 cm⁻¹

NMR (CDCl₃, δ): 1.23–1.32 (1H, m), 1.28 (3H, t, J=7.1 Hz), 1.43 (9H, s), 1.47–1.67 (4H, m), 1.72–2.03 (2H, m), 2.23–2.40 (1H, m), 3.45–3.90 (4H, m), 4.13–4.25 (3H, m), 4.31–4.42 (1H, m), 5.16 (2H, d, J=6.7 Hz), 7.36–7.39 (5H, m)

Mass (m/z): 478 (M⁺+1)

(8) N-(3-Pyridyl)-3(S)-(tert-butoxycarbonylamino)-succinamic acid methyl ester

IR (Film): 2975, 1700, 1680, 1600 cm⁻¹

NMR (CDCl₃, δ): 1.49 (9H, s), 2.77 (1H, dd, J=17.1 and 6.2 Hz), 3.05 (1H, dd, J=17.1 and 4.4 Hz), 3.74 (3H, s), 4.63–4.72 (1H, m), 5.91–6.00 (1H, m), 7.23–7.30 (1H, m), 8.11 (1H, dq, J=8.3 and 1.0 Hz), 8.36 (1H, dd, J=4.8 and 1.4 Hz), 8.59 (1H, d, J=2.4 Hz), 8.83–8.87 (1H, br)

Mass (m/z): 324 (M⁺+1)

(9) N-[(3-Pyridyl)-2(S)-(tert-butoxycarbonylamino)]-succinamic acid ethyl ester mp: 134–135° C.

IR (Nujol): 3300, 1720, 1680, 1665 cm⁻¹

NMR (CDCl₃, δ): 1.28 (3H, t, J=7.1 Hz), 1.45 (9H, s), 2.96 (1H, dd, J=16.1 and 4.6 Hz), 3.09 (1H, dd, J=16.1 and 5.2 Hz), 4.24 (2H, q, J=7.1 Hz), 4.58 (1H, dt, J=8.3 and 4.9 Hz), 5.71–5.75 (1H, m), 7.24–7.30 (1H, m), 8.13–8.20 (1H, m), 8.32–8.37 (1H, m), 8.43–8.47 (1H, m), 8.57–8.61 (1H, m)

Mass (m/z): 338 (M⁺+1)

(10) N-[(3-Pyridyl)-3(R)-(tert-butoxycarbonylamino)]-succinamic acid benzyl ester IR (Film): 2970, 1705, 1670 cm⁻¹

NMR (CDCl₃, δ): 1.47 (9H, S), 2.83 (1H, dd, J=15.6 and 6.3 Hz), 3.07 (1H, dd, J=17.1 and 4.7 Hz), 4.65–4.75 (1H, m), 5.15 (2H, s), 5.93 (1H, d, J=8.4 Hz), 7.21–7.27 (1H, m), 7.33 (5H, s), 8.07 (1H, dq, J=8.3 and 1.0 Hz), 8.35 (1H, dd, J=4.7 and 1.4 Hz), 8.57 (1H, d, J=2.4 Hz), 8.87 (1H, s)

Mass (m/z): 4.00 (M⁺+1)

PREPARATION 2

(1) A solution of (R)-ethyl 1-[3-(1-tert-butoxycarbonyl-4-piperidyl)propionyl]-3-piperidinecarboxylate (3.99 g) in a mixture of methanol (10 ml), tetrahydrofuran (10 ml) and water (10 ml) was added lithium hydroxide (1.27 g) under stirring at 0° C. After stirring at ambient temperature for 1 hour, the mixture was acidified with 5% KHSO₄ aqueous solution and extracted with ethyl acetate. The extract was washed with water, brine and dried over MgSO₄, and evaporated in vacuo to give (R)-1-[3-(1-tert-butoxycarbonyl-4-piperidyl)propionyl]-3-piperidinecarboxylic acid (3.34 g).

mp: 102–104° C.

IR (Nujol): 1720, 1680, 1630 cm⁻¹

NMR (DMSO-d₆, δ): 0.84–1.10 (2H, m), 1.38–1.76 (8H, m), 1.38 (9H, s), 1.82–2.01 (1H, m), 2.20–2.45 (3H, m), 2.59–2.76 (2H, m), 2.89–3.09 (1H, m), 3.28–3.40 (1H, m), 3.69–3.98 and 4.31–4.44 (total 4H, m)

The following compounds were obtained according to a similar manner to that of Preparation 2 (1).

(2) (R)-1-[3-(1-Benzyloxycarbonyl-4-piperidyl)propionyl]-3-piperidinecarboxylic acid mp: 134–135° C.

IR (Nujol): 1715, 1680, 1600 cm⁻¹

NMR (DMSO-d₆, δ): 0.90–1.10 (2H, m), 1.30–1.73 (8H, m), 1.85–1.98 (1H, m), 2.20–2.49 (3H, m), 2.65–2.86 (2H, m), 2.94–3.06 (1H, m), 3.27–3.38 (1H, m), 3.69–3.84 and 4.34–4.42 (total 2H, m), 3.95–4.02 (2H, m), 5.06 (2H, s), 7.27–7.41 (5H, m), 12.38 (1H, s)

Mass (m/z): 403 (M⁺+1)

(3) (S)-1-[3-(1-tert-butoxycarbonyl-4-piperidyl)propionyl]-3-piperidinecarboxylic acid mp: 111–112° C.

IR (Nujol): 3100, 1720, 1680, 1620, 1600 cm⁻¹

NMR (DMSO-d₆, δ): 0.88–1.09 (2H, m), 1.38 (9H, s), 1.28–1.74 (8H, m), 1.87–2.01 (1H, m), 2.15–2.79 (6H, m), 2.94–3.08 (1H, m), 3.70–3.94 (4H, m), 12.31–12.49 (1H, br)

Mass (m/z): 269 (M⁺+1-Boc)

PREPARATION 3

(1) A mixture of ethyl 1-[2-(1-benzyloxycarbonyl-4-piperidyloxy)acetyl]-3-piperidinecarboxylate (2.06 g) and 1N NaOH aqueous solution (14.29 ml) in a solution of tetrahydrofuran (10 ml), ethanol (10 ml) and water (10 ml) was stirred for 1 hour at ambient temperature. The mixture was acidified with 10% aqueous solution of KHSO₄ and extracted with ethyl acetate. The extract was washed with water, brine and dried over MgSO₄, and evaporated in vacuo. The residue was recrystallized from diethyl ether to give 1-[2-(1-benzyloxycarbonyl-4-piperidyloxy)acetyl]-3-piperidinecarboxylic acid (1.51 g).

mp: 102–104° C.

IR (Nujol): 1720, 1690, 1615, 1600 cm⁻¹

NMR (DMSO-d₆, δ): 1.34–2.00 (8H, m), 2.23–2.50 (1H, m), 2.73–3.86 (9H, m), 4.14–4.36 (2H, m), 5.07 (2H, s), 7.28–7.42 (5H, m), 12.34–12.55 (1H, br)

Mass (m/z): 405 (M⁺+1)

The following compound was obtained according to a similar manner to that of Preparation 3 (1).

(2) 1-[3-(1-tert-butoxycarbonyl-4-piperidyl)propionyl]-3-pyrrolidinecarboxylic acid mp: 102–103° C.

IR (Nujol): 1720, 1680, 1480 cm$^{-1}$

NMR (DMSO-d$_6$, δ): 0.92–0.98 (2H, m), 1.38 (9H, s), 1.60–1.66 (2H, m), 1.94–2.08 (2H, m), 2.11–2.23 (2H, m), 2.52–2.66 (2H, m), 2.96–3.14 (1H, m), 3.33–3.68 (7H, m), 3.88–3.94 (2H, m)

PREPARATION 4

(1) To a solution of N-tert-butoxycarbonyl-o-mesyl -(L)-serine ethyl ester (5 g) in N,N-dimethylformamide (50 ml) was added sodium azide (2.09 g) under stirring at ambient temperature. After stirring at 60° C. for 3 hours, the mixture was poured into water and extracted with ethyl acetate. The extract was washed with water, brine and dried over MgSO$_4$, and evaporated in vacuo. The residue was purified by column chromatography on silica gel eluting with (n-hexane:EtOAc=7:1) to give ethyl 3-azidomethyl-2(S)-(tert-butoxycarbonyl) aminopropionate (1.5 g).

IR (Film): 3450, 2960, 2090, 1700 cm$^{-1}$

NMR (CDCl$_3$, δ): 1.31 (3H, t, J=7.1 Hz), 1.46 (9H, s), 3.73 (1H, d, J=3.6 Hz), 4.26 (2H, q, J=7.1 Hz), 4.41–4.51 (1H, m), 5.34–5.45 (1H, m)

Mass (m/z): 159 (M$^+$+1-Boc)

The following compound was obtained according to a similar manner to that of Preparation 4 (1).

(2) N-(Benzyloxycarbonyl)-3(S)-azidomethyl-3-alanine tert-butyl ester

IR (Film): 3300, 2100, 1720 cm$^{-1}$

NMR (CDCl$_3$, δ): 1.44 (9H, s), 2.51 (2H, d, J=6.0 Hz), 3.48–3.52 (2H, m), 4.08–4.18 (1H, m), 5.11 (2H, s), 5.40 (1H, br), 7.34–7.36 (5H, m)

Mass (m/z): 333 (M$^+$−1)

PREPARATION 5

(1) A mixture of ethyl 3-azido-2(S)-(tert-butoxycarbonyl) aminopropionate (0.5 g) and 10% Pd—C (0.1 g, 50% wet) in ethanol (5 ml) was hydrogenated at atmospheric pressure for 1 hour. After the catalyst was removed by filtration, the filtrate was concentrated in vacuo to give 2(S)-(tert-butoxycarbonyl)amino-β-alanine ethyl ester (0.45 g).

IR (Film): 3350, 2960, 1720, 1680, 1650 cm$^{-1}$

NMR (DMSO-d$_6$, δ): 1.17 (3H, t, J=7.4 Hz), 1.39 (9H, s), 1.30–1.85 (3H, m), 2.75–2.78 (1H, m), 3.33–3.49 (1H, m), 4.07 (2H, q, J=7.1 Hz), 6.80–6.89 and 7.11–7.23 (total 1H, m)

The following compound was obtained according to a similar manner to that of Preparation 5 (1).

(2) 2(S)-Acetylamino-o-alanine ethyl ester [α]$_D^{25}$=−35.9° (C=1.0, EtOH)

IR (Film): 1740, 1630 cm$^{-1}$

NMR (DMSO-d$_6$, δ): 1.20 (3H, t, J=7.1 Hz), 1.89 (3H, s), 2.99–3.23 (2H, m), 4.11 (2H, q, J=7.1 Hz), 4.46–4.57 (1H, m), 8.30 (2H, br), 8.63 (1H, d, J=7.68 Hz)

Mass (m/z): 175 (M$^+$+1)

PREPARATION 6

To a solution of N-tert-butoxycarbonyl-L-serine ethyl ester (8.20 g) in tetrahydrofuran (300 ml) was added triphenylphosphine (10.15 g, 387 m mol), diethyldiazocarbonate (6.09 ml, 38.7 m mol) and diphenylphosphonic acid (8.34 ml, 38.7 m mol) successively at −5° C. After stirring at room temperature for 3 hours, the mixture was poured into water and extracted with ethyl acetate. The extract was washed with water, saturated aqueous NaHCO$_3$ solution and brine, dried over MgSO$_4$ and evaporated in vacuo. The residue was purified by column chromatography on silica gel eluting with (EtOAc:n-hexane=10:90) to give ethyl 3-azido-2(S)-(tert-butoxycarbonylamino)propionate (5.0 g).

IR (Film): 3450, 2960, 2090, 1700 cm$^{-1}$

NMR (CDCl$_3$, δ): 1.31 (3H, t, J=7.1 Hz), 1.46 (9H, s), 3.73 (1H, d, J=3.6 Hz), 4.26 (2H, q, J=7.1 Hz), 4.41–4.51 (1H, m), 5.34–5.45 (1H, m)

Mass (m/z): 159 (M$^+$+1-Boc)

PREPARATION 7

To a solution of ethyl 3-azido-2(S)-(tert-butoxycarbonylamino)propionate (0.5 g) in ethyl acetate (5 ml) was added 4N HCl in ethyl acetate (5 ml) at 0° C. After stirring at room temperature for 2 hours, the mixture was evaporated in vacuo. The residue was recrystallized from diethyl ether to give ethyl 2(S)-amino-3-azidopropionate hydrochloride (0.3 g).

NMR (DMSO-d$_6$, δ) 1.25 (3H, t, J=7.1 Hz), 3.97 (2H, d, J=4.1 Hz), 4.22 (2H, q, J=7.1 Hz), 4.34 (1H, t, J=4.1 Hz)

Mass (m/z): 159 (M$^+$+1) free of compound

PREPARATION 8

(1) To a solution of 3-aminopyridine (1 g) in dichloromethane (10 ml) was added triethylamine (1.63 ml) and 3-methoxycarbonylpropionyl chloride (1.44 ml) under stirring at 0° C. After stirring at ambient temperature for 1 hour, the mixture was poured into water and extracted with dichloromethane. The extract was washed with water, saturated aqueous NaHCO$_3$ solution, water and brine, and dried over MgSO$_4$, and evaporated in vacuo. The residue was purified by column chromatography on silica gel eluting with (CHCl$_3$:MeOH=100:1), and recrystallized from diethyl ether to give N-(3-pyridyl) succinamic acid methyl ester (0.73 g).

mp: 78–79° C.

IR (Nujol): 1730, 1685, 1610 cm$^{-1}$

NMR (CDCl$_3$, δ): 2.66–2.81 (4H, m), 3.72 (3H, s), 7.22–7.29 (1H, m), 8.32 (1H, dd, J=8.3 and 1.2 Hz), 8.58 (2H, d, J=8.6 Hz)

Mass (m/z): 209 (M$^+$+1)

The following compound was obtained according to a similar manner to that of Preparation 8 (1).

(2) Ethyl 2(S)-acetylamino-3-azidopropionate

IR (Film): 3300, 2100, 1720, 1650 cm$^{-1}$

NMR (CDCl$_3$, δ): 1.32 (3H, t, J=7.1 Hz), 2.07 (3H, s), 3.69–3.85 (2H, m), 4.27 (2H, q, J=7.1 Hz), 4.70–4.77 (1H, m), 6.36 (1H, br)

Mass (m/z): 201 (M++1)

PREPARATION 9

A mixture of N-(3-pyridyl)-3(R)-(tert-butoxycarbonylamino)succinamic acid benzyl ester (4.28 g) and 10% Pd—C (0.86 g, 50% wet) in tetrahydrofuran (50 ml) was hydrogenated at atmospheric pressure for 2 hours. After the catalyst was removed by filtration, the filtrate was concentrated in vacuo. The residue was recrystallized from diethyl ether to give N-(3-pyridyl)-3 (R)-(tert-butoxycarbonylamino)succinamic acid (2.55 g).

mp: 98–100° C.

IR (Nujol): 3430, 1735, 1700, 1680 cm$^{-1}$

NMR (DMSO-d$_6$, δ): 1.39 (9H, s), 2.57–2.77 (2H, m), 3.33–3.46 (1H, m), 4.39–4.50 (1H, m), 7.27–7.38 (2H, m), 8.03–8.07 (1H, m), 8.26–8.28 (1H, m), 8.76 (1H, s), 10.28 (1H, s)

PREPARATION 10

To a suspension of N-(3-pyridyl)-3(R)-(tert-butoxycarbonylamino)succinamic acid (1 g) and sodium hydrogen carbonate (0.54 g) in N,N-dimethylformamide (5 ml) was added to a solution of ethyl bromide (1.76 g) in N,N-dimethylformamide (5 ml). After stirring at room temperature for 4 days, the mixture was poured into water and extracted with ethyl acetate. The extract was washed with water and brine, and dried over $MgSO_4$, and evaporated in vacuo. The residue was purified by column chromatography on silica gel eluting with ($CHCl_3$:MeOH=100:1) to give N-(3-pyridyl)-3(R)-(tert-butoxycarbonylamino)succinamic acid ethyl ester (0.63 g) as an oil.

IR (Film): 2980, 2940, 1715, 1675 $cm^{-1}$

NMR ($CDCl_3$, δ): 1.28 (3H, t, J=7.1 Hz), 1.49 (9H, s), 2.76 (1H, dd, J=17.2 and 6.4 Hz), 3.04 (1H, dd, J=17.2 and 4.3 Hz), 4.19 (2H, q, J=7.1 Hz), 4.60–4.72 (1H, m), 5.86–5.96 (1H, m), 7.23–7.30 (1H, m), 8.10 (1H, dq, J=8.3 and 1.1 Hz), 8.36 (1H, dd, J=4.7 and 1.4 Hz), 8.59 (1H, d, J=2.4 Hz), 8.76–8.81 (1H, br)

Mass (m/z): 338 ($M^+$+1)

PREPARATION 11

(1) A mixture of N-(3-pyridyl)-3(S)-(tert-butoxycarbonylamino)succinamic acid methyl ester (3.91 g) and 4N HCl in dioxane (3.36 ml) and $PtO_2$ (0.39 g) in methanol (40 ml) was hydrogenated at atmospheric pressure for 2 hours. After the catalyst was removed by filtration, the filtrate was concentrated in vacuo. The residue was recrystallized from diethyl ether to give N-(3-piperidyl)-3(S)-(tert-butoxycarbonylamino) succinamic acid methyl ester hydrochloride (3.67 g).

IR (Nujol): 1740, 1680, 1640 $cm^{-1}$

NMR (DMSO-$d_6$, δ): 1.38 (9H, s), 1.64–1.95 (4H, m), 2.48–2.92 (3H, m), 3.08–3.20 (2H, m), 3.60 (3H, d, J=5.1 Hz), 3.83–4.04 (2H, m), 4.20–4.43 (1H, m), 7.06–7.20 (1H, m), 8.12–8.29 (,1H, m)

Mass (m/z): 330 ($M^+$+1) free of compound

The following compounds were obtained according to a similar manner to that of Preparation 11 (1).

(2) N-(3-Piperidyl)succinamic acid methyl ester hydrochloride mp: 87–89° C.

IR (Nujol): 3300, 2920, 1720, 1640 $cm^{-1}$

NMR (DMSO-$d_6$, δ): 1.36–1.91 (5H, m), 2.34–2.40 (2H, m), 2.47–3.01 (3H, m), 3.04–3.20 (2H, m), 3.58 (3H, s), 3.84–4.02 (1H, m), 8.23 (1H, d, J=7.3 Hz), 9.05–9.20 (1H, br), 9.28–9.40 (1H, br)

Mass (m/z): 215 ($M^+$+1) free of compound (3) N-(3-Piperidyl)-2(S)-(tert-butoxycarbonylamino)-succinamic acid ethyl ester IR (Film): 3400, 1840, 1700, 1640 $cm^{-1}$ NMR (DMSO-$d_6$, δ): 1.16 (3H, t, J=7.1 Hz), 1.17–1.79 (6H, m), 1.37 (9H, s), 2.22–2.58 (2H, m), 2.71–2.93 (2H, m), 3.49–3.64 (1H, m), 4.06 (2H, q, J=7.1 Hz), 4.29 (1H, q, J=7.4 Hz), 7.04–7.10 (1H, m), 7.75 (1H, d, J=7.8 Hz)

Mass (m/z): 344 ($M^+$+1)

(4) 3-[[3-(1-tert-butoxycarbonyl-4-piperidyl)propionyl]-amino]piperidine

IR (Film): 3400, 2930, 1635 $cm^{-1}$

NMR (DMSO-$d_6$, δ): 0.85–1.04 (2H, m), 1.27–1.49 (5H, m), 1.38 (9H, s), 1.55–1.77 (5H, m), 1.99–2.40 (2H, m), 2.60–2.91 (5H, m), 3.46–3.64 (2H, m), 3.86–3.96 (2H, m), 7.63–7.67 (1H, m)

Mass (m/z): 340 ($M^+$+1)

PREPARATION 12

A mixture of N-(3-pyridyl)-3(R)-(tert-butoxycarbonylamino)succinamic acid ethyl ester (0.62 g) and $PtO_2$ (0.06 g) in acetic acid (12 ml) was hydrogenated. at atmospheric pressure for 6 hours. After the catalyst was removed by filtration, the filtrate was concentrated in vacuo. The residue was dissolved in water. The solution was adjusted to pH 10 with saturated aqueous potassium carbonate solution, and extracted with ethyl acetate. The extract was washed with water and brine, and dried over $MgSO_4$, and evaporated in vacuo to give N-(3-piperidyl)-3(R)-(tert-butoxycarbonylamino)succinamic acid ethyl ester (0.51 g) as an oil.

IR (Film): 3500, 2980, 2940, 1710, 1660 $cm^{-1}$

NMR (DMSO-$d_6$, δ): 1.17 (3H, t, J=7.1 Hz), 1.38 (9H, s), 1.32–1.70 (6H, m), 2.28–2.88 (4H, m), 3.50–3.64 (1H, br), 4.00 (2H, q, J=7.1 Hz), 4.20–4.33 (1H, m), 7.04–7.11 (1H, m), 7.59–7.63 (1H, m)

Mass (m/z): 344 ($M^+$+1)

PREPARATION 13

To a mixture of N(benzyloxycarbonyl)-3(S)-hydroxymethyl-β-alanine tert-butyl ester (3.1 g) and triethylamine (1.35 ml) in dichloromethane (25 ml) was added a solution of methanesulfonyl chloride (1.35 ml) in dichloromethane (5 ml), under ice cooling. After stirring at room temperature for 1 hour. The mixture was poured into water and extracted with dichloromethane. The extract was washed with water, brine and dried over $MgSO_4$, and evaporated in vacuo. The residue was purified by column chromatography on silica gel eluting with $CHCl_3$ to give N-(benzyloxycarbonyl)-3(S)-methanesulfonyloxymethyl)-β-alanine tert-butyl ester (3.1 g) as an colorless oil.

IR (Film): 3330, 1710 $cm^{-1}$

NMR ($CDCl_3$, δ): 1.44 (9H, s), 2.56–2.59 (2H, m), 2.74 (1H, br), 2.98 (3H, s), 4.25–4.34 (3H, m), 5.11 (2H, s), 5.44–5.48 (1H, m), 7.35–7.42 (5H, m)

PREPARATION 14

To a mixture of N-benzyloxycarbonyl(L)aspartic acid ω-tert-butyl ester (3.0 g) and triethylamine (1.55 ml) in tetrahydrofuran (30 ml) was added ethyl chlorocarbonate (1.06 ml) at −30° C. under nitrogen atmosphere. After stirring for 1 hour, the precipitate was filtered off and the filtrate was added to a solution of $NaBH_4$ (1.05 g) in tetrahydrofuran (30 ml)-water (6 ml) at 0° C. After stirring for 30 minutes, the mixture was neutralized with 10% aqueous $KHSO_4$ solution and extract with ethyl acetate. The extract was washed with water, brine and dried over $MgSO_4$, and evaporated in vacuo. The residue was purified by column chromatography on silica gel eluting with 2% (MeOH/$CHCl_3$) to give N-(benzyloxycarbonyl)-3(S)-hydroxymethyl-β-alanine tert-butyl ester (2.5 g) as an colorless oil.

IR (Film): 3320, 1700 $cm^{-1}$

NMR ($CDCl_3$, δ): 1.43 (9H, 5), 2.53–2.57 (3H, s), 3.68–3.73 (2H, m), 3.99–4.08 (1H, m), 5.10 (2H, m), 5.29–5.52 (1H, m), 7.35–7.37 (5H, m)

Mass (m/z): 310 ($M^+$+1)

PREPARATION 15

(1) A mixture of N-benzyloxycarbonyl-3(S)-hydroxymethyl-β-alanine tert-butyl ester (2.0 g), triphenylphosphine (1.87 g), imidazole (0.66 g) and $I_2$ (1–80 g) was stirred for 30 minutes at room temperature. The precipitate was filtered off and the filtrate was evaporated in vacuo. The residue was purified by column chromatography on silica gel eluting with 5% (EtOAc/n-hexane) to give N-benzyloxycarbonyl-3(S)-iodomethyl-β-alanine tert-butyl ester (1.8 g) as a white solid.

IR (Nujol): 3350, 1700 cm$^{-1}$

NMR (CDCl$_3$, δ): 1.44 (9H, s), 2.48–2.64 (2H, m), 3.41–3.43 (2H, m), 3.91–3.98 (1H, m), 5.11 (2H, s), 5.30–5.35 (1H, m), 7.35–3.37 (5H, m)

The following compound was obtained according to a similar manner to that of Preparation 15 (1).

(2) N-(Benzyloxycarbonyl)-3(S)-(n-butanesulfonyl)-aminomethyl)-β-alanine tert-butyl ester IR (CHCl$_3$): 1710 cm$^{-1}$ NMR (CDCl$_3$, δ): 0.93 (3H, t, J=7.2 Hz), 1.43 (9H, s), 1.66–1.83 (4H, m), 2.54 (2H, d, J=6.0 Hz), 2.95–3.03 (2H, m), 3.26–3.32 (2H, m), 4.00–4.10 (1H, m), 4.84–4.92 (1H, m), 5.10 (2H, s), 5.60–5.61 (1H, m), 7.35–7.37 (5H, m)

Mass (m/z): 429 (M$^+$+1)

PREPARATION 16

To a solution of thiophenol (0.15 ml) in N,N-dimethylformamide (6 ml) was added NaH (58 mg) under ice cooling. After stirring at room temperature for 30 minutes, N-(benzyloxycarbonyl)-3(S)-iodomethy-β-alanine tert-butyl ester (0.6 g) was added and stirred for additional 1 hour. The mixture was poured into water and extracted with ethyl acetate. The extract was washed with water, brine and dried over MgSO$_4$, and evaporated in vacuo. The residue was purified by column chromatography on silica gel eluting with 5% (EtOAc/n-hexane) to give N-(benzyloxycarbonyl)-3(S)-phenylthiomethy-β-alanine tert-butyl ester (0.64 g) as an pale yellow oil.

IR (Film): 3320, 1720 cm$^{-1}$

NMR (CDCl$_3$, δ): 1.41 (9H, s), 2.50–2.66 (2H, m), 3.02–3.25 (2H, m), 4.10–4.38 (1H, m), 5.08 (2H, s), 5.45–5.50 (1H, m), 7.18–7.38 (10H, m)

Mass (m/z): 402 (M$^+$+1)

PREPARATION 17

To a solution of N-(benzyloxycarbonyl)-3(S)-phenylthiomethy-β-alanine tert-butyl ester (0.60 g) in chloroform (10 ml) was added m-chloroperbenzoic acid (0.64 g) at 0° C. After stirring at room temperature for 2 hours, the mixture was poured into saturated aqueous NaHCO$_3$ solution and extracted with chloroform. The extract was washed with aqueous NaHSO$_3$ solution, water, brine and dried over MgSO$_4$, and evaporated in vacuo to give N-(benzyloxycarbonyl)-3(S)-phenylsulfonylmethy-β-alanine tert-butyl ester (0.4 g) as a colorless oil.

IR (Film): 3350, 1720, 1520 cm$^{-1}$

NMR (CDCl$_3$, δ): 1.42 (9H, s), 2.64–2.79 (2H, m), 3.36–3.46 (1H, m), 3.58–4.61 (1H, m), 4.33–4.37 (1H, m), 5.02 (2H, s), 5.37–5.65 (1H, m), 7.33–7.36 (5H, m), 7.49–7.64 (3H, m), 7.88–7.92 (2H, m)

Mass (m/z): 434 (M$^+$+1)

PREPARATION 18

(1) A mixture of N-(benzyloxycarbonyl)-3(S)-phenylsulfonylmethy-β-alanine tert-butyl ester (0.44 g) and 10% Pd—C (0.1 g, 50% wet) in acetic acid (5 ml) was hydrogenated at 1 atmospheric pressure of hydrogen for 1 hour. The catalyst was filtered off and the filtrate was evaporated in vacuo. The residue was dissolved in ethyl acetate and washed with saturated aqueous NaHCO$_3$ solution. The organic layer was dried over MgSO$_4$ and evaporated in vacuo to give 3(S)-phenylsulfonylmethy-βalanine tert-butyl ester (0.3 g) as a colorless oil.

IR (Film): 3570, 3370, 1710 cm$^{-1}$

NMR (CDCl$_3$, δ): 1.42 (9H, s), 2.31–2.52 (2H, m), 3.21–3.30 (2H, m), 3.68–3.78 (1H, m), 7.54–7.72 (3H, m), 7.91–7.96 (2H, m)

Mass (m/z): 300 (M$^+$+1)

The following compound was obtained according to a similar manner to that of Preparation 18 (1).

(2) 3(S)-(n-butanesulfonylamino)methy-β-alanine tert-butyl ester

NMR (DMSO-d$_6$, δ): 0.89 (3H, t, J=7.2 Hz), 1.40 (9H, s), 1.54–2.13 (4H, m), 2.31–2.41 (1H, m), 2.81–2.87 (2H, m), 2.94–3.02 (4H, m)

Mass (m/z): 295 (M$^+$+1)

PREPARATION 19

To a solution of N-[(R)-(1-benzyloxycarbonyl-3-piperidyl)carbonyl]-2(S)-(tert-butoxycarbonylamino)-β-alanine ethyl ester (0.4 g) in ethyl acetate (4 ml) was added 4N HCl in ethyl acetate (2.1 ml) under stirring at 0° C. After stirring at ambient temperature for 2 hours, the resulting precipitates were collected by filtration to give N-[(R)-1-benzyloxycarbonyl-3-piperidyl)carbonyl]-2(S)-amino-β-alanine ethyl ester hydrochloride (0.31 g).

IR (Nujol): 3300, 1735, 1680, 1640 cm$^{-1}$

NMR (DMSO-d$_6$, δ): 1.02–1.91 (7H, m), 2.21–2.35 (1H, m), 2.80–2.89 (2H, m), 3.42–3.67 (2H, m), 3.90– 4.15 (5H, m), 5.07 (2H, d, J=2.7 Hz), 7.28–7.42 (5H, m), 8.43–8.49 (1H, m), 8.64–8.73 (2H, br)

Mass (m/z): 378 (M$^+$+1) free of compound

PREPARATION 20

A solution of N-[(R)-(1-benzyloxycarbonyl-3-piperidyl) carbonyl]-2(S)-amino-β-alanine ethyl ester hydrochloride (300 mg) in dichloromethane (3 ml) was added triethylamine (222 μl) and benzoyl chloride (93 μl) under stirring at 0° C. After stirring at ambient temperature for 1 hour, the mixture was poured into water and extracted with dichloromethane. The extract was washed with water, saturated aqueous NaHCO$_3$ solution, water and brine, and dried over MgSO$_4$, and evaporated in vacuo. The residue was recrystallized from diethyl ether to give N-[(R)-(1-benzyloxycarbonyl-3-piperidyl)carbonyl]-2(S)-benzoylamino-β-alanine ethyl ester (349 mg).

mp: 135° C.

IR (Nujol): 3290, 1730, 1685, 1655, 1640 cm$^{-1}$

NMR (CDCl$_3$, δ): 1.30 (3H, t, J=7.1 Hz), 1.33–2.10 (6H, m), 2.26–2.43 (1H, m), 3.26–4.03 (5H, m), 4.14–4.30 (2H, m), 4.78–4.89 (1H, m), 5.10 (2H, d, J=3.9 Hz), 7.24–7.55 (10H, m), 7.85–7.95 (1H, m)

Mass (m/z): 482 (M$^+$+1)

PREPARATION 21

(1) A solution of N-[(1R)-(1-benzyloxycarbonyl-3-piperidyl)carbonyl]-2(S)-amino-β-alanine hydrochloride in water was made basic with aqueous K$_2$CO$_3$ solution, and extracted with ethyl acetate. The extract was dried over MgSO$_4$, and evaporated in vacuo. The residue (198 mg) was dissolved in ethyl acetate (5 ml), and added NaHCO$_3$ (269 mg) and benzenesulfonyl chloride (136 μl). The mixture was refluxed for 4 hours. After the insoluble material was removed by filtration, the filtrate was concentrated in vacuo. The residue was purified by column chromatography on silica gel eluting with (CHCl$_3$:MeOH=100:1) to give N-[(R)-1-benzyloxycarbonyl-3-piperidyl)carbonyl]-2(S)-phenylsulfonylamino-β-alanine ethyl ester as an oil (255 mg).

IR (Film): 1720, 1640 cm$^{-1}$

NMR (CDCl$_3$, δ): 1.12 (3H, t, J=7.1 Hz), 1.40–2.11 (7H, m), 2.23–2.50 (1H, m), 3.33–3.83 (3H, m), 3.98 (2H, q, J=7.1 Hz), 3.93–4.19 (1H, m), 5.16 (2H, q, J=10.1 Hz), 7.31–7.40 (10H, m), 7.81–7.86 (2H, m)

Mass (m/z): 518 (M$^+$+1)

The following compound was obtained according to a similar manner to that of Preparation 21 (1).

(2) N-[(R)-(1-benzyloxycarbonyl-3-piperidyl)carbonyl]-2 (S)-(n-butanesulfonylamino)-β-alanine ethyl ester IR (Film): 2940, 2860, 1730, 1665 cm$^{-1}$ NMR (CDCl$_3$, δ): 0.93 (3H, t, J=7.3 Hz), 1.31 (3H, t, J=7.2 Hz), 1.37–1.48 (4H, m), 1.56–1.84 (7H, m), 1.91–2.43 (1H, m), 2.97–3.05 (2H, m), 3.35–3.87 (4H, m), 4.15–4.31 (3H, m), 5.10–5.25 (2H, m), 5.82–6.01 (1/2H, m), 6.63–6.83 (1/2H, m), 7.33–7.37 (5H, m)

Mass (m/z): 498 (M$^+$+1)

PREPARATION 22

To a solution of trimethylsilylacetylene (1715 ml) in tetrahydrofuran (18.0 l) was added ethyl magnesium chloride (2.0M solution in tetrahydrofuran; 6.19 l) was added dropwise below −30° C. under nitrogen atmosphere. The reaction mixture was allowed to 0° C. and stirred for 1 hour. After cooling to −30° C., 4-acetoxy-2-azetidinone (320 g) was added and warmed to room temperature, and stirred for 2 hours. After cooling to −20° C., saturated ammonium chloride (4.0 l) was added. Ethyl acetate (20 l) was added and washed with water (10 l×2) and brine. The organic layer was dried over magnesium sulfate, filtered off and evaporated in vacuo to give 4-(2-trimethylsilylethynyl)-2-azetidinone (425 g), which was essentially pure, so it was used to the next step without further purification.

IR (Nujol): 3150, 2130, 1740, 1330, 1240, 1090, 1060, 950, 840, 750, 740 cm$^{-1}$ NMR (CDCl$_3$, δ): 0.16 (9H, s), 3.02 (1H, ddd, J=14.7 and 2.7 and 1.6 Hz), 3.30 (1H, ddd, J=14.7 and 5.3 and 1.8 Hz), 4.24 (1H, dd, J=5.3 and 2.7 Hz), 6.41 (1H, br)

PREPARATION 23

4-(2-Trimethylsilylethynyl)-2-azetidinone (485 g) and paraformaldehyde (261 g) was heated at 135° C. for 45 minutes. The resulting mixture was cooled to room temperature and purified with column chromatography on silica gel (CH$_2$Cl$_2$: EtOAc=8:2) to give N-hydroxymethyl-4-(2-trimethylsilylethynyl)-2-azetidinone (429 g).

IR (Nujol): 3300, 1710, 1280, 1230, 1020, 820 cm$^1$

NMR (CDCl$_3$, δ): 0.18 (9H, s), 3.02 (1H, dd, J=14.8 and 2.7 Hz), 3.26 (1H, dd, J=14.8 and 5.4 Hz), 3.69 (1H, dd, J=9.4 and 5.3 Hz), 4.41 (2H, m), 5.01 (1H, dd, J=11.8 and 5.2 Hz)

FAB-Mass: 197 (M$^+$+1)

PREPARATION 24

To a solution of N-hydroxymethyl-4-(2-trimethylsilylethynyl)-2azetidinone (250 g) in dichloromethane (6.5 L) was added vinyl acetate (350 ml) and Lipase PS (trademark; Amano Pharmaceutical Co., Ltd.) (190 g). The mixture was warmed to 37° C. and stirred for 32 hours. Catalyst was filtered off and washed with dichloromethane. Solvent was evaporated in vacuo. The residue was subjected to silica gel column chromatography eluting with (n-hexane:EtOAc=8:2 to 0:1) to give (R)-N-hydroxymethyl-4-(2-trimethylsilylethynyl)-2-azetidinone (192 g).

[α]$_D^{20}$=−133.9° (C=1.12, CHCl$_3$)

IR (Nujol): 3300, 1710, 1280, 1230, 1020, 820 cm$^{-1}$

NMR (CDCl$_3$, δ): 0.18 (9H, s), 3.02 (1H, dd, J=14.8 and 2.7 Hz), 3.26 (1H, dd, J=14.8 and 5.4 Hz), 3.69 (1H, dd, J=9.4 and 5.3 Hz), 4.41 (2H, m), 5.01 (1H, dd, J=11.8 and 5.2 Hz)

FAB-Mass: 197.8 (M$^+$)

PREPARATION 25

To aqueous ammonia (300 ml) and methanol (1000 ml) was added (S)-N-hydroxymethy-4-(2-trimethylsilylethynyl)-2-azetidinone (101 g). The resulting mixture was stirred at room temperature for overnight. Solvent was evaporated in vacuo and the residue was added ethyl acetate (1.5 l) and washed with water (100 ml×3) and brine. The organic layer was dried over MgSO$_4$, filtered off and evaporated in vacuo. The residue was purified by column chromatography on silica gel eluting with (CH$_2$Cl$_2$: EtOAc=9:1) to (S)-4-ethynyl-2-azetidinone (29.8 g).

[α]$_D^{20}$=−63.3° (C=1.09, CHCl$_3$)

IR (Nujol): 3200, 2080, 1400, 1320, 1160 cm$^{-1}$

NMR (CDCl$_3$, δ): 2.46 (1H, d, J=2.1 Hz), 3.11 (1H, ddd, J=14.8 and 2.5 and 1.6 Hz), 3.35 (1H, ddd, J=14.8 and 5.3 and 1.8 Hz), 4.27 (1H, m), 6.46 (1H, br)

PREPARATION 26

To a solution of (s)-4-ethynyl-2-azetidinone (28.5 g) in ethanol (140 ml) was added a solution of HCl in ethanol (5.86N) below 10° C., and stirred for 1 hour at room temperature. The mixture was evaporated in vacuo. The residue was washed with diethyl ether and collected by filtration to give ethyl (S)-3-amino-4-pentynoate hydrochloride (50.3 g) as white crystal. The ratio of enantiomers was determined to be 98.5:1.5 by chiral HPLC using CROWN-PAK CR(+) (trademark; DAICEL CHEMICAL INDUSTRIES, LTD.).

[α]$_D^{20}$=−6.27° (C=1.11, MeOH)

IR (Nujol): 3210, 2190, 1710, 1560 cm$^{-1}$

NMR (DMSO-d$_6$, δ): 1.21 (3H, t, J=7.1 Hz), 2.84 (1H, dd, J=16.1 and 9.1 Hz), 3.07 (1H, dd, J=16.1 and 5.0 Hz), 4.13 (2H, q, J=7.1 Hz), 4.29 (1H, m), 8.94 (3H, br)

Mass (m/z): 142 (M$^+$+1)

PREPARATION 27

To a solution of CBr$_4$ (3.11 g) in dichloromethane (15 ml) was added dropwise a solution of triphenylphosphine (4.92 g) in dichloromethane (15 ml) at 0° C. After stirring for 10 minutes a solution of (S)-N-tert-butyldimethylsilyl-4-formyl-2-azetidinone (1.0 g) in dichloromethane (10 ml) was added dropwise at 0° C. and stirred for 20 minutes. The mixture was poured into saturated aqueous NaHCO$_3$ solution and extracted with dichloromethane. The extract was washed with water, dried over MgSO$_4$ and evaporated in vacuo. The residue was purified by chromatography on silica gel eluting with (diethyl ether:n-hexane=1:5) to give (S)-N-tert-butyldimethylsilyl-4-(2,2dibromoethenyl)-2-azetidinone (0.83 g) as a pale yellow oil.

IR (Film): 3450, 3300, 1740, 1600 cm$^{-1}$

NMR (CDCl$_3$, δ): 0.12 (3H, s), 0.16 (3H, s), 0.85 (9H, s), 2.75 (1H, dd, J=2.8 and 15.6 Hz), 3.30 (1H, dd, J=5.6 and 15.6 Hz), 4.13–4.22 (1H, m), 6.38 (1H, d, J=8.8 Hz)

Mass (m/z): 370 (M$^+$+1)

PREPARATION 28

To a solution of (s)-N-tert-butyldimethylsilyl-4 (2,2-dibromoethenyl)-2-azetidinone (0.63 g) was added lithium bis(trimethylsilyl)amide (3.75 ml, 1 mol solution in n-hexane) at −75° C. After stirring at −75° C. for 1 hour, a saturated aqueous NH₄Cl solution was added and extracted with ethyl acetate. The extract was washed with water and brine, dried over MgSO₄, and evaporated in vacuo. The residue was purified by chromatography on silica gel eluting with (diethyl ether:n-hexane=1:5) to give (S)-N-tert-butyldimethylsilyl-4-ethynyl-2-azetidinone (0.20 g) as an colorless oil.

$[\alpha]_D^{20}$=−61.5° (C=1.0, MeOH)

IR (Film): 3420, 3250, 2100, 1720 cm$^{-1}$

NMR (CDCl₃, δ): 0.19 (6H, s), 0.88 (9H, s), 2.35 (1H, d, J=2.2 Hz), 3.02 (1H, dd, J=3.0 and 15.1 Hz), 3.28 (1H, dd, J=5.6 and 15.1 Hz), 4.00–4.05 (1H, m)

Mass (m/z): 210 (M⁺+1)

PREPARATION 29

To a solution of (S)-N-tert-butyldimethylsilyl-4-ethynyl-2-azetidinone (120 mg) was added 4N HCl in ethanol (2 ml) at room temperature. After stirring for 1 hour, the mixture was evaporated in vacuo. The residue was recrystallized from diethyl ether to give ethyl (S)-3-amino-4-pentynoate hydrochloride (50 ml) as a white solid. The ratio of enantiomers was determined to be 99.5:0.5 by chiral HPLC using CROWNPAK CR(+).

$[\alpha]_D^{20}$=−7.1° (C=1.0, MeOH)

IR (Nujol): 3210, 2190, 1710, 1560 cm$^{-1}$

NMR (DMSO-d₆, δ): 1.21 (3H, t, J=7.1 Hz), 2.84 (1H, dd, J=16.1 and 9.1 Hz), 3.07 (1H, dd, J=16.1 and 5.1 Hz), 4.13 (2H, q, J=7.1 Hz), 4.29 (1H, m), 8.94 (3H, br)

Mass (m/z): 142 (M⁺+1)

PREPARATION 30

To a mixture of zinc (11.9 g) in tetrahydrofuran (215 ml) was added titanium (IV) isopropoxide (6.0 ml) at ambient temperature and the resultant mixture was stirred for 1 hour. A solution of methyleneiodide (8.1 ml) was then added to the mixture was stirred for 30 minutes. To the resultant mixture was added dropwise a solution of (S)-N-tert-butyldimethylsilyl-4-formyl-2-azetidinone (4.3 g) in tetrahydrofuran (130 ml) and stirred for 2 hours. The mixture was poured into a mixture of diethyl ether (500 ml) and 1N HCl (300 ml). The organic layer was washed with water, saturated aqueous NaHCO₃ solution and brine, dried over MgSO₄, and evaporated in vacuo. The residue was purified by chromatograph on silica gel eluting with (EtOAc:n-hexane=1:10) to give (S)-N-tert-butyldimethylsilyl-4-vinyl-2-azetidinone (2.13 g) as a colorless oil.

$[\alpha]_D^{20}$=−15.6° (C=1.0, MeOH)

IR (Film): 2940, 2860, 1730 cm$^{-1}$

NMR (CDCl₃, δ): 0.17 (3H, s), 0.19 (3H, s), 0.96 (9H, s), 2.77 (1H, dd, J=2.8 and 14.7 Hz), 3.30 (1H, dd, J=5.6 and 14.7 Hz), 3.97–4.06 (1H, m), 5.15–5.13 (2H, m), 5.58–5.76 (1H, m)

Mass (m/z): 212 (M⁺+1)

PREPARATION 31

To a solution of (S)-N-tert-butyldimethylsilyl-4-vinyl-2-azetidinone (1.0 g) in ethanol (5 ml) was added 6N HCl in ethanol (5 ml) at 0° C. After stirring for 1 hour, the mixture was evaporated in vacuo and the resultant solid was washed with diethyl ether to give ethyl (S)-3-amino-4-pentenoate hydrochloride (0.67 g) as a white solid.

$[\alpha]_D^{20}$=−8.9° (C=1.0, MeOH)

IR (Nujol): 3420, 2100, 1720, 1600 cm$^{-1}$

NMR (DMSO-d₆, δ): 1.19 (3H, t, J=7.1 Hz), 2.70 (1H, dd, J=8.4 and 16.0 Hz), 2.91 (1H, dd, J=5.7 and 16.0 Hz), 3.93–4.00 (1H, m), 4.05 (2H, q, J=7.1 Hz), 5.31 (1H, d, J=8.1 Hz), 5.38 (1H, d, J=15.0 Hz), 5.80–5.97 (1H, m), 8.54 (3H, br)

Elemental Analysis C₇H₁₃NO₂HCl.0.2C₂H₅OH Calcd.: C, 47.11; H, 8.01; N, 7.42 Found: C, 47.26; H, 8.37; N, 7.79

EXAMPLE 1

(1) To a mixture of ethyl 3-amino-2-ethynylpropionate hydrochloride (0.5 g), (R)-1-[3-(1-tert-butoxycarbonyl-4-piperidyl)propionyl]-3-piperidinecarboxylic acid (1.04 g) and 1-hydroxybenztriazole (0.38 g) in N,N-dimethylformamide (5 ml) was added 1-ethyl-3-(3-dimethylaminopropyl)carbodiimide (0.51 ml) under stirring at 0° C. After stirring at ambient temperature overnight, the mixture was poured into water and extracted with ethyl acetate. The extract was washed with water, brine and dried over MgSO₄, and evaporated in vacuo. The residue was purified by chromatography on silica gel eluting with CHCl₃:MeOH=(100:1) to give N-[(R)-1-{3-(1-tert-butoxycarbonyl-4-piperidyl)propionyl}-3-piperidylcarbonyl]-3-ethynyl-β-alanine ethyl ester as an oil (1.38 g).

IR (Film): 3440, 3270, 2960, 2920, 2850, 1720, 1710, 1640 cm$^{-1}$

NMR (CDCl₃, δ): 0.98–1.20 (1H, m), 1.28 (3H, t, J=7.1 Hz), 1.45 (9H, s), 1.45–1.78 (8H, m), 1.89–2.07 (2H, m), 2.26–2.39 (4H, m), 2.61–2.74 (4H, m), 3.20–3.34 (2H, m), 3.53–3.69 and 3.82–3.97 (total 1H, m), 4.02–4.50 (5H, m), 5.03–5.18 (2H, m), 6.80–6.90 and 7.06–7.16 (total 1H, m)

Mass (m/z): 492 (M⁺+1)

The following compounds were obtained according to a similar manner to that of Example 1 (1).

(2) (3R)-N-[(R)-1-{3-(1-tert-butoxycarbonyl-4 piperidyl)propionyl}-3-piperidylcarbonyl]-3-methyl-β-alanine methyl ester IR (Film): 3350, 2930, 2930, 2860, 1710, 1620 cm$^{-1}$ NMR (CDCl₃, δ): 1.02–1.15 (2H, m), 1.22 (3H, d, J=6.8 Hz), 1.45 (9H, s), 1.34–1.79 (9H, m), 1.99–2.16 (2H, m), 2.05–2.73 (7H, m), 3.18–3.58 (2H, m), 3.67–3.70 (3H, m), 3.85–4.14 (3H, m), 4.29–4.49 (1H, m), 6.32–6.43 and 6.69–6.79 (total 1H, Mass (m/z): 468 (M⁺+1)

(3) N-[(R)-1-{3-(1-tert-butoxycarbonyl-4-piperidyl)-propionyl}-3-piperidylcarbonyl]-β-alanine ethyl ester IR (Film): 3420, 3300, 2920, 2850, 1725, 1665, 1630 cm$^{-1}$ NMR (CDCl₃, δ): 1.00–1.21 (2H, m), 1.27 (3H, t, J=7.1 Hz), 1.45 (9H, m), 1.52–1.77 (7H, m), 1.83–2.09 (2H, m), 2.17–2.39 (3H, m), 2.48–2.73 (4H, m), 3.16–3.68 and 3.83–3.96 (total 5H, m), 4.02–4.25 and 4.36–4.99 (total 3H, m), 4.16 (2H, q, J=7.2 Hz), 6.23–6.26 and 6.55–6.66 (total 1H, m)

Mass (m/z): 468 (M⁺+1)

(4) N-[1-{2-(1-benzyloxycarbonyl-4-piperidyloxy)acetyl}-3-piperidylcarbonyl]-β-alanine methyl ester IR (Film): 3320, 3000, 2940, 2860, 1730, 1640 cm$^{-1}$ NMR (CDCl₃, δ): 1.40–2.01 (9H, m), 2.21–2.36 (1H, m), 2.53 (2H, t, J=5.9 Hz), 3.13–3.34 (3H, m), 3.48–3.61 (3H, m), 3.70 (3H, s), 3.97–4.00 (3H, m), 4.11–4.41 (3H, m), 5.12 (2H, s), 6.20–6.30 (3H, m), 6.42–6.51 (total 1H, m), 7.30–7.37 (5H, m)

Mass (m/z): 490 (M⁺+1)

(5) N-[(R)-1-{3-(1-tert-butoxycarbonyl-4-piperidyl)-propionyl}-3-piperidylcarbonyl]-3(S)-(4-methoxyphenethyl)aminocarbonyl-β-alanine benzyl ester mp: 143° C.

IR (Nujol): 3280, 1735, 1680, 1635 cm$^{-1}$

NMR (CDCl$_3$, δ): 0.98–1.26 (3H, m), 1.34–1.84 (9H, m), 1.45 (9H, s), 2.19–2.36 (3H, m), 2.52–2.82 (6H, m), 3.01–3.28 (1H, m), 3.39–3.64 (3H, m), 3.78 (3H, s), 4.01–4.44 (3H, m), 4.76–4.86 (1H, m), 5.17 (2H, s), 5.64–5.72 (1/3H, m), 6.00–6.07 (2/3H, m), 6.83 (2H, d, J=8.6 Hz), 6.86–7.20 (3H, m), 7.34 (5H, s)

Mass (m/z): 607 (M$^+$+1-Boc)

(6) N-[(R)-1-{3-(1-tert-butoxycarbonyl-4-piperidyl)propionyl}-3-piperidylcarbonyl]-3(R)-phenethyl-β-alanine ethyl ester IR (Film): 3450, 3310, 2980, 2930, 2860, 1720, 1640 cm$^{-1}$ NMR (CDCl$_3$, δ): 1.01–1.20 (2H, m), 1.22–1.30 (3H, m), 1.45 (9H, s), 1.45–2.05 (13H, m), 2.28–2.72 (8H, m), 3.16–3.59 (2H, m), 3.91–4.48 (4H, m), 4.11 (2H, q, J=7.1 Hz), 6.40 (1/3H, d, J=9.1 Hz), 6.76 (2/3H, d, J=8.8 Hz), 7.16–7.31 (5H, m)

Mass (m/z): 572 (M$^+$+1)

(7) N-[(R)-1-{3-(1-tert-butoxycarbonyl-4-piperidyl)propionyl}-3-piperidylcarbonyl]-β-alanine benzyl ester IR (Film): 2910, 2840, 1720, 1630 cm$^{-1}$ NMR (CDCl$_3$, δ): 1.01–1.22 (3H, m), 1.45 (9H, s), 1.33–2.00 (6H, m), 2.18–2.35 (3H, m), 2.54–2.73 (5H, m), 3.15–3.32 (2H, m), 3.45–3.65 (3H, m), 3.81–3.95 (1/2H, m), 4.02–4.19 (3H, m), 4.35–4.49 (1/2H, m), 5.14 (2H, s), 6.12–6.25 (1/3H, m), 6.54–6.63 (2/3H, m), 7.36 (5H, s)

Mass (m/z): 530 (M$^+$+1)

(8) N-[(R)-1-{3-(1-tert-butoxycarbonyl-4-piperidyl)propionyl}-3-piperidylcarbonyl]-β-alanine 1-cyclohexyloxycarbonyloxy)ethyl ester IR (Film): 2920, 2850, 1740, 1630 cm$^{-1}$ NMR (DMSO-d$_6$, δ): 1.00–1.83 (13H, m), 1.45 (9H, s), 1.53 (3H, d, J=5.5 Hz), 1.89–2.08 (5H, m), 2.02–2.44 (4H, m), 2.52–2.73 (5H, m), 3.11–3.29 (2H, m), 3.39–3.72 (3H, m), 3.88–4.31 (4H, m), 3.87–4.48 (1H, m), 6.30–6.40 (1/3H, m), 6.60–6.69 (2/3H, m), 6.72–6.77 (1H, m)

Mass (m/z): 610 (M$^+$+1)

(9) N-[(R)-1-{3-(1-tert-butoxycarbonyl-4-piperidyl)propionyl}-3-piperidylcarbonyl]-3(S)-phenylsulfonylmethyl-β-alanine tert-butyl ester IR (Film): 3300, 1720, 1660, 1620 cm$^{-1}$ NMR (CDCl$_3$, δ): 1.08–1.14 (2H, m), 1.42 (9H, s), 1.45 (9H, s), 1.52–1.87 (8H, m), 2.20–2.36 (3H, m), 2.67–2.72 (4H, m), 3.27–3.38 (3H, m), 3.60–3.70 (2H, m), 3.86–4.15 (3H, m), 4.48–4.60 (2H, m), 7.58–7.62 (3H, m), 7.90–7.94 (2H, m)

Mass (m/z): 650 (M$^+$+1)

(10) N-[(R)-1-{3-(1-tert-butoxycarbonyl-4-piperidyl)propionyl}-3-piperidylcarbonyl]-3 (S)-(n-butanesulfonylaminomethyl)-β-alanine tert-butyl ester IR (Film): 3280, 1720, 1650, 1620 cm$^{-1}$ NMR (CDCl$_3$, δ): 0.95 (3H, t, J=7.2 Hz), 1.18–1.20 (2H, m), 1.45 (18H, s), 1.50–2.10 (15H, m), 2.36–2.40 (3H, m), 2.48–2.72 (4H, m), 2.89–3.05 (3H, m), 3.28–3.35 (2H, m), 3.42–3.55 (1H, m), 3.98–4.24 (3H, m), 4.90–5.10 (1H, m)

Mass (m/z): 645 (M$^+$1)

(11) N-(R)-1-{3-(1-tert-butoxycarbonyl-4-piperidyl)propionyl}-3-piperidylcarbonyl]-3(R)-(4-methoxyphenethyl)-β-alanine methyl ester IR (Film): 2930, 2860, 1730, 1630 cm$^{-1}$ NMR (CDCl$_3$, δ): 1.02–1.21 (2H, m), 1.45 (9H, s), 1.53–1.89 (10H, m), 2.00–2.23 (1H, m), 2.29–2.73 (9H, m), 3.16–3.59 (3H, m), 3.66 (3H, s), 3.78 (3H, s), 3.91 (1H, dd, J=13.8 and 3.6 Hz), 4.08 (2H, d, J=12.7 Hz), 4.23–4.37 (1H, m), 6.72–6.80 (1H, m), 6.82 (2H, d, J=8.6 Hz), 7.09 (2H, d, J=8.6 Hz)

Mass (m/z): 588 (M$^+$+1)

(12) Ethyl [N-[(R)-1-{3-(1-tert-butoxycarbonyl-4-piperidyl)propionyl}-3-piperidylcarbonyl]-2-piperidyl]acetate IR (Film): 2980, 2930, 2860, 1720, 1675, 1625 cm$^{-1}$ NMR (CDCl$_3$, δ): 1.00–1.30 (4H, m), 1.45 (9H, s), 1.53–1.87 (14H, m), 2.31–3.28 (11H, m), 3.61–3.89 (2H, m), 4.03–4.16 (4H, m), 4.50–4.69 (2H, m), 4.69–4.75 (1/3H, m), 5.13–5.28 (2/3H, m)

Mass (m/z): 522 (M$^+$+1)

(13) N-[4-{3-(1-tert-butoxycarbonyl-4-piperidyl)propionyl}-2-morpholinylcarbonyl]-β-alanine ethyl ester IR (Film): 2910, 2850, 1720, 1600 cm$^{-1}$ NMR (CDCl$_3$, δ): 1.01–1.21 (1H, m), 1.28 (3H, t, J=7.1 Hz), 1.45 (9H, m), 1.45–1.73 (6H, m), 2.30–2.47 (2H, m), 2.52–2.93 (5H, m), 3.04–3.16 (1H, m), 3.49–3.62 (3H, m), 3.86–4.38 (6H, m), 4.18 (2H, q, J=7.2 Hz), 7.09–7.19 (1H, m)

Mass (m/z): 470 (M$^+$+1)

(14) N-[(R)-1-{3-(1-tert-butoxycarbonyl-4-piperidyl)propionyl}-3-piperidylcarbonyl]-3-phenyl-β-alanine methyl ester IR (Film): 2940, 2860, 1735, 1630 cm$^{-1}$ NMR (CDCl$_3$, δ): 0.99–1.24 (2H, m), 1.45 (9H, s), 1.45–1.89 (9H, m), 2.00–2.16 (1H, m), 2.25–2.44 (3H, m), 2.61–2.96 (4H, m), 3.19–3.55 (2H, m), 3.55 (3H, s), 3.62–4.48 (4H, m), 5.37–5.47 (1H, m), 7.28–7.35 (5H, m)

Mass (m/z): 530 (M$^+$+1)

(15) N-[(R)-1-{3-(1-tert-butoxycarbonyl-4-piperidyl)propionyl}-3-piperidylcarbonyl]-3(R)-(3,4-dimethoxyphenethyl)-β-alanine methyl ester IR (Film): 3290, 2980, 2925, 2850, 1720, 1650, 1620 cm$^{-1}$ NMR (CDCl$_3$, δ): 1.02–1.23 (3H, m), 1.45 (9H, s), 1.45–1.94 (9H, m), 2.03–2.73 (11H, m), 3.18–3.67 (3H, m), 3.66 (3H, s), 3.85 (3H, s), 3.88 (3H, s), 3.92–4.11 (2H, m), 4.23–4.47 (1H, m), 6.69–6.81 (4H, m)

Mass (m/z): 618 (M$^+$+1)

(16) N-[(R)-1-{3-(1-tert-butoxycarbonyl-4-piperidyl)propionyl}-3-piperidylcarbonyl]-3(S)-hydroxymethyl-β-alanine tert-butyl ester NMR (CDCl$_3$, δ): 1.08–1.18 (3H, m), 1.45 (18H, s), 1.56–1.99 (8H, m), 2.32–2.36 (3H, m), 2.50–2.73 (4H, m), 3.00–3.33 (2H, m), 3.52–3.62 (1H, m), 3.69 (3H, t, J=5.2 Hz), 4.04–4.20 (4H, m), 6.92 and 7.27 (total 1H, br)

(17) N-[(R)-1-{3-(1-tert-butoxycarbonyl-4-piperidyl)propionyl}-3-piperidylcarbonyl]-3(R)-(3-methoxyphenethyl)-β-alanine methyl ester IR (Film): 3280, 1640, 1420, 1240, 1150, 860, 740, 680 cm$^{-1}$ NMR (DMSO-d$_6$, δ): 0.80–1.15 (6H, m), 1.38 (9H, s), 1.50–1.96 (6H, m), 2.02–3.10 (16H, m), 3.55 (3H, s), 3.72 (3H, s), 3.95 (2H, m), 4.08–4.22 (1H, m), 6.73 (3H, m), 7.17 (1H, m), 7.84 (1H, m), 8.31 (1H, s)

Mass (m/z): 588 (M$^+$+1)

(18) N-[(R)-1-{3-(1-tert-butoxycarbonyl-4-piperidyl)propionyl}-3-piperidylcarbonyl]-3(R)-[2-(3-indolyl)ethyl]-β-alanine methyl ester IR (Film): 3450, 1710, 1660, 1610 cm$^{-1}$ NMR (CDCl$_3$, δ): 1.08–1.14 (1H, m), 1.42 (9H, s), 1.45–2.24 (18H, m), 2.34–2.79 (7H, m), 3.35–3.50 (1H, m), 3.64 and 3.68 (total 1H, s), 3.91–4.11 (2H, m), 4.37 (1H, br), 6.67–6.71 (1H, m), 7.01 (1H, s), 7.04–7.26 (2H, m), 7.32–7.37 (1H, m), 7.56–7.60 (1H, m), 8.14–8.20 (1H, m)

Mass (m/z): 597 (M$^+$+1)

(19) N-[(R)-1-{3-(1-tert-butoxycarbonyl-4-piperidyl)propionyl}-3-piperidylcarbonyl]-3(R)-(3-trifluoromethylphenethyl)-β-alanine methyl ester IR (Film): 2980, 2925, 2860, 1720, 1645 cm$^{-1}$
NMR (CDCl$_3$, δ): 1.00–1.21 (2H, m), 1.45 (9H, s), 1.45–1.72 (9H, m), 1.84–2.20 (3H, m), 2.34–2.77 (9H, m), 3.39–3.50 (1H, m), 3.63–3.69 (4H, m), 3.80–3.81 (1H, m), 4.02–4.17 (2H, m), 4.25–4.39 (1H, m), 6.45–6.53 (1/3H, m)), 6.89–6.93 (2/3H, m), 7.35–7.43 (4H, m)
Mass (m/z): 626 (M$^+$+1)

(20) N-[(R)-1-{3-(1-tert-butoxycarbonyl-4-piperidyl)propionyl}-3-piperidylcarbonyl]-3 (R)-(2-methoxyphenethyl)-β-alanine methyl ester
IR (Film): 2990, 2930, 2860, 1725, 1660, 1620 cm$^{-1}$
NMR (CDCl$_3$, δ): 1.00–1.21 (2H, m), 1.45 (9H, s), 1.53–2.15 (11H, m), 2.21–2.38 (3H, m), 2.48–2.66 (6H, m), 3.15–3.60 (2H, m), 3.65 (3H, s), 3.81 (3H, s), 3.86–4.50 (4H, m), 6.23–6.35 (1H, m), 6.64 (1H, d, J=8.6 Hz), 6.81–6.91 (2H, m), 7.09–7.19 (2H, m)
Mass (m/z): 588 (M$^+$+1)

(21) N-[(R)-1-{3-(1-tert-butoxycarbonyl-4-piperidyl)propionyl}-3-piperidylcarbonyl]-3(R)-(3,4-methylenedioxyphenethyl)-β-alanine methyl ester
IR (Film): 2980, 2925, 2860, 1725, 1630 cm$^{-1}$
NMR (CDCl$_3$, δ): 1.00–1.21 (2H, m), 1.45 (9H, s), 1.56 (2H, d, J=7.4 Hz), 1.45–2.11 (8H, m), 2.34–2.73 (10H, m), 3.16–3.60 (3H, m), 3.66 (3H, s), 3.91 (1H, dd, J=13.7 and 3.5 Hz), 4.02–4.15 (2H, m), 4.20–4.34 (1H, m), 5.91 (2H, s), 6.59–6.74 (3H, m), 6.79 (1H, d, J=8.7 Hz)
Mass (m/z): 602 (M$^+$+1)

(22) N-[(R)-1-{3-(1-tert-butoxycarbonyl-4-piperidyl)propionyl}-3-piperidylcarbonyl]-3(S)-vinyl-β-alanine ethyl ester
IR (Film): 3300, 1720, 1680, 1630, 1530 cm$^{-1}$
NMR (CDCl$_3$, δ): 1.03–1.21 (2H, m), 1.26 (3H, t, J=7.2 Hz), 1.45 (9H, s), 1.52–2.05 (10H, m), 2.33–2.41 (3H, m), 2.55–2.73 (4H, m), 3.27–3.54 (2H, m), 4.07–4.18 (5H, m), 4.62–4.90 (1H, m), 5.12–5.24 (2H, m), 5.76–5–92 (1H, m), 6.64–6.68, 6.88–6.92 (total 1H, m)
Mass (m/z): 494 (M$^+$+1)

(23) N-[(R)-1-{3-(1-tert-butoxycarbonyl-4-piperidyl)propionyl}-3-piperidylcarbonyl]-3(S)-ethynyl-β-alanine ethyl ester
IR (Film): 3250, 1730, 1670, 1630, 1610 cm$^{-1}$
NMR (CDCl$_3$, δ): 1.00–1.21 (2H, m), 1.28 (3H, t, J=7.2 Hz), 1.50 (9H, s), 1.52–2.03 (9H, m), 1.98 (1H, s), 2.28–2.40 (4H, m), 2.62–2.73 (4H, m), 3.21–3.62 (2H, m), 4.07–4.23 (5H, m), 5.08–5.12 (1H, m), 7.06 and 7.28 (total 1H, br)

(24) N-[(R)-1-{3-(1-tert-butoxycarbonyl-4-piperidyl)propionyl}-3-piperidylcarbonyl]-3(S)-propargylaminocarbonyl-β-alanine benzyl ester
IR (Film): 3020, 2910, 2840, 1720, 1640, 1620 cm$^{-1}$
NMR (CDCl$_3$, δ): 0.98–1.19 (2H, m), 1.45 (9H, s), 1.51–1.71 (7H, m), 1.84–2.04 (2H, m), 2.20–2.40 (4H, m), 2.60–3.10 (5H, m), 3.16–3.36 (2H, m), 3.54–3.91 (1H, m), 3.97–4.44 (5H, m), 4.79 (1H, q, J=6.4 Hz), 5.14 (2H, s), 6.81–6.89 (1H, m), 7.35 (5H, s)
Mass (m/z): 611 (M$^+$+1)

(25) N-[1-{3-(1-tert-butoxycarbonyl-4-piperidyl)propionyl}-3-pyrrolidinylcarbonyl]-3(S)-ethynyl-β-alanine ethyl ester
IR (Film): 3280, 1730, 1670, 1630, 1530 cm$^{-1}$
NMR (CDCl$_3$, δ): 1.8–1.18 (2H, m), 1.26–1.33 (3H, t, J=7.4 Hz), 1.45 (9H, s), 1.59–1.69 (2H, m), 1.64 (3H, s), 2.09–2.31 (5H, m), 2.61–2.96 (5H, m), 3.44–3.76 (4H, m), 4.15–4.19 (2H, m), 4.22 (2H, q, J=7.4 Hz), 5.05–5.12 (1H, m), 6.50–6.70 (1H, m)

(26) N-[(R)-1-{3-(1-tert-butoxycarbonyl-4-piperidyl)propionyl}-3-piperidylcarbonyl]-2-methyl-β-alanine methyl ester IR (Film): 3260, 1720 cm$^{-1}$
NMR (CDCl$_3$, δ): 1.08–1.45 (4H, m), 1.52 (9H, s), 1.60–1.63 (7H, m), 1.92–1.97 (2H, m), 2.25–2.39 (3H, m), 2.62–2.73 (3H, m), 3.24–3.56 (5H, m), 3.71 (3H, s), 3.56–3.70 (1H, m), 4.05–4.11 (3H, m), 6.42–6.58 (1H, m)
Mass (m/z): 468 (M$^+$+1)

(27) N-[(S)-1-{3-(1-tert-butoxycarbonyl-4-piperidyl)propionyl}-3-piperidylcarbonyl]-3-ethynyl-β-alanine ethyl ester
IR (Film): 2980, 2930, 2860, 1730, 1640 cm$^{-1}$
NMR (CDCl$_3$, δ): 1.01–1.21 (2H, m), 1.28 (3H, t, J=7.1 Hz), 1.45 (9H, s), 1.40–1.80 (7H, m), 1.88–2.00 (2H, m), 2.28 (1H, d, J=2.4 Hz), 2.32–2.46 (3H, m), 2.61–2.74 (6H, m), 3.33 (1H, dd, J=13.6 and 9.2 Hz), 4.02–4.14 (3H, m), 4.19 (2H, q, J=7.1 Hz), 5.03–5.14 (1H, m), 6.68–7.02 (1H, m)
Mass (m/z): 492 (M$^+$+1)

(28) 4-[3-{3-(1-tert-butoxycarbonyl-4-piperidyl)propionyl-amino}-1-piperidyl]-4-oxo-butyric acid methyl ester
IR (Film): 2970, 2920, 2850, 1725, 1650, 1630 cm$^{-1}$
NMR (CDCl$_3$, δ): 0.98–1.21 (2H, m), 1.45 (9H, s), 1.53–1.92 (9H, m), 2.23 (2H, q, J=7.1 Hz), 2.36–2.99 (6H, m), 3.15–3.59 (3H, m), 3.69 (3H, s), 3.74–3.92 (1H, m), 4.00–4–13 (3H, m), 6.09 and 6.24 (total 1H, d, J=6.5 and 7.6 Hz)
Mass (m/z): 354 (M$^+$+1-Boc)

(29) 4-[3-{3-(1-tert-butoxycarbonyl-4-piperidyl)propionylamino}piperidyl]-4-oxo-2(S)-benzyloxycarbonylaminobutyric acid tert-butyl ester
IR (Film): 2950, 2900, 2850, 1700, 1640 cm$^{-1}$
NMR (CDCl$_3$, δ): 0.97–1.19 (2H, m), 1.43 (9H, s), 1.44 (9H, s), 1.52–2.05 (9H, m), 2.14–2.33 (2H, m), 2.45–2.74 (4H, m), 2.88–3.58 (3H, m), 3.73–4.48 (5H, m), 4.81–5.19 (3H, m), 6.75–6.79 and 6.76–6.82 (total 1H, m), 7.34 (5H, s)
Mass (m/z): 645 (M$^+$+1)

(30) N-[(R)-1-{3-(1-tert-butoxycarbonyl-4-piperidyl)propionyl}-3-piperidylcarbonyl]-2(S)-acetylamino-β-alanine ethyl ester
IR (Film): 3300, 1730, 1660 cm$^{-1}$
NMR (CDCl$_3$, δ): 1.08–1.13 (2H, m), 1.28 (3H, t, J=7.1 Hz), 1.45 (9H, s), 1.54–1.74 (10H, m), 2.06 (3H, s), 2.25–2.47 (4H, m), 2.62–2.74 (2H, m), 3.25–3.38 (2H, m), 3.82–3.90 (1H, m), 4.03–4.26 (6H, m), 4.72–4.76 (1H, m), 7.19–7.26 (1H, m)
Mass (m/z): 525 (M$^+$+1)

(31) Ethyl N-[(R)-1-{3-(1-tert-butoxycarbonyl-4-piperidyl)propionyl}-3-piperidylcarbonyl]-2-piperidyl carboxylate
NMR (DMSO-d$_6$, δ): 0.82–1.09 (2H, m), 1.17 (3H, t, J=7.1 Hz), 1.38 (9H, s), 1.31–1.99 (11H, m), 2.25–2.39 (2H, m), 2.53–3.14 (8H, m), 3.32–4.08 (6H, m), 4.03 (2H, q, J=7.1 Hz), 4.16–4.37 (2H, m)
Mass (m/z): 508 (M$^+$+1)

(32) N-[(R)-1-{3-(1-tert-butoxycarbonyl-4-piperidyl)propionyl}-3-piperidylcarbonyl]-2-benzyl-β-alanine ethyl ester
NMR (DMSO-d$_6$, δ): 0.84–1.21 (5H, m), 1.38 (9H, s), 1.38–1.89 (11H, m), 2.26–2.37 (2H, m), 2.52–3.29 (9H, m), 3.68–4.08 (4H, m), 4.13–4.41 (1H, m), 7.14–7.31 (5H, m), 7.95–8.12 (1H, m)
Mass (m/z): 558 (M$^+$+1)

(33) N-[(R)-1-{3-(1-tert-butoxycarbonyl-4-piperidyl)propionyl}-3-piperidylcarbonyl]-2-phenyl-β-alanine ethyl ester
NMR (DMSO-d$_6$, δ): 0.85–1.07 (2H, m), 1.14 (3H, t, J=7.1 Hz), 1.38 (9H, s), 1.38–1.86 (9H, m), 1.99–2.43 (3H, m), 2.51–3.08 (4H, m), 3.33–4.34 (9H, m), 7.28–7.38 (5H, m), 7.96–8.12 (1H, m)

Mass (m/z): 544 (M⁺+1)

EXAMPLE 2

(1) To a mixture of 2(S)-(tert-butoxycarbonyl)amino-)3-alanine ethyl ester (2.89 g), (R)-1-[3-(1-benzyloxycarbonyl-4-piperidyl)propionyl]-3-piperidinecarboxylic acid (5.02 g) and 1-hydroxybenztriazole (1.69 g) in N,N-dimethylformamide (2.27 ml) under stirring at 0° C. After stirring at ambient temperature for overnight, the mixture was poured into water and extracted with ethyl acetate. The extract was washed with water, brine and dried over MgSO₄, and evaporated in vacuo. The residue was purified by chromatography on silica gel eluting with (CHCl₃:MeOH=100:1) to give N-[(R)-1-{3-(1-benzyloxycarbonyl-4-piperidyl)propionyl}-3-piperidylcarbonyl]-2(S)-(tert-butoxycarbonyl)amino-β-alanine ethyl ester (6.0 g).

IR (Film): 2970, 2930, 2850, 1720, 1680 cm⁻¹

NMR (CDCl₃, δ): 1.04–1.34 (6H, m), 1.47 (9H, s), 1.47–1.81 (9H, m), 2.18–2.49 (3H, m), 2.70–2.82 (2H, m), 3.18–3.40 (2H, m), 3.46–3.60 (2H, m), 3.91–4.25 (6H, m), 4.33–4.45 (1H, m), 5.12 (2H, s), 5.86–5.96 and 7.09–7.17 (total 1H, m), 7.32–7.36 (5H, m)

Mass (m/z): 617 (M⁺+1)

The following compounds were obtained according to a similar manner to that of Example 2 (1).

(2) N-[1-{3-(1-benzyloxycarbonyl-4-piperidyl)propionyl}-3-piperidylcarbonyl]-3-methyl-β-alanine methyl ester IR (Film): 3050, 2930, 2850, 1730, 1680, 1635 cm⁻¹

NMR (CDCl₃, δ): 1.02–1.30 (5H, m), 1.40–2.69 (14H, m), 2.76 (2H, t, J=12.9 Hz), 3.19–3.68 (5+1/2H, m), 3.83–4.01 (1/2H, m), 4.10–4.50 (4h, m), 5.12 (2h, s), 6.30–6.39 (1/3H, m), 6.50–6.54 (1/3H, m), 6.68–6.72 (1/3H, m), 7.30–7.37 (5H, m)

Mass (m/z): 502 (M⁺+1)

(3) N-[(R)-1-{2-(1-benzyloxycarbonyl-4-piperidyloxy)-acetyly-3-piperidylcarbonyl]-β-alanine ethyl ester IR (Film): 3300, 2940, 2870, 1720, 1680, 1640 cm⁻¹

NMR (CDCl₃, δ): 1.27 (3H, t, J=7.1 Hz), 1.43–1.96 (8H, m), 2.19–2.34 (1H, m), 2.51 (2H, t, J=6.1 Hz), 3.05–3.31 (4H, m), 3.47–3.63 (3H, m), 3.69–3.96 (3H, m), 4.15 (2H, q, J=7.1 Hz), 4.17–4.37 (3H, m), 5.12 (2H, s), 6.30–6.38 (1/3H, m), 6.51–6.59 (2/3H, m), 7.30–7.37 (5H, m)

Mass (m/z): 504 (M⁺+1)

(4) N-[(R)-1-{2-(1-benzyloxycarbonyl-4-piperidyloxy)-acetyl}-3-piperidylcarbonyl]-3-ethynyl-β-alanine ethyl ester IR (Film): 2930, 2860, 1720, 1640 cm⁻¹

NMR (CDCl₃, δ): 1.28 (3H, t, J=7.1 Hz), 1.45–1.97 (8H, m), 2.23–2.38 (1H, m), 2.27 (1H, d, J=1.5 Hz), 2.70 (2H, t, J=5.7 Hz), 3.13–3.29 (4H, m), 3.54–3.64 (1H, m), 3.75–4.04 (3H, m), 4.07–4.37 (5H, m), 5.03–5.12 (1H, m), 5.12 (2H, s), 6.66–6.97 (1H, m), 7.30–7.36 (5H, m)

Mass (m/z): 528 (M⁺+1)

(5) N-[(S)-1-{2-(1-benzyloxycarbonyl-4-piperidyloxy)-acetyl}-3-piperidylcarbonyl]-β-alanine ethyl ester IR (Film): 3305, 2940, 2860, 1720, 1680, 1640 cm⁻¹

NMR (CDCl₃, δ): 1.27 (3H, t, J=7.1 Hz), 1.41–1.68 (4H, m), 1.76–1.97 (4H, m), 2.19–2.34 (1H, m), 2.51 (2H, t, J=5.9 Hz), 3.06–3.31 (4H, m), 3.47–3.61 (3H, m), 3.70–4.00 (3H, m), 4.15 (2H, q, J=7.1 Hz), 4.14–4.37 (3H, m), 5.12 (2H, s), 6.23–6.34 (1/3H, m), 6.44–6.53 (2/3H, m), 7.32–7.37 (5H, m)

Mass (m/z): 504 (M⁺+1)

(6) N-[(R)-1-{3-(1-benzyloxycarbonyl-4-piperidyl)propionyl}-3-piperidylcarbonyl]-2(R)-tert-butoxycarbonylamino-β-alanine methyl ester IR (Film): 3000, 2970, 2930, 2850, 1740, 1680, 1650, 1630 cm⁻¹

NMR (CDCl₃, δ): 1.03–1.24 (2H, m), 1.44 (9H, s), 1.53–2.05 (9H, m), 2.20–2.44 (3H, m), 2.60–2.84 (2H, m), 3.19–3.61 (4H, m), 3.75 (3H, s), 3.85–4.47 (5H, m), 5.12 (2H, s), 5.51–5.67 (1H, m), 6.44–6.51 and 6.74–6.81 (total 1H, m), 7.30–7.37 (5H, m)

Mass (m/z): 603 (M⁺+1)

EXAMPLE 3

(1) To a mixture of N-[(3-piperidyl)carbonyl]-β-alanine methyl ester hydrochloride (1.57 g),3-(1 -tert-butoxycarbonyl-4-piperidyl)propionic acid (1.61 g) and 1-hydroxybenztriazole (0.96 g) in N,N-dimethylformamide (16 ml) was added 1-ethyl-3-(3-dimethylaminopropyl)carbodiimide (1.14 ml) under stirring at 0° C. After stirring at ambient temperature for 1 hour, the mixture was poured into water and extracted with ethyl acetate. The extract was washed with water, brine and dried over MgSO₄, and evaporated in vacuo. The residue was purified by chromatography on silica gel eluting with (CHCl₃:MeOH 100:1) to give N-[1-{3-(1-tert-butoxycarbonyl-4-piperidyl)propionyl}-3-piperidylcarbonyl]-β-alanine methyl ester as an oil (2.19 g).

IR (Film): 3410, 3280, 3070, 2910, 2850, 1725, 1680, 1630 cm⁻¹

NMR (CDCl₃, δ): 1.03–1.21 (2H, m.), 1.45 (9H, s), 1.45–2.05 (10H, m), 2.23–2.39 (3H, m), 2.49–2.73 (4H, m), 3.18–3.64 (4H, m), 3.32 (3H, s), 3.81–4.23 and 4.36–4.49 (total 3H, m), 6.23–6.35 and 6.52–6.62 (total 1H, m)

Mass (m/z): 454 (M⁺+1)

The following compounds were obtained according to a similar manner to that of Example 3 (1).

(2) N-[1-{3-(1-tert-butoxycarbonyl-4-piperidyl)-propionyl}-4-piperidylcarbonyl]-β-alanine methyl ester mp: 79° C.

IR (Nujol): 3290, 3100, 1740, 1690, 1640, 1615 cm⁻¹

NMR (CDCl₃, δ): 1.00–1.20 (2H, m), 1.45 (9H, s), 1.52–1.77 (7H, m), 1.77–1.92 (2H, m), 2.23–2.38 (3H, m), 2.54 (2H, t, J=5.8 Hz), 2.62–2.73 (3H, m), 2.99–3.10 (1H, m), 3.52 (2H, q, J=5.8 Hz), 3.71 (3H, s), 3.82–3.95 (1H, m), 4.02–4.15 (2H, m), 4.53–4.67 (1H, m), 6.20–6.29 (1H, m)

Mass (m/z): 454 (M⁺+1)

(3) N-[2-[1-{3-(1-tert-butoxycarbonyl-4-piperidyl)-propionyl}-4-piperidyl]acetyl]-β-alanine methyl ester IR (Film): 3300, 1730, 1660 cm⁻¹

NMR (CDCl₃, δ): 1.08–1.14 (4H, m), 1.45 (9H, s), 1.52–1.76 (9H, m), 2.05–2.07 (2H, m), 2.29–2.37 (2H, m), 2.52–2.73 (4H, m}, 2.96–3.01 (1H, m), 3.48–3.57 (2H, m), 3.71 (3H, s), 3.78–3.82 (1H, m), 4.04–4.08 (2H, m), 4.58–4.64 (1H, m), 6.04–6.08 (1H, m)

Mass (m/z): 468 (M⁺+1)

(4) N-[1-{3-(1-tert-butoxycarbonyl-4-piperidyl)-propionyl}-3-piperidylcarbonyl]-N-methyl-β-alanine methyl ester IR (Film): 3450, 2900, 1720, 1670, 1650, 1620 cm⁻¹

NMR (CDCl₃, δ): 1.08–1.36 (2H, m), 1.45 (9H, s), 1.50–1.87 (10H, m), 2.36–2.45 (2H, m), 2.53–2.72 (6H, m), 2.91, 3.11 (total 3H, s), 3.60–3.70 (3H, m), 3.80–3.88 (1H, m), 4.05–4.60 (2H, m), 4.60–4.66 (1H, m)

Mass (m/z): 468 (M⁺)

(5) N[2-[1-{2-(1-tert-butoxycarbonyl-4-piperidyl)-acetyl}-3-piperidyl]acetyl]-β-alanine methyl ester IR (Film): 3300, 2920, 2850, 1730, 1630 cm⁻¹

NMR (CDCl₃, δ): 1.03–1.30 (3H, m), 1.30–2.11 (12H, m), 1.45 (9H, s), 2.13–2.19 (1/2H, m), 2.25 (2H, d, J=6.5

Hz), 2.52–2.60 (2H, m), 2.64–2.81 (2+1/2H, m), 3.05–3.15 (1/2H, m), 3.23–3.36 (1/2H, m), 3.48–3.57 (2+1/2H, m), 3.70 (3H, d, J=1.5 Hz), 4.31–4.44 (1/2H, m), 6.07–6.17 (1/2H, m), 6.59–6.69 (1/2H, m)

Mass (m/z): 454 ($M^+$+1)

(6) N-[1-{4-(1-tert-butoxycarbonyl-4-piperidyl)butyryl}-3-piperidylcarbonyl]glycine methyl ester IR (Film): 3280, 2910, 2650, 1740 $cm^{-1}$ NMR ($CDCl_3$, δ): 0.99–1.36 (4H, m), 1.45 (9H, s), 1.53–2.30 (9H, m), 2.31–2.54 (3H, m), 2.61–2.75 (2H, m), 3.44–3.55 (1H, m), 3.73 (3H, s), 3.78–4.20 and 4.37–4.52 (total 7H, m), 6.25–6.35 and 6.96–7.04 (total 1H, m)

Mass (m/z) 454 ($M^+$+1)

(7) N-[2-[1-{2-(1-tert-butoxycarbonyl-4-piperidylidene)acetyl}-3-piperidyl]acetyl]-β-alanine methyl ester mp 121° C.

IR (Nujol): 3320, 1735, 1680, 1630 $cm^{-1}$

NMR ($CDCl_3$, δ): 1.15–1.80 (3H, m), 1.47 (9H, s), 1.80–2.11 (4H, m), 2.25 (1H, t, J=5.0 Hz), 2.46 (2H, t, J=5.7 Hz), 2.56 (2H, q, J=6.3 Hz), 2.74–2.87 (1H, m), 3.10–3.40 (1H, m), 3.43–3.55 (6+1/2H, m), 3.70 (3H, s), 3.82–3.96 (1H, m), 4.29–4.42 (1/2H, m), 5.86 (1H, s), 6.10–6.23 and 6.65–6.80 (total 1H, m)

Mass (m/z): 452 ($M^+$+1)

(8) N-[1-{3-(1-tert-butoxycarbonyl-4-piperidyl)propionyl}-3-piperidyl]succinamic acid methyl ester IR (Film): 2960, 2920, 2850, 1725, 1650, 1620 $cm^{-1}$ NMR ($CDCl_3$, δ): 1.00–1.21 (2H, m), 1.45 (9H, s), 1.53–1.99 (9H, m), 2.31–2.48 (4H, m), 2.60–2.76 (4H, m), 3.04–3.44 (2H, m), 3.60–3.95 (3H, m), 3.69 (3H, s), 4.03–4.11 (2H, m), 5.70–5.93 (1H, m)

Mass (m/z): 454 ($M^+$+1)

(9) N-[2-[1-{3-(1-benzyloxycarbonyl-4-piperidyl)propionyl}-3-piperidyl]acetyl]glycine methyl ester IR (Film): 2920, 2850, 1740, 1675, 1615 $cm^{-1}$ NMR ($CDCl_3$, δ): 1.01–1.80 (10H, m), 1.80–2.43 (6H, m), 2.63–2.88 (3H, m), 3.37–3.69 (2H, m), 3.75 (3H, s), 3.82–3.95 (1/2H, m), 4.01–4.29 (4H, m), 4.29–4.42 (1/2H, m), 5.12 (2H, s), 6.01–6.10 (1/2H, m), 6.99–7.08 (1/2H, m), 7.30–7.37 (5H, m)

Mass (m/z): 488 ($M^+$+1)

(10) N-[1-{3-(1-benzyloxycarbonyl-4-piperidyl)propionyl}-3-piperidyl]-2(S)-(tert-butoxycarbonylamino)succinamic acid ethyl ester IR (Film): 3300, 2930, 2860, 1735, 1680, 1635 $cm^{-1}$ NMR ($CDCl_3$, δ): 1.01–1.27 (2H, m), 1.27 (3H, t, J=7.1 Hz), 1.45 (9H, s), 1.49–1.98 (9H, m), 2.30–2.40 (2H, m), 2.68–2.84 (4H, m), 2.96–3.17 (1H, m), 3.35–3.53 (1H, m), 362–4.23 (5H, m), 4.21 (2H, q, J=7.1 Hz), 4.43–4.54 (1H, m), 5.12 (2H, s), 5.58–5.74 (1H, m), 5.83–5.96 (1H, m), 7.35–7.37 (5H, m)

Mass (m/z): 617 ($M^+$+1)

(11) N-[1-{3-(1-benzyloxycarbonyl-4-piperidyl)propionyl}-3-piperidyl]-3(S)-(tert-butoxycarbonylamino)succinamic acid methyl ester IR (Film): 3000, 2940, 2860, 1720, 1680, 1640 $cm^{-1}$ NMR ($CDCl_3$, δ): 1.03–1.24 (2H, m), 1.46 (9H, s), 1.52–1.78 (11H, m), 2.30–2.40 (2H, m), 2.60–3.39 (6H, m), 3.70 (3H, d, J=2.6 Hz), 3.64–3.95 (2H, m), 4.11–4.23 (2H, m), 4.38–4.49 (1H, m), 5.12 (2H, s), 5.62–5.75 and 6.55–6.69 (total 1H, m), 7.35–7.37 (5H, m)

Mass (m/z): 603 ($M^+$+1)

(12) N-[1-{3-(1-benzyloxycarbonyl-4-piperidyl)propionyl-3-piperidyl]-3(R)-(tert-butoxycarbonylamino)succinamic acid ethyl ester IR (Film): 2960, 2910, 2840, 1710, 1680, 1660, 1640 $cm^{-1}$ NMR ($CDCl_3$, δ): 1.03–1.26 (3H, t, J=7.1 Hz), 1.46 (9H, s), 1.46–1.98 (9H, m), 2.35 (2H, t, J=7.9 Hz), 2.59–3.52 (6H, m), 3.65–3.98 (3H, m), 4.14 (2H, q, J=7.1 Hz), 4.09–4.20 (2H, m), 4.39–4.49 (1H, m), 5.12 (2H, s), 5.62–5.76 (1H, m), 6.59–6.61 (1H, m), 7.29–7.37 (5H, m)

Mass (m/z) 617 ($M^+$+1)

EXAMPLE 4

(1) A mixture of N-[(R)-3-(1-benzyloxycarbonyl)-piperidylcarbonyl]-2(S)-benzoylamino-β-alanine ethyl ester (230 mg) and 10% Pd—C (50 mg, 50% wet) in ethanol (5 ml) and tetrahydrofuran (3 ml) was hydrogenated at atmospheric pressure for 1 hour. After the catalyst was removed by filtration, the filtrate was concentrated in vacuo. The residue, 3-(1-tert-butoxycarbonyl-4-piperidyl)propionic acid (123 mg) and l-hydroxybenztriazole (65 mg) was dissolved in N,N-dimethylformamide (5 ml), and 1-ethyl-3-(3-dimethylaminopropyl)carbodiimide (87 μl) was added under stirring at 0° C. After stirring at ambient temperature for overnight, the mixture was poured. into water and extracted with ethyl acetate. The extract was washed with water, brine and dried over $MgSO_4$, and evaporated in vacuo. The residue was purified by chromatography on silica gel eluting with ($CHCl_3$:MeOH= 100:1) to give N-[(R)-1-{3-(1-tert-butoxycarbonyl-4-piperidyl)propionyl}-3-piperidylcarbonyl]-2(S)-benzoylamino-β-alanine ethyl ester as an oil (213 mg).

IR (Film): 2960, 2920, 2850, 1730, 1650 $cm^{-1}$

NMR ($CDCl_3$, δ): 0.85–1.33 (2H, m), 1.29 (3H, t, J=7.1 Hz), 1.45 (9H, s), 1.45–2.12 (9H, m), 2.20– 2.70 (7H, m), 3.14–3.79 (4H, m), 3.97–4.30 (5H, m), 4.80–4.96 (1H, m), 7.39–7.48 (3H, m), 7.51–7.60 (2/3H, m), 7.8–7.84 (1/3H, m), 7.96–8.04 (2H, m)

Mass (m/z): 587 ($M^+$+1)

The following compounds were obtained according to a similar manner to that of Example 4 (1).

(2) N-[(R)-1-{3-(1-tert-butoxycarbonyl-4-piperidyl)propionyl}-3-piperidylcarbonyl]-2(S)-(n-butanesulfonylamino)-β-alanine ethyl ester IR (Film): 2910, 2850, 1720, 1630 $cm^{-1}$ NMR ($CDCl_3$, δ): 0.94 (3H, t, J=7.3 Hz), 1.02–1.38 (2H, m), 1.30 (3H, t, J=7.1 Hz), 1.45 (9H, s), 1.45–1.89 (13H, m), 1.27–2.51 (4H, m), 2.61–2.73 (2H, m), 2.97–3.05 (2H, m), 3.25–3.40 (2H, m), 3.60–3.75 (1H, m), 4.01–4.30 (7H, m), 6.18 (1H, d, J=8.9 Hz), 7.35–7.42 (1H, m)

Mass (m/z): 603 ($M^+$+1)

(3) N-[(R)-1-{3-(1-tert-butoxycarbonyl-4-piperidyl)propionyl}-3-piperidylcarbonyl]-2(S)-phenylsulfonylamino-β-alanine ethyl ester IR (Film): 3400, 1720, 1645, 1620 $cm^{-1}$ NMR ($CDCl_3$, δ) 1.14 (2H, t, J=7.1 Hz), 1.08–1.17 (3H, m), 1.46 (9H, s), 1.46–1.77 (9H, m), 2.24–2.50 (4H, m), 2.56–2.78 (2H, m), 3.17–3.34 (2H, m), 3.58–3.73 (1H, m), 3.87–4.23 (7H, m), 6.48 (1H, d, J=9.3 Hz), 7.19–7.27 (1H, m), 7.45–7.56 (3H, m), 7.81–7.88 (2H, m)

Mass (m/z) 623 ($M^+$+1)

EXAMPLE 5

To a solution of 3-(1-benzyloxycarbonyl-4-piperidyl)propionic acid (0.18 g) in N,N-dimethylformamide (3 ml) was added N-methylmorpholine (0.09 ml) and isobutylchloroformate (0.1 ml) under stirring at −15° C. After stirring at −15° C. for 2 hours, N-[(1,2,3,4-tetrahydro-3-quinolyl)carbonyl]-β-alanine ethyl ester (0.22 g) and N-methylmorpholine (0.12 ml) in tetrahydrofuran (2 ml) was added. After stirring at 0° C. for 2 hours and ambient temperature for overnight, the mixture was poured into water, and extracted with ethyl acetate. The extract was washed with 5% KHSO$_4$ aqueous solution saturated NaHCO$_3$ aqueous solution and brine, and dried over MgSO$_4$, and evaporated in vacuo. The residue was purified by chromatography on silica gel eluting with (CHCl$_3$:MeOH=100:1) to give N-[1-{3-(1-benzyloxycarbonyl-4-piperidyl)propionyl}-1,2,3,4-tetrahydro-3-quinolylcarbonyl]-β-alanine ethyl ester as an oil (0.18 g).

NMR (CDCl$_3$, δ): 1.01–1.14 (2H, m), 1.27 (3H, t, J=7.1 Hz), 1.54–1.65 (4H, m), 2.48–2.56 (4H, m), 2.65–2.83 (3H, m), 2.95–3.07 (2H, m), 3.53 (2H, q, J=6.0 Hz), 3.72–3.87 (1H, m), 4.05–4.21 (4H, m), 4.16 (2H, q, J=7.2 Hz), 5.10 (2H, s), 6.60–6.67 (1H, m), 7.00–7.36 (9H, m)

Mass (m/z): 550 (M$^+$+1)

EXAMPLE 6

A solution of N-fluorenylmethoxycarbonyl-3-amino-3 (S)-cyanopropionic acid tert-butyl ester (0.3 g) in diethylamine (6 ml) was stirred for 1 hour, and concentrated in vacuo. The residue was purified by column chromatography on silica gel eluting with (CHCl$_3$:MeOH=100:3) to give an oil. To a mixture of 212 mg of this oil, (R)-1-[3-(tert-butoxycarbonyl)-4-piperidyl)propionyl]-3-piperidine] carboxylic acid (571 mg) 1-hydroxybenztriazole (209 mg) in N,N-dimethylformamide (4 ml) and 1-ethyl-3-(3-dimethylaminopropyl)carbodiimide (283 μl) were added under stirring at 0° C. After stirring at ambient temperature for overnight, the mixture was poured into water and extracted with ethyl acetate. The extract was washed with water, brine and dried over MgSO$_4$, and evaporated in vacuo. The residue was purified by chromatography on silica gel eluting with (CHCl$_3$:MeOH=100:1) to give N-[(R)-1-{3-(1-tert-butoxycarbonyl-4-piperidyl)propionyl}-3-piperidylcarbonyl]-3(S)-cyano-β-alanine tert-butyl ester (0.4 g).

IR (Film): 2980, 2930, 2860, 2250, 1720, 1640 cm$^{-1}$

NMR (CDCl$_3$, δ): 1.05–1.25 (2H, m), 1.45 (9H, s), 1.49 (9H, s), 1.54–2.09 (10H, m), 2.32–2.39 (3H, m), 2.61–2.79 (2H, m), 2.74 (2H, d, J=5.6 Hz), 3.23–3.62 (3H, m), 4.00–4.14 (2H, m), 5.12–5.22 (1H, m), 7.51 (1 h, d, J=8.4 Hz)

Mass (m/z): 521 (M$^+$+1)

EXAMPLE 7

(1) To a solution of N-[(R)-1-{3-(1-benzyloxycarbonyl-4-piperidyl)propionyl}-3-piperidylcarbonyl]-2(S)-(tert-butoxycarbonyl)amino-β-alanine ethyl ester (5.98 g) in ethyl acetate (60 ml) was added a solution of 4N HCl in ethyl acetate (24.2 ml) under stirring at 0° C. After stirring at ambient temperature for 2 hours, the resulting precipitates were collected by filtration to give N-[(R)-1-{3-(1-benzyloxycarbonyl-4-piperidyl)propionyl}-3-piperidylcarbonyl]-2(S)-amino-β-alanine ethyl ester hydrochloride (3.41 g).

IR (Nujol): 1745, 1695, 1650 cm$^{-1}$

NMR (DMSO-d$_6$, δ): 0.89–1.10 (2H, m), 1.19–1.91 (13H, m), 2.11–2.43 (3H, m), 2.57–3.17 (4H, m), 3.46–4.38 (4H, m), 5.06 (2H, s), 7.28–7.42 (5H, m)

Mass (m/z): 517 (M$^+$+1) free of compound

The following compounds were obtained according to a similar manner to that of Example 7 (1).

(2) N-[1-{3-(1-benzyloxycarbonyl-4-piperidyl)propionyl-3-piperidyl]-2(S)-aminosuccinamic acid ethyl ester hydrochloride IR (Nujol): 1730, 1640 cm$^{-1}$ NMR (DMSO-d$_6$, δ): 1.17 (3H, t, J=7.1 Hz), 1.33–1.51 (6H, m), 1.60–1.84 (5H, m), 2.22–2.37 (2H, m), 2.69–3.06 (7H, m), 3.51–3.87 (2H, m), 3.94–4.05 (1H, m), 4.12–4.29 (4H, m), 5.06 (2H, s), 7.30–7.42 (5H, m), 8.27–8.43 (1H, m)

Mass (m/z): 517 (M$^+$+1) free of compound (3) N-[(R)-1-{3-(1-benzyloxycarbonyl-4-piperidyl) propionyl}-3-piperidylcarbonyl]-2(R)-amino-β-alanine methyl ester hydrochloride IR (Nujol): 1740, 1640 cm$^{-1}$ NMR (DMSO-d$_6$, δ): 0.90–1.09 (2H, m), 1.21–1.91 (13H, m), 2.11–2.43 (4H, m), 2.61–3.17 (6H, m), 3.45–4.46 (5H, m), 5.06 (2H, s), 7.30–7.42 (5H, m), 8.38–8.59 (1H, m)

Mass (m/z): 503 (M$^+$+1) free of compound (4) N-[1-{3-(1-benzyloxycarbonyl-4-piperidyl)propionyl}-3-piperidyl]-3(S)-aminosuccinamic acid methyl ester hydrochloride mp: 75° C.

IR (Nujol): 1725, 1670, 1640, 1600 cm$^{-1}$

NMR (DMSO-d$_6$, δ): 0.90–1.09 (2H, m), 1.31–1.88 (11H, m), 2.20–2.38 (2H, m), 2.60–3.25 (7H, m), 3.49–3.74 (2H, m), 3.91–4.09 (4H, m), 5.06 (2H, S), 7.35 (5H, s), 8.66–8.84 (1H, m)

Mass (m/z): 503 (M$^+$+1) free of compound (5) N-[1-{3-(1-benzyloxycarbonyl-4-piperidyl)propionyl}-3-piperidyl]-3(R)-aminosuccinamic acid ethyl ester hydrochloride IR (KBr, pellet): 2939, 2864, 1732, 1684, 1616 cm$^{-1}$ NMR (DMSO-d$_6$, δ): 0.90–1.09 (2H, m), 1.20 (3H, t, J=7.0 Hz), 1.37–1.53 (6H, m), 1.60–1.86 (4H, m), 2.20–2.39 (2H, m), 2.60–3.26 (6H, m), 3.51–3.73 (2H, m), 3.88–4.28 (3H, m), 4.09 (2H, q, J=7.0 Hz), 5.06 (2H, s), 7.30–7.42 (5H, m), 8.64–8.75 (1H, m)

Mass (m/z): 517 (M$^+$+1) free of compound

EXAMPLE 8

(1) To a solution of N-[(R)-1-{3-(1-benzyloxycarbonyl-4-piperidyl)propionyl}-3-piperidylcarbonyl]-2(S)-amino-β-alanine ethyl ester hydrochloride (270 mg) in dichloromethane (4 ml) was added triethylamine (150 μl) and acetyl chloride (38 μl) under stirring at 0° C. After stirring at ambient temperature for 2 hours, the mixture was poured into water and extracted with dichloromethane. The extract was washed with water, saturated NaHCO$_3$ aqueous solution, water and brine, and dried over MgSO$_4$, and evaporated in vacuo. The residue was purified by column chromatography on silica gel eluting with (CHCl$_3$:MeOH=100:1) to give N-[(R)-1-{3-(1-benzyloxy-carbonyl-4-piperidyl)propionyl}-3-piperidylcarbonyl]-2 (S)-acetylamino-β-alanine ethyl ester as an oil (130 mg).

IR (Film): 3290, 3060, 3000, 2930, 2850, 1725, 1675, 1640 cm$^{-1}$

NMR (CDCl$_3$, δ): 1.06–1.34 (2H, m), 1.27 (3H, t, J=7.1 Hz), 1.41–1.76 (10H, m), 2.09 (3H, s), 2.31–2.50 (3H, m), 2.70–2.83 (2H, m), 3.16–3.31 (3H, m), 3.64–3.74 (1H, m), 4.05–4.34 (6H, m), 4.70–4.80 (1H, m), 5.12 (2H, m), 7.05–7.22 (1H, m), 7.26–7.37 (5H, m)

Mass (m/z): 559 (M$^+$+1)

The following compounds were obtained according to a similar manner to that of Example 8 (1).

(2) N-[(R)-1-{3-(1-benzyloxycarbonyl-4-piperidylpropionyl}-3-piperidylcarbonyl]-2(S)-n-hexanoylamino-β-alanine ethyl ester IR (Film): 3000, 2940, 2870, 1735, 1655, 1640 cm$^{-1}$ NMR (CDCl$_3$, δ): 0.89 (3H, t, J=7.1 Hz), 1.12–1.38 (12H, m), 1.51–1.75 (7H, m), 2.24–2.51 (5H, m), 2.70–2.84 (2H, m), 3.25–3.70 (7H, m), 4.05–4.25 (5H, m), 4.69–4.80 (1H, m), 5.12 (2H, s), 7.03–7.15 (1H, m), 7.30–7.38 (5H, m)

Mass (m/z): 615 (M$^+$+1)

(3) N-[(R)-1-{3-(1-benzyloxycarbonyl-4-piperidyl) propionyl}-3-piperidylcarbonyl]-2(S)-(4-chlorobenzoylamino)-β-alanine ethyl ester IR (Film): 3000, 2930, 2860, 1740, 1680, 1650, 1600 cm$^{-1}$ NMR (CDCl$_3$, δ): 0.89–1.13 (2H, m), 1.29 (3H, t, J=7.1 Hz), 1.29–1.80 (11H, m), 2.20–2.55 (3H, m), 2.65–2.80 (2H, m), 3.12–3.28 (2H, m), 3.32–3.42 (1H, m), 3.61–3.79 (1H, m), 4.07–4.42 (5H, m), 4.90–4.98 (1H, m), 5.12 (2H, s), 7.35–7.43 (6H, m), 7.41 (2H, d, J=8.6 Hz), 8.00 (2H, d, J=8.6 Hz)

Mass (m/z): 655 (M$^+$+1)

(4) N-[(R)-1-{3-(1-benzyloxycarbonyl-4-piperidyl) propionyl}-3-piperidylcarbonyl]-2(S)-4-methoxybenzoylamino-β-alanine ethyl ester IR (Film): 2920, 1730, 1685, 1630, 1600 cm$^{-1}$ NMR (CDCl$_3$, δ): 0.84–1.80 (13H, m), 1.29 (3H, t, J=7.1 Hz), 2.26–2.56 (3H, m), 2.64–2.80 (2H, m), 3.15–3.86 (3H, m), 3.83 (3H, s), 4.05–4.38 and 5.87–5.97 (total 6H, m), 5.11 (2H, s), 5.92 (2H, d, J=8.8 Hz), 7.33–7.45 (6H, m), 7.75–7.81 (1H, m), 8.00 (2H, d, J=8.8 Hz)

Mass (m/z): 651 (M$^+$+1)

(5) N-[1-{3-(1-benzyloxycarbonyl-4-piperidyl)propionyl}-3-piperidyl]-2(S)-benzoylaminosuccinamic acid ethyl ester IR (Film): 2920, 1730, 1680, 1640 cm$^{-1}$ NMR (CDCl$_3$, δ): 1.03–1.33 (3H, m), 1.29 (3H, t, J=7.1 Hz), 1.38–1.97 (8H, m), 2.22–2.40 (2H, m), 2.64–3.13 (5H, m), 3.34–4.00 (4H, m), 4.08–4.28 (2H, m), 4.26 (2H, q, J=7.1 Hz), 4.91–5.01 (1H, m), 5.12 (2H, s), 5.86–6.00 (1H, m), 7.28–7.36 (5H, m), 7.41–7.56 (4H, m), 7.78–7.87 (2H, m)

Mass (m/z): 621 (M$^+$+1)

(6) N-[(R)-1-{3-(1-benzyloxycarbonyl-4-piperidyl) propionyl}-3-piperidylcarbonyl]-2(S)-cyclopropylcarbonylamino-β-alanine ethyl ester IR (Film): 3000, 2930, 2860, 1730, 1650 cm$^{-1}$ NMR (CDCl$_3$, δ): 0.73–1.37 (6H, m), 1.27 (3H, t, J=7.1 Hz), 1.40–1.80 (11H, m), 2.31–2.54 (3H, m), 2.68–2.88 (2H, m), 3.20–3.40 (2H, m), 3.62–3.75 (1H, m), 4.08–4.32 (6H, m), 4.72–4.81 (1H, m), 5.12 (2H, s), 6.70–6.80 and 7.08–7.15 (total 1H, m), 7.21–7.48 (6H, m)

Mass (m/z): 585 (M$^+$+1)

(7) N-[(R)-1-{3-(1-benzyloxycarbonyl-4-piperidyl) propionyl}-3-piperidylcarbonyl]-2(R)-benzoylamino-β-alanine methyl ester IR (Film): 3060, 3010, 2960, 2860, 1740, 1690, 1640, 1610 cm$^{-1}$ NMR (CDCl$_3$, δ): 0.99–1.21 (2H, m), 1.32–1.87 (8H, m), 2.03–2.48 (2H, m), 2.33 (2H, t, J=7.7 Hz), 2.62–2.83 (2H, m), 3.36–3.45 (2H, m), 3.62–3.80 and 4.33–4.44 (total 4H, m), 3.77 (3H, s), 4.10.–4.22 (2H, m), 4.70–4.86 (1H, m), 5.11 (2H, s), 7.29–7.–59 (9H m), 7.81–7.89 (2H, m), 8.04–8.09 (1H, m)

Mass (m/z): 607 (M$^+$+1)

(8) N-[1-{3-(1-benzyloxycarbonyl-4-piperidyl)propionyl}-3-piperidyl]-3(S)benzoylamninosuccinamic acid methyl ester IR (Film): 3000, 2940, 2860, 1735, 1680, 1640 cm$^{-1}$ NMR (CDCl$_3$, δ): 0.98–1.24 (2H, m), 1.34–1.95 (9H, m), 2.16–2.40 (2H, m), 2.66–2.83 (3H, m), 3.01–4.00 (6H, m), 4.15 (3H, s), 4.07–4.23 (2H, m), 4.89–5.00 (1H, m), 5.12 (2H, s), 6.88–7.20 (1H, m), 7.31–7.37 (5H, m), 7.43–7.56 (3H, m), 7.78–7.89 (3H, m)

Mass (m/z): 607 (M$^+$+1)

(9) N-[1-{3-(1-benzyloxycarbonyl-4-piperidyl)propionyl}-3-piperidyl]-2(S)-acetylaminosuccinamic acid ethyl ester IR (Film): 3050, 2990, 2920, 2850, 1725, 1650, 1620 cm$^{-1}$ NMR (CDCl$_3$, δ): 1.04–1.24 (2H, m), 1.27–1.28 (total 3H, t, J=7.1 Hz), 1.41–1.99 (9H, m), 2.03 (3H, s), 2.31–2.41 (2H, m), 2.69–3.16 (5H, m), 3.34–4.05 (4H, m), 4.11–4.24 (2H, m), 4.22 (2H, q, J=7.1 Hz), 4.71–4.82 (1H, m), 5.12 (2H, s), 6.02 and 6.09 (total 1H, d, J=7.1 Hz), 6.71–6.88 (1H, m), 7.30–7.37 (5H, m)

Mass (m/z): 559 (M$^+$+1)

(10) N-[(R)-1-{3-(1-benzyloxycarbonyl-4-piperidyl) propionyl}-3-piperidylcarbonyl]-2(R)-acetylamino-β-alanine methyl ester IR (Film): 2940, 2850, 1740, 1650 cm$^{-1}$ NMR (CDCl$_3$, δ): 1.03–1.28 (2H, m), 1.40–1.79 (9H, m), 2.03 (3H, s), 2.20–2.40 (3H, m), 2.64–2.84 (2H, m), 3.20–3.69 (5H, m), 3.75 (3H, s), 3.82–3.89 (1H, m), 4.11–4.23 (2H, m), 4.55–4.68 (1H, m), 5.12 (2H, s), 7.00–7.09 (2H, m), 7.27–7.37 (5H, m)

Mass (m/z): 545 (M$^+$+1)

(11) N-[1-{3-(1-benzyloxycarbonyl-4-piperidyl)propionyl}-3-piperidyl]-3(R)-benzoylaminosuccinamic acid ethyl ester IR (Film): 2990, 2920, 2850, 1720, 1660, 1635 cm$^{-1}$ NMR (CDCl$_3$, δ): 0.96–1.16 (2H, m), 1.30 (3H, t, J=7.2 Hz), 1.40–1.95 (9H, m), 2.10–2.40 (2H, m), 2.63–2.84 (3H, m), 2.99–3.15 (2H, m), 5.22–3.41 (1H, m), 3.54–4.00 (3H, m), 4.09–4.27 (4H, m), 4.86–5.00 (1H, m), 5.13 (2H, s), 6.89–7.20 (1H, m), 7.30–7.37 (5H, m), 7.41–7.55 (3H, m), 7.65–7.84 (3H, m)

Mass (m/z): 621 (M$^+$+1)

(12) 4-[3-{3-(1-tert-butoxycarbonyl-4-piperidyl) propionylamino}-1-piperidyl]-4-oxo-2(S)-benzoylaminobutyric acid tert-butyl ester IR (Film): 3050, 2970, 2930, 2850, 1750, 1640 cm$^{-1}$ NMR (CDCl$_3$, δ): 0.94–1.20 (2H, m), 1.45–1.79 (10H, m), 1.45 (9H, s), 1.46 (9H, s), 2.12–2.39 (7H, m), 2.52–2.80 (3H, m), 3.87–4.36 (4H, m), 7.31–7.58 (4H, m), 7.75–7.85 (2H, m)

Mass (m/z): 615 (M$^+$+1)

EXAMPLE 9

(1) To a mixture of N-[(R)-1-{3-(1-benzyloxycarbonyl-4-piperidyl)propionyl}-3-piperidylcarbonyl]-2(S)-amino-β-alanine ethyl ester hydrochloride (1 g), 3-methoxypropionic acid (0.17 ml) and 1-hydroxybenztriazole (0.24 g) in N,N-dimethylformamide (10 ml) was added 1-ethyl-3-(3-dimethylaminopropyl)carbodiimide (0.33 ml) under stirring at 0° C. After stirring at ambient temperature for overnight, the mixture was poured into water and extracted with ethyl acetate. The extract washed with water, brine and dried over MgSO$_4$, and evaporated in vacuo. The residue was purified by column chromatography on silica gel eluting with (CHCl$_3$:MeOH=100:1) to give N-[(R)-1-{3-(1-benzyloxycarbonyl-4-piperidyl) propionyl}-3-piperidylcarbonyl]-2(S)-(3-methoxypropionyl)amino-β-alanine ethyl ester (0.59 g) as an oil.

IR (Film): 3050, 2980, 2860, 1730, 1660, 1640, 1620 cm$^{-1}$

NMR (CDCl$_3$, δ): 1.05–1.33 (2H, m), 1.28 (3H, t, J=7.2 Hz), 1.42–1.82 (14H, m), 2.11–2.61 (4H, m), 2.67–2.84 (2 h, m), 3.37 (3H, s), 3.40–3.57 (2H, m), 3.61–3.76 (2H, m), 3.85–4.03 (1H, m), 4.12–4.26 (4H, m), 4.67–4.76 and 6.93–7.06 (total 1H, m), 5.12 (2H, s), 7.32–7.39 (6H, m)

Mass (m/z): 603 (M$^+$+1)

The following compounds were obtained according to a similar manner to that of Example 9 (1).

(2) N-[(R)-1-{3-(1-benzyloxycarbonyl-4-piperidyl)propionyl}-3-piperidylcarbonyl]-2(S)-(4-hydroxybenzoylamino)-β-alanine ethyl ester IR (Film): 2930, 1735, 1650, 1630 cm$^{-1}$ NMR (CDCl$_3$, δ): 0.89–1.15 (2H, m), 1.28 (3H, t, J=7.2 Hz), 1.30–1.82 (9H, m), 2.18–2.51 (4H, m), 2.60–2.79 (2H, m), 3.11–3.86 (4H, m), 4.01–4.30 (6H, m), 4.76–4.93 (1H, m), 5.12 (2H, s), 6.79–6.87 (2H, m), 7.29–7.36 (5H, m), 7.50–7.58 and 7.65–7.72 (total 2H, m), 7.83 (1H, d, J=8.6 Hz), 8.25–8.30 and 8.60–8.70 (total 1H, br)

Mass (m/z): 637 (M$^+$+1)

(3) N-[(R)-1-{3-(1-benzyloxycarbonyl-4-piperidyl)propionyl}-3-piperidylcarbonyl]-2(S)-4-biphenylcarbonylamino-β-alanine ethyl ester IR (Film): 2930, 2850, 1735, 1660, 1540 cm$^{-1}$ NMR (CDCl$_3$, δ): 0.90–1.15 (2H, m), 1.30 (3H, t, J=7.1 Hz), 1.34–1.80 (10H, m), 2.29–2.77 (5H, m), 3.13–3.71 (4H, m), 4.02–4.40 (5H, m), 4.93–5.03 (1H, m), 5.09 (2H, s), 7.34 (5H, s), 7.36–7.51 (4H, m), 7.59–7.69 (4H, m), 7.80–7.99 (1H, m), 8.11 (2H, d, J=8.4 Hz)

Mass (m/z): 697 (M$^+$+1)

EXAMPLE 10

(1) A solution of N-[(R)-1-{3-(1-tert-butoxycarbonyl-4-piperidyl)propionyl}-3-piperidylcarbonyl]-3-ethynyl-β-alanine ethyl ester (1.38 g) in tetrahydrofuran (5 ml), ethanol (5 ml) and water (5 ml) was added lithium hydroxide (0.35 g) under stirring at 0° C. After stirring at ambient temperature for 1 hour, the mixture was acidified with 5% KHSO$_4$ aqueous solution and extracted with ethyl acetate. The extract was washed with water, brine and dried over MgSO$_4$, and evaporated in vacuo to give N-[(R)-1-{3-(1-tert-butoxycarbonyl-4-piperidyl)propionyl}-3-piperidylcarbonyl]-3-ethynyl-β-alanine (1.12 g).

IR (Nujol): 3200, 1720, 1630 cm$^{-1}$

NMR (DMSO-d$_6$, δ): 0.68–1.16 (4H, m), 1.21 (9H, s), 1.44–2.29 (9H, m), 2.40–2.60 (5H, m), 2.70–3.08 (2H, m), 3.52–4.28 (5H, m), 4.58–4.75 (1H, m), 8.22–8.29 (1H, m), 12.17–12.31 (1H, br)

Mass (m/z): 464 (M$^+$+1)

The following compounds were obtained according to a similar manner to that of Example 10 (1).

(2) (3R)-N-[(R)-1-{3-(1-tert-butoxycarbonyl-4-piperidyl)propionyl}-3-piperidylcarbonyl]-3-methyl-β-alanine IR (Film): 3410, 2970, 2930, 2880, 1710, 1630 cm$^{-1}$ NMR (DMSO-d$_6$, δ): 0.83–1.90 (5H, m), 1.38 (9H, s), 1.40–1.84 (9H, m), 2.03–2.42 (5H, m), 2.55–2.74 (3H, m), 2.87–3.11 (1H, m), 3.69–4.37 (5H, m), 7.83 (1H, d, J=8.0 Hz)

Mass (m/z): 452 (M$^+$+1)

(3) N-[(R)-1-{3-(1-tert-butoxycarbonyl-4-piperidyl)propionyl}-3-piperidylcarbonyl]-β-alanine IR (Film): 3400, 2910, 1700, 1630 cm$^{-1}$ NMR (DMSO-d$_6$, δ): 0.84–1.09 (2H, m), 1.38 (9H, s), 1.32–1.83 (9H, m), 2.26–2.40 (5H, m), 2.55–2.75 (3H, m), 2.84–3.27 (3H, m), 3.71–3.98 (3H, m), 4.11–4.38 (1H, m), 7.90–8.02 (1H, m)

Mass (m/z) 440 (M$^+$+1)

EXAMPLE 11

(1) To a solution of N-[(R)-1-{3-(1-benzyloxycarbonyl-4-piperidyl)propionyl}-3-piperidylcarbonyl]-2(S)-acetylamino-β-alanine ethyl ester (130 mg) in a mixture of ethanol (1.5 ml) and tetrahydrofuran (1.5 ml) was added a solution of lithium hydroxide (11 mg) in water (1.5 ml) under stirring at 0° C. After stirring at ambient temperature for 1 hour, the mixture was acidified with 10% KHSO$_4$ aqueous solution and extracted with ethyl acetate. The extract was washed with water, brine and dried over MgSO$_4$ and evaporated in vacuo to give N-[(R)-1-{3-(1-benzyloxycarbonyl-4-piperidyl)propionyl}-3-piperidylcarbonyl]-2(S)-acetylamino-β-alanine as an oil (67 mg).

IR (Film): 3810, 3000, 2950, 2880, 1730, 1655 cm$^{-1}$

NMR (DMSO-d$_6$, δ): 0.80–1.09 (2H, m), 1.24–1.80 (10H, m), 1.99 (3H, s), 2.05–2.36 (3H, m), 2.56–3.51 (6H, m), 3.74–3.83 (1H, m), 3.94–4.04 (2H, m), 4.16–4.40 (2H, m), 5.06 (2H, s), 7.30–7.37 (5H, m), 7.95–8.09 (2H, m)

Mass (m/z): 531 (M$^+$+1)

The following compounds were obtained according to a similar manner to that of Example 11 (1).

(2) N-[(R)-1-{3-(1-tert-butoxycarbonyl-4-piperidyl)propionyl}-3-piperidylcarbonyl]-3(R)-phenethyl-β-alanine IR (Film): 3400, 2920, 2850, 1700, 1640 cm$^{-1}$ NMR (DMSO-d$_6$, δ): 0.63–0.86 (2H, m), 1.17 (9H, s), 1.17–1.29 (8H, m), 1.26–1.66 (5H, m), 2.04–2.18 (4H, m), 2.30–2.54 (5H, m), 3.49–3.90 (4H, m), 3.95–4.23 (1H, m), 6.94–7.09 (5H, m), 7.65 (1H, d, J=8 Hz)

Mass (m/z): 544 (M$^+$+1)

(3) N-[(R)-1-{2-(4-piperidyloxy)acetyl}-3-piperidylcarbonyl]-3(S)-ethynyl-β-alanine trifluoroacetate

[α]$_D^{20}$=−19.11° (C=1.0, MeOH)

IR (Film): 3360, 2940, 1760, 1710, 1625 cm$^{-1}$

NMR (DMSO-d$_6$, δ): 1.22–2.36 (8H, m), 2.59 (1H, d, J=6.6 Hz), 2.49–2.74 (1H, m), 2.84–3.21 (6H, m), 3.57–3.70 (2H, m), 4.03–4.26 (3H, m), 4.77–4.88 (4H, m), 8.31–8.43 (2H, m)

Mass (m/z): 366 (M$^+$+1) free of compound and

N-[(R)-1-{2-(4-piperidyloxy)acetyl}-3-piperidylcarbonyl]-3(R)-ethynyl-β-alanine trifluoroacetate IR (Film): 3250, 2920, 1710, 1625 cm$^{-1}$ NMR (DMSO-d$_6$, δ): 1.20–2.00 (6H, m), 2.11–2.76 (3H, m), 2.58 (1H, d, J=7.4 Hz), 2.86–3.23 (6H, m), 3.95–4.32 (8H, m), 4.75–4.89 (1H, m), 8.42 (2H, t, J=8.6 Hz)

Mass (m/z): 366 (M$^+$+1) free of compound (4) N-[(R)-1-{3-(1-tert-butoxycarbonyl-4-piperidyl)propionyl}-3-piperidylcarbonyl[-2-piperidylacetic acid IR (Film): 3410, 2930, 2850, 1710, 1680, 1610 cm$^{-1}$ NMR (DMSO-d$_6$, δ): 0.83–1.07 (3H, m), 1.34–1.71 (11H, m), 1.38 (9H, s), 2.25–2.40 (3H, m), 2.55–3.14 (9H, m), 3.68–3.97 (4H, m), 4.27–4.39 (2H, m), 4.45–4.58 (1/3H, m), 4.88–5.03 (2/3H, m)

Mass (m/z): 494 (M$^+$+1)

(5) N-[(R)-1-{3-(4-tert-butoxycarbonyl-4-piperidyl)propionyl}-3-piperidylcarbonyl]-2(S)-benzoylamino-β-alanine IR (Film): 2930, 1720, 1650, 1635 cm$^{-1}$ NMR (DMSO-d$_6$, δ): 0.83–1.06 (2H, m), 1.25–1.44 (4H, m), 1.38 (9H, s), 1.54–1.86 (5H, m), 2.15–2.33 (3H, m), 2.56–2.73 (2H, m), 2.90–3.10 (1H, m), 3.39–3.98 (6H, m), 4.08–4.59 (2H, m), 7.45–7.56 (3H, m), 7.83–7.87 (2H, m), 8.13–8.23 (1H, m) 8.60–8.66 (1H, m)

Mass (m/z): 559 (M$^+$+1)

(6) N-[(R)-1-{3-(1-tert-butoxycarbonyl-4-piperidyl)propionyl}-3-piperidylcarbonyl]-2(S)-phenylsulfonylamino-β-alanine IR (Nujol): 3370, 3250, 3180, 1700, 1685, 1640 cm$^{-1}$ NMR (DMSO-d$_6$, δ): 0.80–1.06 (2H, m), 1.14–1.43 (6H, m), 1.38 (9H, s), 1.55–1.71 (3H, m), 1.88–2.34 (3H, m), 2.42–2.71 (2H, m), 2.83–3.14 (2H, m), 3.23–3.40 (2H, m), 3.71–3.97 (4H, m), 4.14–4.40 (1H, m), 7.50–7.68 (3H, m), 7.75–7.79 (2H, m), 7.95–8.06 (1H, m), 8.16 (1H, t, J=8.6 Hz), 12.66–12.80 (1H, br)
Mass (m/z): 595 (M$^+$+1)

(7) N-[(R)-1-{3-(1-tert-butoxycarbonyl-4-piperidyl)propionyl}-3-piperidylcarbonyl]-2(S)-n-butansulfonylamino-β-alanine
IR (Nujol): 3330, 3250, 1715, 1690, 1640
NMR (DMSO-d$_6$, δ): 0.87 (3H, t, J=7.3 Hz), 0.84–1.07 (2H, m), 1.30–1.46 (7H, m), 1.38 (9H, s), 1.57–1.90 (7H, m), 2.29–2.36 (2H, m), 2.55–2.75 (3H, m), 2.85–3.50 (3H, m), 2.96 (2H, t, J=7.7 Hz), 3.77–4.01 (4H, m), 4.19–4.42 (1H, m), 7.50–7.57 (1H, m), 8.02–8.11 (1H, m), 12.93–13.00 (1H, br)
Mass (m/z): 475 (M$^+$+1-Boc)

(8) N-[(R)-1-{3-(1-tert-butoxycarbonyl-4-piperidyl)propionyl}-3-piperidylcarbonyl]-3(S)-ethynryl-β-alanine
IR (KBr): 3430, 3300, 1731, 1686, 1662 cm$^{-1}$
NMR (DMSO-d$_6$, δ): 0.92–1.17 (2H, m), 1.38 (9H, s), 1.49–1.77 (9H, m), 1.91, 1.99 (total 1H, s), 2.13–2.64 (8H, m), 2.89–3.06 (1H, m), 3.17–3.28 (1H, m), 3.76–4.32 (3H, m), 4.78–4.84 (1H, m), 8.37–8.44 (1H, m), 12.39 (1H, br)

(9) N-[(R)-1-{3-(1-tert-butoxycarbonyl-4-piperidyl)propionyl}-3-piperidylcarbonyl]-3(S)-propargylaminocarbonyl-β-alanine
IR (Film): 3380, 1710, 1640 cm$^{-1}$
NMR (DMSO-d$_6$, δ): 0.85–1–08 (2H, m), 1.38 (9H, s), 1.42–1.91 (8H, m), 2.26–2–37 (3H, m), 2.54–2.76 (6H, m), 2.88–3.12 (2H, m), 3.69–3.98 (5H, m), 4.08–4.37 (1H, m), 4.46–4.57 (1H, m), 7.18–7.33 (1H, m), 8.08–8.18 (1H, m), 8.31–8.36 (1H, m)
Mass (m/z): 521 (M$^+$+1)

(10) N-[(S)-1-{3-(1-tert-butoxycarbonyl-4-piperidyl)propionyl}-3-piperidylcarbonyl]-3-ethynyl-β-alanine
IR (Film): 3000, 2930, 2870, 1720, 1640 cm$^{-1}$
NMR (DMSO-d$_6$, δ): 0.85–1.10 (2H, m), 1.38 (9H, s), 1.21–1.86 (8H, m), 2.08–2.40 (3H, m), 2.56–2.71 (4H, m), 2.87–3.12 (3H, m), 3.21 (1H, dd, J=5.4 and 2.3 Hz), 3.71–4.43 (4H, m), 4.74–4.87 (1H, m), 8.39–8.46 (1H, m), 12.40–12.50 (1H, br)
Mass (m/z): 464 (M$^+$+1)

(11) N-[(S)-1-{2-(1-benzyloxycarbonyl-4-piperidyloxy)acetyl}-3-piperidylcarbonyl]-β-alanine
IR (Film): 3300, 2930, 1720, 1620 cm$^{-1}$
NMR (DMSO-d$_6$, δ): 1.32–1.91 (8H, m), 2.06–2.30 (1H, m), 2.36 (2H, t, J=6.9 Hz), 2.57–2.71 (1H, m), 2.85–3.29 (5H, m), 3.47–3.79 (4H, m), 4.01–4.33 (3H, m), 5.06 (2H, s), 7.30–7.37 (5H, m), 7.93–8.01 (1H, br), 12.15–12.30 (1H, br)
Mass (m/z): 476 (M$^+$+1)

(12) N-[(R)-1-{3-(1-benzyloxycarbonyl-4-piperidyl)propionyl}-3-piperidylcarbonyl}-2(S)-(4-chlorobenzoyl)amino-β-alanine
IR (Film): 3400, 1720, 1635, 1600 cm$^{-1}$
NMR (DMSO-d$_6$): 0.87–1–19 (2H, m), 1.31–1.44 (3H, m), 1.53–1.85 (4H, m), 2.12–2.34 (2H, m), 2.59–2.83 (11H, m), 3.93–4.05 (2H, m), 4.14–4.58 (1H, m), 5.05 (2H, s), 7.29–7.40 (5H, m), 7.57 (2H, d, J=8.5 Hz), 7.82–7.89 (2H, m), 8.11–8.20 (1H, m), 8.66–8.74 (1H, m)
Mass (m/z): 627 (M$^+$+1)

(13) N-[(R)-1-{3-(1-benzyloxycarbonyl-4-piperidyl)propionyl}-3-piperidylcarbonyl]-2(S)-(4-methoxybenzoylamino)-β-alanine
IR (Film): 3350, 2920, 1715, 1630, 1600 cm$^{-1}$
NMR (DMSO-d$_6$, δ): 0.85–1.84 (12H, m), 2.07–2.44 (3H, m), 2.56–3.23 (5H, m), 3.37–3.75 (2H, m), 3.81 (3H, s), 3.91–4.08 (2H, m), 4.14–4.56 (1H, m), 5.05 (2H, s), 7.01 (2H, d, J=8.8 Hz), 7.30–7.37 (5H, m), 7.83 (2H, d, J=8.7 Hz), 8.11–8.19 (1H, m), 8.42–8.49 (1H, m), 12.68–12.75 (1H, br)
Mass (m/z): 623 (M$^+$+1)

(14) N-[1-{3-(1-benzyloxycarbonyl)-4-piperidyl)propionyl}-3-piperidyl]-2(S)-benzoylaminosuccinamic acid
IR (Film): 3250, 2900, 1710, 1635 cm$^{-1}$
NMR (DMSO-d$_6$, δ): 0.84–1.05 (2H, m), 1.31–1.47 (5H, m), 1.57–1.83 (4H, m), 2.15–2.35 (2H, m), 2.62–2.82 (4H, m), 2.94–3.09 (2H, m), 3.50–3:82 (3H, m), 3.90–4.03 (2H, m), 4.69–4.81 (1H, m), 5.05 (2H, s), 7.33–7.40 (5H, m), 7.44–7.57 (3H, m), 7.83–8.05 (3H, m), 8.58–8.68 (1H, m)
Mass (m/z): 593 (M$^+$+1)

(15) N-[(R)-1-{3-(1-benzyloxycarbonyl-4-piperidyl)propionyl}-3-piperidylcarbonyl]-2(S)-cyclopropylcarbonylamino-β-alanine
IR (Film): 3300, 3000, 2930, 2860, 1720, 1640 cm$^{-1}$
NMR (DMSO-d$_{61}$, δ): 0.66 (4H, d, J=6.5 Hz), 0.89–1.10 (2H, m), 1.21–1.87 (10H, m), 2.07–2.37 (3H, m), 2.58–3.55 (6H, m), 3.71–3.84 (1H, m), 3.94–4.05 (2H, m), 4.17–4.40 (2H, m), 5.06 (2H, s), 7.35–7.39 (5H, m), 7.96–8.06 (1H, m), 8.24–8.31 (1H, m), 12.63–12.71 (1H, br)
Mass (m/z): 557 (M$^+$+1)

(16) N-[(R)-1-{3-(1-benzyloxycarbonyl-4-piperidyl)propionyl}-3-piperidylcarbonyl]-2(S)-(3-methoxypropionyl)amino-β-alanine
IR (Film): 3480, 2920, 1710, 1640 cm$^{-1}$
NMR (DMSO-d$_6$, δ): 0.94–1.29 (2H, m), 1.37–1.84 (11H, m), 2.06–2.40 (2H, m), 2.36 (2H, t, J=6.5 Hz), 2.56–3.04 (3H, m), 3.20 (3H, s), 3.36–3.55 (2H, m), 3.51 (2H, t, J=6.5 Hz), 3.73–3.83 (1H, m), 3.94–4.06 (2H, m), 4.18–4.39 (2H, m), 5.05 (2H, s), 7.35 (5H, s), 7.90–8.09 (2H, m)
Mass (m/z): 575 (M$^+$+1)

(17) N-[(R)-1-{3-(1-benzyloxycarbonyl-4-piperidyl)propionyl}-3-piperidylcarbonyl]-2(S)-(4-hydroxybenzoyl)amino-β-alanine
IR (Nujol): 3250, 1720, 1630, 1600 cm$^{-1}$
NMR (DMSO-d$_6$, δ): 0.89–1.86 (12H, m), 2.11–2.34 (3H, m), 2.51–3.09 (4H, m), 3.45–3.84 (2H, m), 3.95–4.05 (2H; m), 4.12–4.54 (2H, m), 5.06 (2H, s), 6.82 (2H, d, J=6.8 Hz), 7.30–7.39 (5H, m), 7.72 (2H, d, J=7.2 Hz), 8.10–8.19 (1H, m), 8.32–8.39 (1H, m), 10.02 (1H, s), 12.65–12.74 (1H, br)
Mass (m/z): 609 (M$^+$+1)

(18) N-[1-{3-(1-benzyloxycarbonyl-4-piperidyl)propionyl{-3-piperidyl]-2(S)-acetylaminosuccinamic acid
IR (Film): 3270, 2900, 1720, 1640 cm$^{-1}$
NMR (DMSO-d$_6$, δ): 0.90–1.12 (2H, m), 1.29–1.52 (5H, m), 1.61–1.80 (4H, m), 1.82 (3H, s), 1.92–2.36 (2H, m), 2.44–3.08 (5H, m), 3.17–3.87 (3H, m), 3.94–4.05 (3H, m), 4.39–4.59 (1H, m), 5.05 (2H, s), 7.23–7.39 (6H, m), 7.76–8.13 (1H, m)
Mass (m/z): 531 (M$^+$+1)

(19) N-[1-{3-(1-benzyloxycarbonyl-4-piperidyl)propionyl}-3-piperidyl]-3(R)-benzoylaminosuccinamic acid
IR (Film): 3280, 2910, 2850, 1715, 1640 cm$^{-1}$
NMR (DMSO-d$_6$, δ): 0.85–1.05 (2H, m), 1.22–1.50 (5H, m), 1.54–1.83 (4H, m), 2.11–2.35 (2H, m), 2.55–2.83 (4H, m), 2.90–3.06 (2H, m), 3.17–3.76 (3H, m), 3.88–4.05 (2H, m), 4.67–4.80 (1H, m), 5.05 (2H, s), 7.33 (5H, s), 7.40–7.54 (3H, m), 7.82–7.90 (2H, m), 7.92–8.11 (1H, m), 8.60–8.69 (1H, m)
Mass (m/z): 593 (M$^+$+1)

(20) N-[(R)-1-{3-(1-benzyloxycarbonyl-4-piperidyl)propionyl}-3-piperidylcarbonyl]-2(S)-(4-biphenylcarbonylamino)-β-alanine
IR (Film): 3300, 2940, 1730, 1690, 1660, 1640 cm$^{-1}$
NMR (DMSO-d$_6$, δ): 0.86–1.05 (2H, m), 1.11–1.45 (4H, m), 1.54–1.88 (6H, m), 2.05–2.34 (3H, m), 2.58–3.11 (3H, m), 3.23–3.80 (4H, m), 3.90–4.57 (3H, m), 5.05 (2H, s), 7.34 (5H, s), 7.40–7.55 (3H, m), 7.72–7.82 (4H, m), 7.93–7.99 (2H, m), 8.14–8.23 (1H, m), 8.64–8.71 (1H, m)

Mass (m/z): 669 (M$^+$+1)

(21) N-[(R)-1-{3-(1-benzyloxycarbonyl-4-piperidyl)-propionyl}-3-piperidylcarbonyl]-2(S)-(n-hexanoyl)amino-]-alanine IR (Film): 3350, 3000, 2930, 2860, 1700, 1640 cm$^{-1}$ NMR (DMSO-d$_6$, δ): 0.85 (3H, t, J=6.6 Hz), 0.90–1.09 (2H, m), 1.14–1.29 (5H, m), 1.39–1.85 (10H, m), 2.09 (2H, t, J=7.4 Hz), 2.28–2.36 (2H, m), 2.57–3.54 (7H, m), 3.71–3.84 (1H, m), 3.94–4.06 (2H, m), 4.17–4.40 (2H, m), 5.06 (2H, s), 7.30–7.42 (5H, m), 7.90–8.03 (2H, m)

Mass (m/z): 587 (M$^+$+1)

(22) N-[(R)-1-{3-(1-tert-butoxycarbonyl-4-piperidyl)propionyl}-3-piperidylcarbonyl]-2(S)-acetylamino-β-alanine IR (Film): 3280, 2960, 2920, 1720, 1650 cm$^{-1}$ NMR (DMSO-d$_6$, δ): 0.83–1.09 (2H, m), 1.38 (9H, s), 1.38–1.80 (9H, m), 1.84 (3H, s), 2.07–2.39 (3H, m), 2.51–3.22 (6H, m), 3.73–4.40 (5H, m), 7.96–8.10 (2H, m)

Mass (m/z): 497 (M$^+$+1)

EXAMPLE 12

(1) To a solution of N-[1-{2-(1-benzyloxycarbonyl4-piperidyloxy)acetyl}-3-piperidylcarbonyl]-β-alanine methyl ester (1.33 g) in methanol (10 ml), H$_2$O (10 ml) and tetrahydrofuran (10 ml) was added 1N NaOH (8.55 ml) under stirring at 0° C. After stirring at ambient temperature for 3 hours, the mixture was acidified with 10% KHSO$_4$ aqueous solution, and extracted with ethyl acetate. The extract was washed with water and brine, and dried over MgSO$_4$, and evaporated in vacuo to give N-[1-{2-(1-benzyloxycarbonyl-4-piperidyloxy)acetyl}-3-piperidylcarbonyl]-β-alanine (1.22 g) as an oil.

IR (Film): 3330, 2940, 1700, 1630 cm$^{-1}$

NMR (DMSO-d$_6$, δ): 1.25–1.90 (8H, m), 2.09–2.31 (1H, m), 2.36 (2H, t, J=6,9 Hz), 2.56–2.70 (1H, m), 2.85–3.29 (5H, m), 3.50–3.84 (4H, m), 4.10–4.34 (3H, m), 5.06 (2H, s), 7.28–7.39 (5H, m), 7.91–8.03 (1H, m), 12.09–12.10 (1H, br)

Mass (m/z): 476 (M$^+$+1)

The following compounds were obtained according to a similar manner to that of ExamPle 12(1).

(2) N-[2-[1-{3-(1-Benzyloxycarbonyl-4-piperidyl)propionyl}-3-piperidyl]acetyl]glycine IR (Film): 3400, 2920, 2850, 1660, 1640, 1620 cm$^{-1}$ NMR (DMSO-d$_6$, δ): 0.84–1.50 (7H, ), 1.52–1.94 (5H, m), 2.03 (2H, t, J=7.9 Hz), 2.22–2.41 (2H, m), 2.61–3.03 (4H, m), 3.67–3.88 (1H, m), 3.73 (2H, d, J=5.3 Hz), 3.98–4.28 (3H, m), 5.06 (2H, s), 7.28–7.42 (5H, m), 8.14–8.29 (1H, m), 12.20–12.37 (1H, br)

Mass (m/z): 472 (M$^+$+1)

(3) N-[1-{3-(1-Benzyloxycarbonyl-4-piperidyl)propionyl-3-piperidylcarbonyl]-3-methyl-β-alanine IR (Film): 3380, 2910, 2850, 1660, 1615 cm$^{-1}$ NMR (DMSO-d$_6$, δ): 0.88–1.13 (5H, m), 1.24–1.51 (4H, m), 1.51–1.83 (5H, m), 2.03–2.43 (5H, m), 2.55–3.18 (4H, m), 3.68–3.89 (1H, m), 3.90–4.40 (4H, m), 5.06 (2H, s), 7.35–7.39 (5H, m), 7.83 (1H, d, J=7.9 Hz)

Mass (m/z): 488 (M$^+$+1)

(4) N-[1-{3-(1-benzyloxycarbonyl-4-piperidyl)propionyl}-(1,2,3,4-tetrahydro-3-quinolyl)carbonyl]-β-alanine IR (Film): 3410, 3940, 1760, 1650, 1635 cm$^{-1}$ NMR (DMSO-d$_6$, δ): 0.85–1.06 (2H, m), 1.43–2.20 (6H, m), 2.39 (2H, t, J=6.9 Hz), 2.88–2.84 (4H, m), 3.23–3.32 (2H, m), 3.55–3.99 (5H, m), 5.05 (2H, s), 5.53–5.61 (1H, m), 7.09–7.23 (4H, m), 7.30– 7.42 (5H, m), 8.10–8.18 (1H, m)

Mass (m/z): 522 (M#+1)

EXAMPLE 13

(1) A solution of N-[1-{3-(1-tert-butoxycarbonyl-4-piperidyl)propionyl}-3-piperidylcarbonyl]-β-alanine methyl ester (2.03 g) in methanol (10 ml) and water (10 ml) was added lithium hydroxide (0.56 g) under stirring at 0° C. After stirring at ambient temperature for 1 hour, the mixture was acidified with 5% KHSO$_4$ aqueous solution and extracted with ethyl acetate. The extract was washed with water, brine and dried over MgSO$_4$, and evaporated in vacuo to give N-[1-{3-(1-tert-butoxycarbonyl-4-piperidyl)propionyl}-3-piperidylcarbonyl]-β-alanine as an oil (1.62 g).

IR (Film): 3300, 2920, 1715, 1630 cm$^{-1}$

NMR (DMSO-d$_6$, δ): 0.83–1.07 (2H, m), 1.38 (9H, s), 1.42–1.83 (9H, m), 2.26–2.40 (4H, m), 2.52–2.74 (2H, m), 2.87–3.27 (5H, m), 3.70–3.95 (3H, m), 4.16–4.38 (1H, m), 7.92–8.02 (1H, my, 12.05–12.10 (1H, br)

Mass (m/z): 440 (M$^+$+1)

The following compounds were obtained according to a similar manner to that of Example 13 (1).

(2) N-[1-{3-(1-tert-butoxycarbonyl-4-piperidyl)propionyl}-4-piperidylcarbonyl]-β-alanine IR (Film): 3400, 3050, 2910, 1720, 1610 cm$^{-1}$ NMR (DMSO-d$_6$, δ): 0.80–1.07 (2H, m), 1.23–1.46 (6H, m), 1.38 (9H, s), 1.55–1.71 (4H, m), 2.27–2.36 (3H, m), 2.36 (2H, t, J=6.9 Hz), 2.46–2.75 (2H, m), 2.89–3.05 (1H, m), 3.22 (2H, q, J=5.9 Hz), 3.78–3.99 (3H, m), 4.28–4.40 (1H, m), 7.89 (1H, t, J=5.5 Hz)

Mass (m/z): 438 (M$^+$−1)

(3) N-[1-{4-(1-tert-butoxycarbonyl-4-piperidyl)butyryl}-3-piperidylcarbonyl]glycine IR (Film): 3390, 2920, 2850, 1720, 1650 cm$^{-1}$ NMR (DMSO-d$_6$, δ): 0.84–1.10 (2H, m), 1.18–1.29 (2H, m), 1.38 (9H, s), 1.46–1.91 (8H, m), 2.24–2.38 (3H, m), 2.59–3.20 (4H, m), 3.69–4.00 (6H, m), 4.12–4.28 and 4.38–4.49 (total 1H, m), 8.25 (1H, t, J=5.8 Hz)

Mass (m/z): 440 (M$^+$+1)

(4) N-[(R)-1-{3-(1-tert-butoxycarbonyl-4-piperidyl)propionyl}-3-piperidylcarbonyl]-3(R)-(4-methoxyphenethyl)-β-alanine IR (Film): 3400, 3930, 3860, 1700, 1630 cm$^{-1}$ NMR (DMSO-d$_6$, δ): 0.85–1.09 (2H, m), 1.25–1.49 (4H, m), 1.38 (9H, s), 1.39–1.88 (8H, m), 2.10–2.72 (9H, m), 2.89–3.16 (1H, m), 3.71 (3H, s), 3.77–4.06 (4H, m), 4.12–4.39 (1H, m), 6.82 (2H, d, J=8.6 Hz), 7.07 (2H, d, J=8.6 Hz), 7.83 (1H, d, J=8.4 Hz), 12.08 (1H, s)

Mass (m/z): 574 (M$^+$+1)

(5) N-[(R)-1-{3-(1-tert-butoxycarbonyl-4-piperidyl)propionyl{-3-piperidylcarbonyl]-3-phenyl-β-alanine IR (Film): 3380, 3020, 2940, 2870, 1710, 1660, 1630 cm$^{-1}$ NMR (DMSO-d$_6$, δ): 0.86–1.06 (2H, m), 1.21–1.91 (9H, m), 1.38 (9H, s), 2.16–2.35 (3H, m), 2.58–2.67 (5H, m), 2.86–3.06 (1H, m), 3.63–3.97 (3H, m), 4.05–4.42 (1H, m), 5.11–5.23 (1H, m), 7.17–7.31 (5H, m), 8.40–8.47 (1H, m)

Mass (m/z): 516 (M$^+$+1)

(6) N-[(R)-1-{3-(1-tert-butoxycarbonyl-4-piperidyl)propionyl}-3-piperidylcarbonyl]-3(R)-(3,4-dimethoxyphenethyl)-β-alanine IR (Film): 3300, 3430, 3360, 1720, 1640, 1625 cm$^{-1}$ NMR (DMSO-d$_6$, δ): 0.83–1.10 (2H, m), 1.21–1.46 (4H, m), 1.38 (9H, s), 1.61–1.91 (8H, m), 2.07–2.73 (10H, m), 2.87–3.20 (2H, m), 3.70 (3H, s), 3.73 (3H, s), 3.76–4.08 (3H, m), 6.64–6.68 (1H, m), 6.74–6.85 (2H, m), 7.83 (1H, d, J=8.2 Hz), 11.97–12.14 (1H, br)

Mass (m/z): 604 (M$^+$+1)

(7) N-[(R)-1-{3-(1-tert-butoxycarbonyl-4-piperidyl)propionyl}-3-piperidylcarbonyl]-3(R)-(3-methoxyphenethyl)-β-alanine NMR (DMSO-d$_6$, δ): 0.92–1.12 (2H, m), 1.38 (9H, s), 1.38–1.98 (13H, m), 2.03–3.20 (14H, m), 3.72 (3H, s), 3.75–4.38 (6H, m), 6.73 (3H, d, J=6.0 Hz), 7.17 (1H, t, J=8.3 Hz), 7.84 (1H, d, J=8.6 Hz)

Mass (m/z): 574 (M$^+$+1)

(8) N-[(R)-1-{3-(1-tert-butoxycarbonyl-4-piperidyl)propionyl}-3-piperidylcarbonyl]-3(R)-(3-trifluoromethylphenethyl)-β-alanine IR (Film): 3280, 2920, 2850, 1720, 1630 cm$^{-1}$ NMR (DMSO-d$_6$, δ): 0.86–1.09 (2H, m), 1.38 (9H, s), 1.30–1.44 (4H, m), 1.59–1.86 (6H, m), 2.28–2.40 (5H, m), 2.60–2.74 (5H, m), 2.82–3.14 (1H, m), 3.71–4.05 (5H, m), 4.15–4.40 (1H, m), 7.48–7.56 (4H, m), 7.85–7.90 (1H, m)

Mass (m/z): 612 (M$^+$+1)

(9) N-[(R)-1-{3-(1-tert-butoxycarbonyl-4-piperidyl)propionyl}-3-piperidylcarbonyl]-3(R)-(2-methoxyphenethyl)-β-alanine IR (Film): 3290, 3000, 2930, 2850, 1715, 1640, 1615 cm$^{-1}$ NMR (DMSO-d$_6$, δ): 0.84–1.08 (2H, m), 1.30–1.45 (4H, m), 1.38 (9H, s), 1.59–1.91 (7H, m), 2.09–2.74 (10H, m), 2.89–3.18 (1H, m), 3.71–4.02 (4H, m), 3.75 (3H, s), 4.16–4.39 (1H, m), 6.81–6.94 (2H, m), 7.07–7.20 (2H, m), 7.84 (1H, d, J=8.5 Hz), 12.12 (1H, s)

Mass (m/z): 574 (M$^+$+1)

(10) N-[(R)-1-{$^3$-(1-tert-butoxycarbonyl-4-piperidyl)propionyl}-3-piperidylcarbonyl]-3(R)-(3,4-methylenedioxyphenethyl)-β-alanine IR (Film): 3380, 2960, 2920, 2860, 1710, 1650, 1620 cm$^{-1}$ NMR (DMSO-d$_6$, δ): 0.86–1.07 (2H, m), 1.24–1.94 (5H, m), 1.38 (9H, s), 1.59–1.87 (7H, m), 2.30–2.70 (9H, m), 2.90–3.15 (1H, m), 3.70–4.00 (4H, m), 4.14–4.39 (1H, m), 5.95 (2H, s), 6.59–6.63 (1H, m), 6.74–6.81 (2H, m), 7.83 (1H, d, J=8.3 Hz), 12.09–12.19 (1H, br)

Mass (m/z): 588 (M$^+$+1)

(11) N-[(R)-1-{3-(1-benzyloxycarbonyl-4-piperidyl)propionyl}-3-piperidylcarbonyl]-2(R)-benzoylamino-β-alanine IR (Film): 3260, 2900, 1710, 1630 cm$^{-1}$ NMR (DMSO-d$_6$, δ): 0.86–1.04 (2H, m), 1.23–1.45 (4H, m), 1.56–1.83 (5H, m), 2.12–2.36 (3H, m), 2.57–3.81 (7H, m), 3.91–4.04 (2H, m), 4.14–4.62 (2H, m), 5.05 (2H, s), 7.28–7.35 (5H, m), 7.47–7.63 (3H, m), 7.83–7.97 (2H, m), 8.15–8.23 (1H, m), 8.64 (1H, t, J=7.1 Hz)

Mass (m/z): 593 (M$^+$+1)

(12) N-[1-{3-(1-benzyloxycarbonyl-4-piperidyl)propionyl}-3-piperidyl]-3(S)-benzoylaminosuccinamic acid IR (Film): 3290, 2930, 1745, 1640 cm$^{-1}$ NMR (DMSO-d$_6$, δ): 0.87–1.06 (2H, m), 1.32–1.83 (9H, m), 2.15–2.35 (3H, m), 2.58–3.07 (8H, m), 3.51–3.79 (2H, m), 3.87–4.03 (2H, m), 4.67–4.80 (1H, m), 5.05 (2h, s), 7.29–7.39 (5H, m), 7.45–7.56 (3H, m), 7.81–7.89 (2H, m), 8.57–8.68 (1H, m)

Mass (m/z): 593 (M$^+$+1)

(13) N-[(R)-1-{3-(1-benzyloxycarbonyl-4-piperidyl)propionyl}-3-piperidylcarbonyl]-2(R)-acetylamino-β-alanine IR (Film): 3400, 2930, 2860, 1720, 1655, 1630 cm$^{-1}$ NMR (DMSO-d$_6$, δ): 0.90–1.12 (2H, m), 1.23–1.79 (9H, m), 1.84 (3H, s), 2.11–2.40 (4H, m), 2.61–3.48 (5H, m), 3.74–3.88 (1H, m), 3.96–4.08 (2H, m), 4.20–4.40 (2H, m), 5.06 (2H, s), 7.28–7.42 (5H, m), 7.98–8.08 (2H, m)

Mass (m/z): 531 (M$^+$+1)

The following compound was obtained according to a similar manner to that of Example 12 (1).

EXAMPLE 14

(1) N-[2-[1-{2-(1-tert-butoxycarbonyl-4-piperidyl)acetyl}-3-piperidyl]acetyl]-β-alanine IR (Film): 3300, 2920, 2850, 1710, 1635 cm$^{-1}$ NMR (DMSO-d$_6$, δ): 0.87–1.31 (4H, m), 1.38 (9H, s), 1.55–2.06 (9H, m), 2.14–2.28 (2H, m), 2.37 (2H, t, J=6.8 Hz), 2.60–3.02 (4H, m), 3.23 (2H, q, J=6.0 Hz), 3.68–4.27 (4H, m), 7.91–8.03 (1H, m)

Mass (m/z): 438 (M$^+$−1)

(2) N-[2-[1-{2-(1-tert-butoxycarbonyl-4-piperidylidene)acetyl}-3-piperidyl]acetyl]-β-alanine IR (Film): 3200, 2925, 1680, 1650 cm$^{-1}$ NMR (DMSO-d$_6$, δ): 1.09–1.41 (3H, m), 1.41 (9H, s), 1.57–1.91 (4H, m), 1.96–2.00 (2H, m), 2.14–2.24 (2H, m), 2.28–2.40 (3+1/2H, m), 2.64–2.83 (1H, m), 2.91–3.06 (1/2H, m), 3.19–3.46 (5H, m), 3.71–3.83 (1H, m), 4.02–4.26 (1H, m), 5.90 and 5.96 (total 1H, s), 7.69–8.03 (1H, m), 12.17–12.24 (1H, br)

Mass (m/z): 438 (M$^+$+1)

(3) 4-[3-{3-(1-tert-butoxycarbonyl-4-piperidyl)propionylamino}-1-piperidyl]-4-oxo-butyric acid IR (Film): 3250, 2920, 1710, 1660, 1640, 1620 cm$^{-1}$ NMR (DMSO-d$_6$, δ): 0.82–1.04 (2H, m), 1.38 (9H, s), 1.38–1.85 (11H, m), 1.99–2.11 (2H, m), 2.41–2.43 (3H, m), 2.56–2.76 (2H, m), 2.98–3.12 (1H, m), 3.60–3.76 and 4.09–4.20 (total 3H, m), 3.85–3.96 (2H, m), 7.73, 7.84 (total 1H, d, J=8.0 and 6.4 Hz), 12.03 (1H, s)

Mass (m/z): 440 (M$^+$+1)

(4) N-[4-{3-(1-tert-butoxycarbonyl-4-piperidyl)propionyl}-2-morpholinylcarbonyl]-β-alanine IR (Film): 3400, 2980, 2920, 2880, 1710, 1640 cm$^{-1}$ NMR (DMSO-d$_6$, δ): 0.84–1.08 (2H, m), 1.38 (9H, s), 1.38–1.49 (3H, m), 1.59–1.70 (4H, m), 2.29–2.44 (1H, m), 2.40 (2H, t, J=7.0 Hz), 2.58–2.92 (3H, m), 3.09–3.56 (3H, m), 3.70–3.98 (5+1/2H, m), 4.41–4.51 (1/2H, m), 7.77–7.94 (1H, m)

Mass (m/z): 440 (M$^+$−1)

(5) N-[1-{3-(1-tert-Butoxycarbonyl-4-piperidyl)propionyl}-3-piperidyl]succinamic acid IR (Film): 3400, 1710, 1680, 1630 cm$^{-1}$ NMR (DMSO-d$_6$, δ): 0.84–1.06 (2H, m), 1.26–1.31 (6H, m), 1.38 (9H, s), 1.59–1.84 (4H, m), 2.20–2.46 (6H, m), 2.57–2.74 (2H, m), 2.91–3.08 (2H, m), 3.45–3.76 (2H, m), 3.84–3.96 (2H, m), 7.76–7.92 (1H, m), 12.00–12.06 (1H, br)

Mass (m/z): 340 (M$^+$+1-Boc)

(6) N-[(R)-1-{2-(4-piperidyloxy)acetyl}-3-piperidylcarbonyl]-β-alanine trifluoroacetate $[a]_D^{20}$=20.07° (C=1.0, MeOH)

IR (Film): 2940, 1760, 1820, 1660, 1630 cm$^{-1}$

NMR (DMSO-d$_6$, δ) 1.25–2.02 (8H, m), 2.10–2.16 (1H, m), 2.37 (2H, t, J=6.8 Hz), 2.55–2.71 (1H, m), 2.86–3.25 (7H, m), 3.59–3.72 (2H, m), 4.07–4.31 (3H, m), 7.99 (1H, t, J=5.5 Hz), 8.42–8.60 (2H, br)

Mass (m/z): 342 (M$^+$+1) free of compound

EXAMPLE 15

A mixture of N-[(R)-1-{3-(1-tert-butoxycarbonyl-4-piperidyl)propionyl}-3-piperidylcarbonyl]-3(S)-vinyl-β-alanine ethyl ester (0.8 g) and PtO$_2$ (0.2 g) in ethanol (10 ml) was hydrogenated at atmospheric pressure for 2 hours. After the catalyst was removed by filtration, the filtrate was concentrated in vacuo to give N-[(R)-1-{3-(1-tert-butoxycarbonyl-4-piperidyl)propionyl}-3- piperidylcarbonyl]-3(S)-ethyl-β-alanine ethyl ester (0.73 g) as a colorless oil.

IR (Film): 3300, 1740, 1620 cm$^{-1}$

NMR (CDCl$_3$, δ): 0.92 (3H, t, J=7.5 Hz), 1.08–1.30 (6H, m), 1.45 (9H, s), 1.52–2.03 (11H, m), 2.33–2.74 (6H, m), 3.26–3.51 (2H, m), 3.72 (2H, q, J=7.5 Hz), 3.77–4.17 (5H, m), 6.64–6.69 (1H, br)

EXAMPLE 16

The solution of 4-(3-{3-(1-tert-butoxycarbonyl-4-piperidyl)propionylamino}-1-piperidyl]-4-oxo-2(S) benzyloxycarbonylaminobutyric acid tert-butyl ester (1.35 g) in tetrahydrofuran (10 ml) and methanol (10 ml) was added 10% Pd—C (0.27 g, 50% wet) was hydrogenated at atmospheric pressure for 6 hours. After the catalyst was removed by filtration, the filtrate was concentrated in vacuo to give 4-[3-{3-(1-tert-butoxycarbonyl-4-piperidyl) propionylamino}-1-piperidyl]-4-oxo-2(S)-aminobutyric acid tert-butyl ester (1.07 g) as an oil.

IR (Film): 2970, 2930, 2880, 1720, 1650 cm$^{-1}$

NMR (CDCl$_3$, δ): 0.97–1.20 (2H, m), 1.45 (18H, s), 1.33–1.84 (9H, m), 2.15–2.46 (2H, m), 2.53–2.76 (3H, m), 2.85–3.60 (5H, m), 3.70–4.40 (4H, m), 7.35 (1H, s)

Mass (m/z) 511 (M$^+$+1)

EXAMPLE 17

To a mixture of thioanisole (13.7 ml) and m-cresol (12.2 ml) in tetrahydrofuran (150 ml) was added N-[(R)-1-{2-(1-benzyloxycarbonyl-4-piperidyloxy)acetyl}-3-piperidylcarbonyl]-3-ethynyl-β-alanine ethyl ester (1.54 g). After stirring at ambient temperature for 2 hours, the mixture was poured into water and washed with diethyl ether. The extract was purified by HPLC on C18 silica gel eluting with (0.1% TFA aqueous solution:CH$_3$CN=4:1) to give N-[(R)-1-{2-(4-piperidyloxy)acetyl}-3-piperidylcarbonyl]-3-ethynyl-β-alanine ethyl ester trifluoroacetate as an oil (0.17 g).

NMR (DMSO-d$_6$, δ): 1.78 and 1.18 (total 3H, t, J=7.1 and 7.0 Hz), 1.29–2.71 (10H, m), 2.65 (1H, d, J=7.2 Hz), 2.90–3.2 (5H, m), 3.57–3.63 (3H, m), 4.01–4.39 (7H, m), 4.80–4.90 (1H, m), 8.45–8.56 (1H, m)

Mass (m/z): 394 (M$^+$+1) free of compound

EXAMPLE 18

A mixture of N-[(R)-1-{3-(1-tert-butoxycarbonyl-4-piperidyl)propionyl}-3-piperidylcarbonyl]-3(S)-(4-methoxyphenethylamino)carbonyl-β-alanine benzyl ester (0.9 g) and 10% Pd—C (0.2 g, 50% wet) in acetic acid (10 ml) was hydrogenated at atmospheric pressure for 3 hours. After the catalyst was removed by filtration, the filtrate was concentrated in vacuo. The residue was poured into water and extract with ethyl acetate. The extract washed with water, brine and dried over MgSO$_4$, and evaporated in vacuo. To give N-[(R)-1-{3-(1-tert-butoxycarbonyl)-4-piperidyl)propionyl}-3-piperidylcarbonyl]-3(S)-(4-methoxyphenethylamino)carbonyl-β-alanine as an oil (0.79 g).

IR (Film): 3390, 2930, 1710, 1645 cm$^{-1}$

NMR (DMSO-d$_6$, δ): 0.80–1.10 (3H, m), 1.30–1.84 (9H, m), 1.38 (9H, s), 1.91–1.99 (2H, m), 2.15–2.40 (3H, m), 2.58–2.69 (4Hi m), 2.88–3.26 (5H, m), 3.71 (3H, s), 3.76–4.53 (3H, m), 6.84 (2H, d, J=8.4 Hz), 7.11 (2H, d, J=8.3 Hz), 7.93–8.02 (1H, m), 8.09–8.18 (1H, m), 12.11–12.28 (1H, br)

Mass (m/z): 617 (M$^+$+1)

EXAMPLE 19

(1) Thionyl chloride (0.05 ml) was added to ethanol (1 ml) under stirring at −10° C. After stirring at −10° C. for 10 minutes, N-[(R)-1-{3-(4-piperidyl)propionyl}-3-piperidylcarbonyl]-3(R)-(3-methoxyphenethyl)-β-alanine hydrochloride (100 mg) was added. The mixture was stirred at ambient temperature for 2 hours, and evaporated in vacuo. The residue was dissolved in water and desalted by HP-20 eluting with (IPA:water =1:1) to give N-[(R)-1-{3-(4-piperidyl)propionyl}-3-piperidylcarbonyl]-3(R)-(3-methoxyphenethyl-β-alanine ethyl ester (80 mg).

NMR (DMSO-d$_6$, δ): 1.15 (3H, t, J=7.1 Hz), 1.19–1.93 (12H, m), 2.10–3.19 (14H, m), 3.72 (3H, S), 3.96–4.05 (5H, m), 4.12–4.39 (1H, m), 6.72–6.75 (3H, m), 7.14–7.22 (1H, m), 7.89 (1H, d, J=8.2 Hz)

Mass (m/z): 502 (M$^+$+1)

The following compound was obtained according to a similar manner to that of Example 19 (1).

(2) N-[(R)-1-{3-(4-piperidyl)propionyl}-3-piperidylcarbonyl]-3(S)-ethynyl-β-alanine methyl ester hydrochloride IR (Film): 3300, 2950, 1725, 1640, 1620 cm$^{-1}$ NMR (DMSO-d$_6$, δ): 1.20–1.87 (12H, m), 2.14–2.42 (3H, m), 2.60–3.29 (7H, m), 3.16 (3H, s), 3.59–3.84 (2H, m), 4.10–4.40 (1H, m), 4.77–4.92 (1H, m), 8.51 and 8.61 (total 1H, d, J=8.0 and 8.3 Hz), 8.74–8.90 (1H, br), 9.05–9.15 (1H, br)

Mass (m/z): 378 (M$^+$+1) free of compound

EXAMPLE 20

To a solution of N-[(R)-1-{3-(1-benzyloxycarbonyl-4-piperidyl)propionyl}-3-piperidylcarbonyl]-2(S)-amino-β-alanine ethyl ester hydrochloride (250 mg) in tetrahydrofuran (2 ml), ethanol (2 ml) was added a solution of lithium hydroxide (17 mg) in water (2 ml) under stirring at 0° C. After stirring at ambient temperature for 1 hour, the mixture was evaporated in vacuo. The residue was purified by HPLC on C18 silica gel eluting with a solution of 40% CH$_3$CN in 0.1% aqueous trifluoroacetic acid solution. The fractions containing object compound were combined and evaporated in vacuo, and freeze-dried to give N-[(R)-1-{3-(1-benzyloxycarbonyl-4-piperidyl)propionyl}-3-piperidylcarbonyl]-2(S)-amino-β-alanine alanine trifluoroacetate (230 mg).

IR (Nujol): 1770, 1730, 1650 cm$^{-1}$

NMR (DMSO-d$_6$, δ): 0.87–1.14 (2H, m), 1.24–1.56 (4H, m), 1.60–1.91 (4H, m), 2.09–2–17 (3H, m), 2.59–3.23 (5H, m), 3.32–3.84 (2H, m), 3.93–4.04 (4H, m), 4.13–4.43 (1H, m), 5.06 (2H, s), 4.88–5.28 (1H, br ), 7.27–7.40 (5H, m), 8.14–8.28 (3H, m)

Mass (m/z): 489 (M$^+$+1) free of compound

EXAMPLE 21

(1) A solution of N-[(R)-1-{3-(1-tert-butoxycarbonyl-4-piperidyl)propionyl}-3-piperidylcarbonyl]-3-ethynyl-β-alanine (1.12 g) in ethyl acetate (12 ml) was added 4N HCl in ethyl acetate (6.04 ml) under stirring at 0° C. After stirring at ambient temperature for 2 hours, and evaporated in vacuo. The residue was purified by HPLC on C18 silica gel column eluting with (0.1% trifluoroacetic acid aqueous solution (TFA):CH$_3$CN=89:11) to give one isomer of N-[(R)-1-{3-(4-piperidyl)propionynl]-3-piperidylcarbonyl]-3(S)-ethynyl-β-alanine trifluoroacetate [[α]$_D^{20}$−31.63° (C=1.0, MeOH): object compound (1)] (0.32 g) and the other isomer [[α]$_D^{20}$−1.47° (C=1.0, MeOH): object compound (2)] (0.35 g).

object compound (1)

IR (Film): 3270, 2930, 1720, 1630 cm$^{-1}$

NMR (DMSO-d$_6$, δ): 1.15–1.73 (8H, m), 1.81 (3H, d, J=13.6 Hz), 2.08–2.37 (3H, m), 2.59 (2H, d, J=8.8 Hz), 2.69–2.93 (3H, m), 2.97–3.28 (4H, m), 3.68–3.83 (2H, m), 4.10–4.34 (1H, m), 4.75–4.89 (1H, m), 8.14–8.30 (1H, br), 8.39–8.46 (1H, m), 8.50–8.61 (1H, br)

Mass (m/z): 364 (M$^+$+1) free of compound object compound (2)

IR (Film): 3230, 2930, 1725, 1620 cm$^{-1}$

NMR (DMSO-d$_6$, δ): 1.14–1.66 (8H, m), 1.81 (3H, d, J=13.8 Hz), 2.08–2.43 (3H, m), 2.58 (2H, d, J=7.6 Hz), 2.69–3.00 (5H, m), 3.10–3.29 (4H, m), 3.69–3.85 (1H, m), 4.04–4.16 and 4.31–4.42 (total 1H, m), 8.11–8.27 (1H, br), 8.40–8.45 (1H, m), 8.44–8.59 (1H, br)

Mass (m/z): 364 (M$^+$+1) free of compound

As a result of further study, we identified the object compound (1) with N-[(R)-1-{3-(4-piperidyl) propionyl}-3-piperidylcarbonyl]-3(S)-ethynyl-β-alanine trifluoroacetate and identified the object compound (2) with N-[(R)-1-{3-(4-piperidyl)propionyl}-3-piperidyl carboyl]-3(R)-ethynyl-β-alanine trifluoroacetate.

The following compounds were obtained according to a similar manner to that of Example 21 (1).

(2) (3R)-N-[(R)-1-{3-(4-Piperidyl)propionyl}-3-piperidylcarbonyl]-3-methyl-β-alanine hydrochloride mp: 105–108° C.

IR (Nujol): 1720, 1620, 1605 cm$^{-1}$

NMR (DMSO-d$_6$, δ): 1.04–1.09 (3H, m), 1.28–1.83 (12H, m), 2.06–2.49 (5H, m), 2.58–3.23 (6H, m), 3.70–3.83 (1H, m), 4.16–4.33 (1H, m), 7.94 (1H, dd, J=17 and 7.8 Hz), 8.71–8.98 (1H, m), 9.01–9.20 (1H, m)

Mass (m/z): 354 (M$^+$+1) free of compound

Elemental Analysis C$_{17}$H$_{29}$N$_3$O$_4$.HCl.1.25AcOEt.1.6H$_2$O(%) Calcd.: C, 51.32; H, 8.46; N, 8.16. Found: C, 51.22; H, 8.77; N, 7.92.

(3) N-[(R)-1-{3-(4-piperidyl)propionyl}-3-piperidylcarbonyl]-β-alanine hydrochloride

[α]$_D^{20}$-24.3° (C=1.0, MeOH)

mp: 84° C.

IR (Nujol): 3320, 1700, 1650 cm$^{-1}$

NMR (DMSO-d$_6$, δ): 1.21–1.65 (7H, m), 1.80 (3H, d, J=13.2 Hz), 2.29–2.41 (4H, m), 2.56–3.07 (4H, m), 3.15–3.26 (4H, m), 3.70–3.85 (1H, m), 4.13–4.37 (4H, m), 7.97–8.10 (1H, m), 8.60–8.76 (1H, br), 8.91–9.03 (1H, br)

Mass (m/z): 340 (M$^+$+1) free of compound

Elemental Analysis C$_{17}$H$_{29}$N$_3$O$_4$.HCl.1.5AcOEt.3H$_2$O (%) Calcd.: C, 49.15; H, 8.61; N, 7.48. Found: C, 49.08; H, 8.23; N, 7.29.

(4) N-[(R)-1-{3-(4-piperidyl)propionyl}-3-piperidylcarbonyl]-3(S)-(4-methoxyphenethyl-aminocarbonyl)-β-alanine hydrochloride

[α]$_D^{20}$=−19.07° C. (C=1.0, MeOH)

mp: 82° C.

IR (Nujol): 3280, 1725, 1630, 1600 cm$^{-1}$

NMR (DMSO-d$_6$, δ): 0.99–1.69 (10H, m), 2.11–2.82 (11H, m), 2.94–3.09 (4H, m), 3.49 (3H, s), 3.86–4.30 (4H, m), 6.63 (2H, d, J=8.4 Hz), 6.90 (2H, d, J=8.5 Hz), 7.81–8.19 (2H, m), 8.41–8.68 (1H, br), 8.71–8.85 (1H, br)

Mass (m/z): 515 (M$^+$-1) free of compound (5) N-[(R)-1-{3-(4-piperidyl)propionyl}-3-piperidylcarbonyl]-3(R)-phenethyl-β-alanine hydrochloride

[α]$_D^{25}$=−32.33° (C=1.0, MeOH)

IR (Nujol): 3300, 1700, 1620 cm$^{-1}$

NMR (DMSO-d$_6$, δ): 1.03–1.91.(13H, m), 2.06–3.07 (11H, m), 3.12–3.24 (2H, m), 3.70–3.90 (1H, m), 3.98–4.38 (2H, m), 7.16–7.51 (5H, m), 7.93–8.05 (1H, m), 8.71–9.01 (12H, m), 9.08–9.20 (1H, br)

Mass (m/z): 444 (M$^+$+1) free of compound

Elemental Analysis C$_{25}$H$_{37}$N$_3$O$_4$.HCl.2.7H$_2$O Calcd.: C, 56.80; H, 8.27; N, 7.95. Found: C, 56−94; H, 8.01; N, 7.58.

(6) N-[(R)-1-{3-(4-piperidyl)propionyl}-3-piperidylcarbonyl]-3(R)-(4-methoxyphenethyl)-β-alanine hydrochloride

[α]$_D^{20}$=43.1° (C=1.0, MeOH)

IR (Nujol): 1715, 1620, 1600 cm$^{-1}$

NMR (DMSO-d$_6$, δ): 1.22–1.86 (12H, m), 2.11–3.24 (12H, m), 3.71–4.36 (5H, m), 3.71 (3H, s), 6.82 (2H, d, J=8.6 Hz), 7.08 (2H, d, J=8.5 Hz), 7.90 (1H, t, J=8.8 Hz), 8.63–8.74 (1H, br), 8.90–9.01 (1H, br)

Mass (m/z): 474 (M++1) free of compound

Elemental Analysis C$_{26}$H$_{39}$N$_3$O$_5$.HCl.2H$_2$O Calcd.: C, 57.19; H, 8.12; N, 7.69. Found: C, 56.82; H, 8.17; N, 7.51.

(7) N-[(R)-1-{3-(4-piperidyl)propionyl}-3-piperidylcarbonyl]-2-(2-piperidyl)acetic acid hydrochloride IR (Nujol): 3350, 1705, 1600 cm$^{-1}$ NMR (DMSO-d$_6$, δ): 1.27–1.83 (16H, m), 2.23–2.40 (2H, m), 2.56–3.23 (6H, m), 3.70–4.55 (8H, m), 4.87–5.02 (1H, m), 8.65–8.84 (1H, br), 8.96–9.10 (1H, br)

Mass (m/z): 394 (M$^+$+1) free of compound (8) N-[4-{3-(4-piperidyl)propionyl}-2-morpholinylcarbonyl]-β-alanine hydrochloride IR (Nujol): 3300, 1705, 1625 cm$^{-1}$ NMR (DMSO-d$_6$, δ): 1.29–1.50 (5H, m), 1.77–1.83 (2H, m), 2.30–2.60 (4H, m), 2.70–2.94 (2+1/2H, m), 3.08–3.35 (5+1/2H, m), 3.40–3.57 (1H, m), 3.72–4.05 (3+1/2H, m), 4.43–4.49 (1/2H, m), 7.79–7.97 (1H, m), 8.73–8.89 (1H, br), 9.04–9.16 (1H, br)

Mass (m/z): 342 (M$^+$+1) free of compound (9) N-[(R)-1-{3-(4-piperidyl)propionyl}-3-piperidylcarbonyl]-3-phenyl-β-alanine hydrochloride mp: 67° C.

IR (Nujol): 1710, 1630, 1600 cm$^{-1}$

NMR (DMSO-d$_6$, δ): 1.24–1.91 (10H, m), 2.10–2.41 (3H, m), 2.59–3.09 (5H, m), 3.14–3.25 (2H, m), 3.63–3.86 (1H, m), 4.08–4.41 (1H, m), 5.18 (1H, q, J=7.8 Hz), 7.20–7.27 (1H, m), 7.31 (5H, s), 8.49–8.66 (1H, br), 8.80–8.94 (1H, br), 9.06–9.20 (1H, br)

Mass (m/z): 416 (M++1) free of compound

(10) N-[(R)-1-{3-(4-piperidyl)propionyl}-3-piperidylcarbonyl]-3(R)-(3,4-dimethoxyphenethyl)-β-alanine hydrochloride

[α]$_D^{20}$=−13.33° (C=1.0, MeOH)

IR (Nujol): 1730, 1635 cm$^{-1}$

NMR (DMSO-d$_6$, δ): 1.01–1.50 (9H, m), 1.66–1.83 (8H, m), 1.83–3.23 (11H, m), 3.71 (3H, s), 3.73 (3H, s), 4.15–4.38 (2H, m), 6.65–6.69 (1H, m), 6.77–6.85 (2H, m), 8.88–9.02 (1H, br), 9.15–9.25 (1H, br)

Mass (m/z): 504 (M$^+$+1) free of compound

(11) N-[(R)-1-{3-(4-piperidyl)propionyl]-3-piperidylcarbonyl}-3(S)-(3-methoxyphenethyl)-β-alanine hydrochloride IR (Nujol): 1710, 1600, 720 cm$^{-1}$ NMR (DMSO-d$_6$, δ): 1.13–2.00 (14H, m), 2.01–3.70 (9H, m), 3.17–3.29 (2H, m), 3.73 (3H, s), 3.97– 4.08 (1H, m), 4.10–4.37 (1H, m), 6.74 (3H, d like), 7.18 (1H, t like), 7.92 (1H, t like), 8.72 (1H, br), 8.99 (1H, br)

Mass (m/z): 474 (M$^+$+1) free of compound

(12) N-[(R)-1-{3-(4-piperidyl)propionyl}-3-piperidylcarbonyl]-2(S)-benzoylamino-β-alanine hydrochloride IR (Nujol): 3100, 1725, 1630 cm$^{-1}$ NMR (DMSO-d$_6$, δ): 1.2–1.85 (12H, m), 2.27–2.36 (2H, m), 2.57–3.10 (4H, m), 3.12–3.25 (2H, m), 3.39–3.82 (3H, m), 4.07–4.59 (3H, m), 7.45–7.56 (3h, m), 7.87–7.91 (22H, m), 8.22–8.40 (1H, m), 8.65–8.75 (1H, m), 8.89–9.02 (1H, m)

Mass (m/z): 459 (M$^+$+1) free of compound

(13) N-[(R)-1-{3-(4-piperidyl)propionyl}-3-piperidylcarbonyl]-3(R)-(3-trifluoromethylphenethyl)-β-alanine alanine hydrochloride mp: 118° C.

[α]$_D^{20}$=−21.4° (C−1.0, MeOH)

IR (Nujol): 3300, 1715, 1630, 1610 cm$^{-1}$

NMR (DMSO-d$_6$, δ): 1.23–2.13 (14H, m), 2.35–2.45 (5H, m), 2.61–2.83 (5H, m), 3.15–3.28 (2H, m), 3.72–3.89 (1H, m), 3.99–4.10 (1H, m), 4.15–4.41 (1H, m), 7.49–7.55 (4H, m), 7.94–8.05 (1H, m), 8.75–8.93 (1H, m), 9.03–9.17 (1H, m)

Mass (m/z): 512 (M$^+$+1) free of compound

Elemental Analysis $C_{26}H_{36}F_3N_3O_4 \cdot HCl \cdot 1.8H_2O$ Calcd.: C, 53.80; H, 7.05; N, 7.24. Found: C, 53.72; H, 7.10; N, 7.02.

(14) N-[(R)-1-{3-(4-piperidyl)propionyl}-3-piperidylcarbonyl]-2(S)-phenylsulfonylamino-β-alanine hydrochloride

[α]$_D^{25}$=−14.23° (C=1.0, MeOH)

IR (Nujol): 1720, 1630 cm$^{-1}$

NMR (DMSO-d$_6$, δ): 1.21–1-83 (11H, m), 2.04–2.37 (3H, m), 2.70–3.40 (7H, m), 3.74–3.91 (2H, m), 4.12–4.39 (2H, m), 7.55–7.62 (3H, m), 7.75–7.79 (2H, m), 8.01–8.26 (2H, m), 8.50–8.66 (1H, br), 8.82–8.94 (1H, br)

Mass (m/z): 495 (M$^+$+1) free of compound

(15) N-[(R)-1-{3-(4-piperidyl)propionyl}-3-piperidylcarbonyl]-3(R)-(2-methoxyphenethyl)-β-alanine hydrochloride

[α]$_D^{20}$=−17.73° (C=1.0, MeOH)

IR (Nujol): 1725, 1640, 1600 cm$^{-1}$

NMR (DMSO-d$_6$, δ): 1.21–1.91 (16H, m), 2.30–3.24 (11H, m), 3.75 (3H, s), 3.70–3.89 (1H, m), 4.12–4.39 (1H, m), 6.81–6.94 (2H, m), 7.07–7.20 (2H, m), 7.84–7.94 (1H, m), 8.60–8.75 (1H, br), 8.91–9.03 (1H, br)

Mass (m/z): 474 (M$^+$+1) free of compound

(16) N-[(R)-1-{3-(4-piperidyl)propionyl}-3-piperidylcarbonyl3−2(S)-(n-butanesulfonylamino)-β-alanine hydrochloride

[α]$_D^{25}$=−31.37° (C=1.0, MeOH)

IR (Nujol): 1715, 1620 cm$^{-1}$

NMR (DMSO-d$_6$, δ): 0.88 (3H, t, J=7.2 Hz), 1.14–1.89 (15H, m), 2.29–2.40 (2H, m), 2.77–3.06 (6H, m), 3.19–3.27 (2H, m), 3.77–4.41 (5H, m), 7.51–7.60 (1H, m), 8.04–8.18 (1H, m), 8.43–8.18 (1H, m), 8.43–8.60 (1H, br), 8.73–8.86 (1H, br)

Mass (m/z): 475 (M$^+$+1) free of compound

(17) N-[(R)-1-{3-(3-piperidyl)propionyl}-3-piperidylcarbonyl]-3(R)-(3,4-methylenedioxy-phenethyl)-β-alanine hydrochloride

[α]$_D^{25}$: −17.27° (C=1.0, MeOH)

IR (Nujol): 1725, 1685, 1620 cm$^{-1}$

NMR (DMSO-d$_6$, δ): 0.84–1.50 (6H, m), 1.59–1.91 (6H, m), 1.06–3.28 (12H, m), 3.60–4.27 (5H, m), 4.30–4.40 (1H, m), 5.95 (2H, s), 6.59–6.63 (1H, m), 6.75–6.81 (2H, m), 7.84–7.90 (1H, m)

Mass (m/z): 488 (M$^+$+1) free of compound

Elemental Analysis $C_{26}H_{37}N_3O_6 \cdot HCl \cdot 1/4EtOAc \cdot 1.4H_2O$ Calcd.: C, 56.77; H, 7.55; N, 7.36. Found: C, 56.81; H, 7.69; N, 7.11.

(18) N-[(R)-1-{3-(4-piperidyl)propionyl}-3-piperidylcarbonyl]-3(S)-ethynyl-β-alanine hydrochloride IR (KBr): 3425, 3250, 1726, 1638, 1614 cm$^{-1}$ NMR (DMSO-d$_6$, δ): 1.27–1.83 (11H, m), 2.08–2.32 (3H, m), 2.58–3.09 (5H, m), 3.18–3.22 (3H, m), 3.75–3.80 (1H, m), 4.08–4.32 (1H, m), 4.79–4.82 (1H, m), 8.42–8.54 (1H, m), 8.75 (1H, br), 9.04 (1H, br)

Mass (m/z): 364 (M$^+$+1) free of compound

(19) N-[1-{3-(4-piperidyl)propionyl}-3-piperidyl] succinamic acid hydrochloride

IR (Nujol): 3200, 1710, 1620 cm$^{-1}$

NMR (DMSO-d$_6$, δ): 1.25–1.52 (7H, m), 1.69–1.86 (4H, m), 2.21–2.46 (6H, m), 2.69–3.06 (4H, m), 3.15–3.26 (2H, m), 3.47–3.84 (2H, m), 4.14–4.24 (1H, m), 7.80–7.97 (1H, m), 8.64–8.78 (1H, br) 8.95–9.06 (1H, br)

Mass (m/z): 340 (M$^+$+1) free of compound

(20) N-[(R)-1-{3-(4-piperidyl)propionyl}-3-piperidylcarbonyl]-3(S)-propargylaminocarbonyl-β-alanine hydrochloride

[α]$_D^{25}$=−11.9° (C=1.0, MeOH)

IR (Nujol): 1735, 1640 cm$^{-1}$

NMR (DMSO-d$_6$, δ): 1.21–1.69 (7H, m), 1.75–1.86 (3H, m), 2.06–2.40 (3H, m), 2.56–3.04 (5H, m), 3.17–3.26 (4H, m), 3.68–3.87 (3H, m), 4.08–4.56 (3H, m), 8.11–8.30 (1H, m), 8.34–8.50 (1H, m), 8.60–8.73 (1H, br), 8.90–9.02 (1H, m)

Mass (m/z): 421 (M$^+$+1) free of compound

(21) 4-[3-(3-(4-piperidyl)propionylamino}-1-piperidyl]-4-oxo-butyric acid hydrochloride IR (Nujol): 1735, 1700, 1610 cm$^{-1}$ NMR (DMSO-d$_6$, δ): 1.25–1.50 (9H, m), 1.71–1.83 (4H, m), 2.06–2.16 (2H, m), 2.39–2.46 (3H, m), 2.70–2.87 (2H, m), 2.96–3.08 (1H, m), 3.15–3.25 (2H, m), 3.52–3.76 (2H, m), 4.08–4.16 (1H, m), 7.84, 7.95 (total 1H, d, J=7.8 and 6.5 Hz), 8.73–8.88 (1H, br), 9.00–9.10 (1H, br)

Mass (m/z): 340 (M$^+$+1) free of compound

(22) N-[(S)-1-{3-(4-piperidyl)propionyl}-3-piperidylcarbonyl]-3(R)-ethynyl-β-alanine trifluoroacetate

[α]$_D^{20}$=35.7° (C=0.65, MeOH)

IR (Film) 3250, 2930, 2850, 1760, 1700, 1610 cm$^{-1}$

NMR (DMSO-d$_6$, δ): 1.14–1.84 (1H, m), 2.09–2.40 (3H, m), 2.57–3.28 (9H, m), 3.69–3.83 (1H, m), 4.08–4.33 (1H, m), 4.75–4.86 (1H, m), 4.14–8.29 (1H, br), 8.38–8.47 (1H, m), 8.49–8.60 (1H, br)

Mass (m/z): 364 (M$^+$+1) free of compound and N-[(S)-1-{3-(4-piperidyl)propionyl}-3-piperidylcarbonyl]-3(S)-ethynyl-β-alanine trifluoro acetate IR (Film): 3250, 2930, 2850, 1740, 1700, 1610 cm$^{-1}$ NMR (DMSO-d$_6$, δ): 1.15–1.85 (11H, m), 2.05–2.40 (3H, m), 2.56–3.00 (6H, m), 3.11–3.28 (3H, m), 3.70–3.88 (1H, m), 4.05–4.15 and 4.30–4.44 (total 1H, m), 4.75–4.90 (1H, m), 8.15–8.30 (1H, br), 8.40–8.49 (1H, m), 8.49–8−60 (1H, br)

Mass (m/z): 364 (M$^+$+1) free of compound

EXAMPLE 22

A mixture of N-[1-{2-(1-benzyloxycarbonyl-4-piperidyloxy)acetyl}-3-piperidylcarbonyl]-β-alanine (1.16 g) and 10% Pd—C (0.23 g, 50% wet) in a solution of 1N HCl (2.44 ml) and tetrahydrofuran (20 ml) was hydrogenated at atmospheric pressure for 2 hours. After the catalyst was removed by filtration, the filtrate was concentrated in vacuo and freeze-dried to give N-[1-{2-(4-piperidyloxy)acetyl}-3-piperidylcarbonyl]-β-alanine hydrochloride (0.69 g).

IR (Nujol): 3290, 1700, 1625 cm$^{-1}$

NMR (DMSO-d$_6$, δ): 1.15–2.09 (9H, m), 2.11–2.69 (2H, m), 2.84–3.25 (8H, m), 3.56–3.74 (2H, m), 4.07–4.32 (3H, m), 8.06–8.24 (1H, m)

Mass (m/z): 342 (M$^+$+1) free of compound
Elemental Analysis C$_{16}$H$_{27}$N$_3$O$_5$.HCl.1.8H$_2$O (%) Calcd.: C, 46.84; H, 7.76; N, 10.24. Found: C, 47.09; H, 7.46; N, 9.91.

EXAMPLE 23

(1) A mixture of N-[(R)-1-{3-(1-benzyloxycarbonyl-4-piperidyl)propionyl}-3-piperidylcarbonyl]-2(S)-acetylamino-β-alanine (67 mg) and 10% Pd—C (15 mg, 50% wet) in a mixture of 1N HCl (0.13 ml) and tetrahydrofuran (2 ml) was hydrogenated at atmospheric pressure for 1 hour. After the catalyst was removed by filtration, the filtrate was concentrated in vacuo. The residue was dissolved in water (5 ml) and then freeze-dried to give N-[(R)-1-{3-(4-piperidyl)propionyl-3-piperidylcarbonyl]-2(S)-acetylamino-β-alanine hydrochloride (50 mg).
$[α]_D^{25}$=−21.37° (C=0.75, MeOH)
IR (Nujol): 1720, 1640, 1610 cm$^{-1}$
NMR (DMSO-d$_6$, δ): 1.20–1–82 (12H, m), 1.85 (3H, s), 2.10–2.43 (5H, m), 2.59–3.27 (4H, m), 3.74–3.83 (2H, m), 4.14–4.37 (2H, m), 8.02–8.19 (2H, m), 8.42–8.59 (1H, br), 8.72–8.84 (1H, br)
Mass (m/z): 397 (M$^+$+1) free of compound The following compounds were obtained according to a similar manner to that of Example 23 (1).

(2) N-[2-[1-{3-(4-piperidyl)propionyl}-3-piperidyl]acetyl] glycine hydrochloride
IR (Film): 3350, 2940, 1715, 1630 cm$^{-1}$
NMR (DMSO-d$_6$, δ): 1.11–1.82 (12H, m), 2.00–2.11 (2H, m), 2.24–2.40 (2H, m), 2.62–3.03 (4H, m), 3.20 (2H, d, J=12.6 Hz), 3.64–3.82 (3H, m), 4.07–4.24 (1H, m), 8.25–8.35 (1H, m), 8.75–8.91 (1H, br), 9.09–9.20 (1H, br)
Mass (m/z): 340 (M$^+$=1) free of compound (3) N-[1-{3-(4-piperidyl)propionyl}-3-piperidylcarbonyl]-3-methyl-β-alanine hydrochloride
IR (Nujol): 3250, 1705, 1610 cm$^{-1}$
NMR (DMSO-d$_6$, δ): 1.04–1.09 (3H, m), 1.28–1.83 (11H, m), 2.10–3.44 (9H, m), 3.71–3.83 (1H, m), 3.98–4.34 (2H, m), 7.86–7.96 (1H, m), 8.74–8.87 (1H, m), 9.01–9.15 (1H, m)
Mass (m/z): 354 (M$^+$+1) free of compound (4) N-[(R)-1-{2-(4-piperidyloxy)acetyly-3-piperidylcarbonyl]-β-alanine ethyl ester hydrochloride
IR (Film): 2930, 1720, 1625 cm$^{-1}$
NMR (DMSO-d$_6$, δ): 1.18 (3H, t, J=7.1 Hz), 1.46–2.47 (11H, m), 2.60–2.70 (1H, m), 2.86–3.27 (8H, m), 3.55–3.72 (2H, m), 4.05 (2H, q, J=7.1 Hz), 4.17–4.30 (2H, m), 8.06–8.21 (1H, m), 9.00–9.14 (2H, 5 br)
Mass (m/z): 370 (M$^+$+1) free of compound (5) N-[1-{3-(4-piperidyl)propionyl}-1,2,3,4-tetrahydro-3-quinolylcarbonyl]-β-alanine hydrochloride
IR (Film): 3450, 3930, 1720, 1630 cm$^{-1}$
NMR (DMSO-d$_6$, δ): 1.12–1.89 (9H, m), 2.10–2.21 (2H, m), 2.39 (2H, d, J=6.7 Hz), 2.70–3,84 (7H, m), 4.26 (2H, t, J=7.0 Hz), 7.06–7.20 (4H, m), 8.13–8.24 (1H, m)
Mass (m/z): 386 (M$^+$−1) free of compound (6) N-[(S)-1-{2-(4-piperidyloxy)acetyl}-3-piperidylcarbonyl]-β-alanine hydrochloride
IR (Film): 3290, 2920, 1710, 1620 cm$^{-1}$
NMR (DMSO-d$_6$, δ): 1.24–2.07 (9H, m), 2.11–2.69 (2H, m), 2.89–3.27 (8H, m), 3.57–3.74 (2H, m), 4.07–4.30 (3H, m), 8.03–8.87 (1H, m)
Mass (m/z): 342 (M$^+$+1) free of compound (7) N-((R)-1-{3-(4-piperidyl)propionyl}-3-piperidylcarbonyl]-2(S)-(n-hexanoylamino)-β-alanine hydrochloride
$[α]_D^{20}$=−27.7° (C=1.0, MeOH)
mp: 156–157° C.
IR (Nujol): 3200, 1720, 1660, 1600 cm$^{-1}$
NMR (DMSO-d$_6$, δ): 0.85 (3H, t, J=6.5 Hz), 1.55–1.88 (17H, m), 2.10 (2H, t, J=7.4 Hz), 2.27–3.82 (12H, m), 4.14–4.35 (2H, m), 7.97–8.10 (2H, m), 8.37–8.51 (1H, br), 8.69–8.89 (1H, br)
Mass (m/z): 453 (M$^+$+1) free of compound (8) N-[(R)-1-{3-(4-piperidyl)propionyl}-3-piperidylcarbonyl]-2(S)-(4-chlorobenzoylamino)-β-alanine hydrochloride
$[α]_D^{20}$=−35.6° (C=1.0, MeOH)
IR (Nujol): 3200, 1730, 1710, 1640 cm$^{-1}$
NMR (DMSO-d$_6$, δ): 1.16–1.85 (11H, m), 2.11–2.34 (3H, m), 2.60–3.25 (6H, m), 3.34–3.82 (3H, m), 4.18–4.35 (1H, m), 4.44–4.54 (1H, m), 7.44–7.59 (2H, m), 7.84–7.92 (2H, m), 8.18–8.31 (1H, m), 8.41–8.55 (1H, m), 8.60–8.83 (2H, m)
Mass (m/z): 493 (M$^+$+1) free of compound (9) N-[(R)-1-{3-(4-piperidyl)propionyl}-3-piperidylcarbonyl]-2(S)-(4-methoxybenzoylamino)-β-alanine hydrochloride
α]$_D^{20}$=−31.8° (C=1.0, MeOH)
IR (Nujol): 3210, 1720, 1620, 1600 cm$^{-1}$
NMR (DMSO-d$_6$, δ): 1.11–1.89 (12H, m), 2.12–2.39 (3H, m), 2.60–3.79 (8H, m), 3.82 (3H, s), 4.10–4.35 (1H, m), 4.44–4.54 (1H, m), 7.02 (2H, d, J=8.8 Hz), 7.55 (2H, d, J=8.1 Hz), 8.13–8.31 (1H, m), 8.44–8.55 (2H, m), 8.70–8.84 (1H, m)
Mass (m/z): 489 (M$^+$+1) free of compound

(10) N-[(R)-1-{3-(4-piperidyl)propionyl}-3-piperidylcarbonyl]-2(S)-amino-β-alanine hydrochloride
IR (Film): 3250, 2910, 1745, 1640 cm$^{-1}$
NMR (DMSO-d$_6$, δ): 1.19–1.91 (12H, m), 2.07–2.43 (4H, m), 2.58–3.24 (2H, m), 3.50–3.57 (2H, m), 3.74–4.40 (3H, m), 8.30–8.96 (5H, m)
Mass (m/z): 355 (M$^+$+1) free of compound

(11) N-[(R)-1-{3-(4-piperidyl)propionyl}-3-piperidylcarbonyl]-2(S)-benzoylamino-β-alanine 1-(cyclohexyloxycarbonyloxy)ethyl ester hydrochloride
IR (Nujol): 3240, 1750, 1640 cm$^{-1}$
NMR (DMSO-d$_6$, δ): 1.01–1.91 (23H, m), 1.76 (3H, d, J=5.7 Hz), 2.11–2.39 (3H, m), 2.58–3.25 (2H, m), 3.35–4.40 (7H, m), 4.49–4.66 (2H, m), 6.63 (1H, t, J=5.1 Hz), 7.43–7.57 (5H, m), 7.85–7.95 (1H, m)
Mass (m/z): 629 (M$^+$+1) free of compound

(12) N-{1-{3-(4-piperidyl)propionyl}-3-piperidyl]-2(S)-benzoylaminosuccinamic acid hydrochloride
IR (Nujol): 3300, 1720, 1630 cm$^{-1}$
NMR (DMSO-d$_6$, δ): 1.16–1.54 (6H, m), 1.64–1.85 (6H, m), 2.24–2.34 (1H, m), 2.63–3.03 (5H, m), 3.13–3.84 (7H, m), 4.70–4.83 (1H, m), 7.41–7.53 (3H, m), 7.83–7.90 (2H, m), 8.60–8.72 (1H, m)
Mass (m/z): 459 (M$^+$+1) free of compound

(13) N-[(R)-1-{3-(4-piperidyl)propionyl}-3-piperidylcarbonyl]-2(S)-cyclopropylcarbonylamino-β-alanine hydrochloride
$[α]_D^{20}$=−20.2° (C=1.0, MeOH)
IR (Nujol): 1715, 1645, 1610 cm$^{-1}$
NMR (DMSO-d$_6$, δ): 0.67 (4H, d, J=6.3 Hz), 1.18–1.84 (12H, m), 2.10–2.43 (3H, m), 2.60–3.34 (7H, m), 3.74–3.83 (2H, m), 4.15–4.35 (2H, m), 8.04–8.22 (1H, m), 8.39 (1H, dd, J=19.6 and 7.9 Hzy, 8.51–8.69 (1H, br), 8.82–8.86 (1H, br)
Mass (m/z): 423 (M$^+$+1) free of compound

(14) N-[(R)-7-{3-(4-piperidyl)propionyl)-3-piperidylcarbonyl]-2(S)-(3-methoxypropionyl)amino-β-alanine hydrochloride $[\alpha]_D^{20} = -20.20°$ (C=1.0, MeOH)

IR (Nujol): 3250, 1720, 1650, 1610 cm$^{-1}$

NMR (DMSO-d$_6$, δ): 1.12–1.89 (15H, m), 2.11–2.43 (3H, m), 2.37 (2H, t, J=6.5 Hz), 2.72–3.12 (3H, m), 3.21 (3H, s), 3.25–3.44 (2H, m), 3.52–2H, t, J=6.5 Hz), 3.61–3.84 (2H, m), 4.14–4.39 (2H, m), 7.94–8.09 (2H, m)

Mass (m/z): 441 (M$^+$+1) free of compound

(15) N-[(R)-1-{3-(4-piperidyl)propionyl}-3-piperidylcarbonyl]-2(R)-benzoylamino-β-alanine hydrochloride $[\alpha]_D^{20} = -14.3°$ (C=1.0, MeOH)

IR (Nujol): 1750, 1730, 1640 cm$^{-1}$

NMR (DMSO-d$_6$, δ): 1.15–1.86 (12H, m), 2.25–3.05 (6H, m), 3.10–3.26 (2H, m), 3.37–3.84 (3H, m), 4.12–4.61 (2H, m), 7.45–7.63 (3H, m), 7.88–7.97 (2H, m), 8.28–8.45 (1H, m), 8.72–8.77 (1H, m), 8.66–8.84 (1H, br), 8.97–9.11 (1H, br)

Mass (m/z): 459 (M$^+$+1) free of compound

(16) N-[(R)-1-{3-(4-piperidyl)propynl}-3-piperidylcarbonyl]-2(S)-(4-hydroxybenzoylamino)-β-alanine hydrochloride $[\alpha]_D^{20} = -40.5$ (C=1.0, MeOH)

IR (Nujol): 1715, 1630, 1640, 1600 cm$^{-1}$

NMR (DMSO-d$_6$, δ): 1.17–1.85 (12H, m), 2.11–2.38 (3H, m), 2.60–3.06 (3H, m), 3.11–3.23 (2H, m), 3.36–3.84 (4h, m), 4.01–4.51 (2H, m), 6.83 (2h, d, J=8.5 Hz), 7.76 (2H, d, J=8.6 Hz), 8.20–8.46 (2H, m), 8.56–8.71 (1H, br), 8.85–8.98 (1H, br)

Mass (m/z): 473 (M$^+$−1) free of compound

(17) N-[1-{3-(4-piperidyl)propionyl}-3-piperidyl]-3(S)-benzoylaminosuccinamic acid hydrochloride IR (KBr, pellet): 2949, 2393, 1734, 1718, 1651 cm$^{-1}$ NMR (DMSO-d$_6$, δ): 1.16–1.89 (11H, m), 2.11–2.38 (1H, m), 2.61–3.07 (4H, m), 3.13–3.85 (8H, m), 4.66–4.86 (1H, m), 7.44–7.59 (3H, m), 7.85–7.88 (2H, m), 7.93–8.11 (1H, m), 8.44–8.60 (1H, br), 8.63–8.74 (1H, m), 8.77–8.90 (1H, br)

Mass (m/z): 457 (M$^+$−1) free of compound

(18) N-[1-{3-(4-piperidyl)propionyl}-3-piperidyl]-2(S)-acetylaminosuccinamic acid hydrochloride IR (KBr, pellet): 3057, 2945, 2864, 1734, 1653, 1618 cm$^{-1}$ NMR (DMSO-d$_6$, δ): 1.20–1.59 (7H, m), 1.73–1.97 (4H, m), 1.83 (3H, s), 2.24–2.36 (2H, m), 2.44=3.10 (4H, m), 3.17–3.28 (3H, m), 3.47–4.21 (4H, m), 4.43–4.59 (1h, m), 7.81–8.21 (2H, m), 8.56–8.76 (1H, br), 8.89–9.03 (1H, br)

Mass (m/z): 397 (M$^+$+1) free of compound

(19) N-[(R)-1-{3-(4-piperidyl)propionyl}-3-piperidylcarbonyl]-2(R)-acetylamino-β-alanine hydrochloride $[\alpha]_D^{20} = -21.7°$ (C=1.0, MeOH)

IR (KBr, pellet): 2947, 2864, 1734, 1653, 1616 cm$^{-1}$

NMR (DMSO-d$_6$, δ): 1.17–1.90 (12H, m), 1.85 (3H, s), 2.09–2.65 (4H, m), 2.70–3.08 (2H, m), 3.15–3.34 (3H, m), 3.60–3.88 (2H, m), 4.17–4.40 (2H, m), 8.00–8.20 (2H, m), 8.30–8.46(1H, br), 8.61–8.74 (1H, br)

Mass (m/z): 397 (M$^+$+1) free of compound

(20) N-[1-{3-(4-piperidyl)propionyl}-3-piperidyl]-3(R)-benzoylaminosuccinamic acid hydrochloride IR (KBr, pellet): 2947, 2864, 1734, 1647, 1605 cm$^{-1}$ NMR (DMSO-d$_6$, δ): 1.15–1.55 (7H, m), 1.64–1.89 (5H, m), 2.18–2.35 (1H, m), 2.60–3.26 (8H, m), 3.48–3.86 (4H, m), 4.69–4.84 (1H, m), 7.45–7.56 (3H, m), 7.85–7.88 (2H, m), 8.42–8.60 (1H, br), 8.75– 8.89 (1H, br), 8.61–8.75 (1H, m) Mass (m/z): 459 (M$^+$+1) free of compound

(21) N-[(R)-1-{3-(4-piperidyl)propionyl}-3-piperidylcarbonyl]-2(S)-(4-biphenylcarbonylamino)-β-alanine hydrochloride IR (KBr, pellet): 2947, 2729, 1734, 1647, 1608 cm$^{-1}$ NMR (DMSO-d$_6$, δ): 1.14–1.86 (10H, m), 2.20–2.36 (2H, m), 2.63–3.26 (5H, m), 3.40–3.86 (4H, m), 4.10–4.60 (4H, m), 7.41–7.54 (3H, m), 7.74–7.82 (4H, m), 7.98–8.01 (2H, m), 8.25–8.43 (1H, m), 8.57–8.80 (1H, br), 8.68–8.82 (1H, m), 8.92–9.02 (1H, br)

Mass (m/z): 535 (M$^+$+1) free of compound

EXAMPLE 24

(1) A solution of N-[1-{3-(1-tert-butoxycarbonyl-4-piperidyl)propionyl}-3-piperidylcarbonyl]-β-alanine (1.58 g) in ethyl acetate (16 ml) was added 4N HCl in ethyl acetate (13.5 ml) under stirring at 0° C. After stirring at ambient temperature for 2 hours, resulting precipitate was collected by filtration to give N-[1-{3-(4-piperidyl)-propionyl}-3-piperidylcarbonyl]-β-alanine hydrochloride (1.27 g).

mp: 70–72° C.

IR (KBr): 3200, 2850, 1780, 1600 cm$^{-1}$

NMR (DMSO-d$_6$, δ): 1.29–1.83 (10H, m), 2.09–2.42 (6H, m), 2.60–3.24 (7H, m), 3.70–3.84 (1H, m), 4.13–4.40 (1H, m), 7.97–8.18 (1H, m), 8.76–8.86 (1H, m), 9.09–9.23 (1H, m)

Mass (m/z): 340 (M$^+$+1) free of compound

The following compounds were obtained according to a similar manner to that of Example 24 (1).

(2) N-[1-{3-(4-Piperidyl)propionyl}-4-piperidylcarbonyl]-β-alanine hydrochloride mp: 63–65° C.

IR (KBr): 3250, 2800, 1710 cm$^{-1}$

NMR (DMSO-d$_6$, δ): 1.28–1.90 (11H, m), 2.23–2.40 (5H, m), 2.48–3.12 (4H, m), 3.10–3.30 (4H, m), 3.79–3.98 (1H, m), 4.30–4.40 (1H, m), 4.30–4.40 (1H, m), 7.98 (1H, t, J=5.4 Hz), 8.85–8.98 (1H, br), 9.13–9.21 (1H, br)

Mass (m/z): 340 (M$^+$+1) free of compound (3) N-[2-[1-{2-(4-Piperidyl)acetyl}-3-piperidyl]acetyl]β-alanine hydrochloride mp: 73° C.

IR (Nujol): 3200, 1725, 1605 cm$^{-1}$

NMR (DMSO-d$_6$, δ): 1.22–1.51 (4H, m), 1.68–1.87 (3H, m), 1.92–2.09 (4H, m), 2.23–2.30 (2H, m), 2.35–2.45 (3H, m), 2.60–3.02 (4H, m), 3.16–3.31 (5H, m), 3.67–3.81 (1H, m), 4.11–4.28 (1H, m), 8.00–8.16 (1H, m)

Mass (m/z): 340 (M$^+$+1) free of compound

Elemental Analysis $C_{17}H_{29}N_3O_4 \cdot HCl \cdot 1.5AcOEt \cdot 2H_2O$ (%) Calcd.: C, 50.78; H, 8.52; N, 7.72. Found: C, 50.76; H, 8.48; N, 7.70.

(4) N-[1-{4-(4-Piperidyl)butyryl}-3-piperidylcarbonyl]-glycine hydrochloride

IR (Nujol): 1740 cm$^{-1}$

NMR (DMSO-d$_6$, δ): 1.20–1.94 (13H, m), 2.30–2.40 (3H, m), 2.60–3.14 (5H, m), 3.17–3.28 (2H, m), 3.72–4.00 (2H, m), 4.00–4.10 and 4.09–4.17 (total 1H, m), 8.28–8.43 (1H, m)

Mass (m/z): 340 (M$^+$+1) free of compound

Elemental Analysis $C_{17}H_{29}N_3O_4 \cdot HCl \cdot 1.25AcOEt \cdot 1.5H_2O$ (%) Calcd.: C, 51.51; H, 8.45; N, 8.19. Found: C, 51.38; H, 8.43; N, 8.00.

(5) N-[2-[1-{2-(4-Piperidylidene)acetyl}-3-piperidyl]acetyl]-β-alanine hydrochloride mp: 63° C.

IR (Nujol): 3200, 1730 cm$^{-1}$

NMR (DMSO-d$_6$, δ): 1.08–1.41 (3H, m), 1.60–1.76 (3H, m), 1.76–1.92 (3H, m), 1.92–2.04 (2H, m), 2.39 (2H, t, J=6.5 Hz), 2.44–2.51 (3H, m), 2.60–2.83 (3H, m), 2.93–3.50 (4H, m), 3.69–3.84 (1H, m), 4.04–4.28 (1H, m), 6.04 and 6.08 (total 1H, s), 8.01–8.17 (1H, m)

Mass (m/z): 338 (M⁺+1) free of compound
Elemental Analysis $C_{17}H_{27}N_3O_4 \cdot HCl \cdot 1.5AcOEt \cdot 2.5H_2O$ (%) Calcd.: C, 50.50; H, 7.55; N 7.68. Found: C, 50.29; H, 7.91; N, 7.66.

(6) N-[(R)-1-{3-(4-piperidyl)propionyl}-3-piperidylcarbonyl]-3(S)-phenylsulfonylmethyl-β-alanine hydrochloride IR (Nujol): 1730, 1650, 1610 cm⁻¹

NMR (DMSO-$d_6$, δ): 1.28–1.83 (13H, m), 2.25–2.34 (2H, m), 2.48–3.23 (9H, m), 3.54–3.67 (2H, m), 4.18–4.26 (1H, m), 7.61–7.76 (3H, m), 7.85–7.99 (2H, m), 8.02–8.13 (1H, m), 8.76 (1H, hr), 9.03 (1H, br)

Mass (m/z): 492 (M⁺+1) free of compound

EXAMPLE 25

(1) A solution of N-[(R)-1-{3-(1-tert-butoxycarbonyl-4-piperidyl)pyropionyl}-3-piperidylcarbonyl]-β-alanine ethyl ester (0.78 g) in ethyl acetate (8 ml) was added 4N HCl in ethyl acetate (4.17 ml) under stirring at 0° C. After stirring at ambient temperature for 2 hours, and evaporated in vacuo and freeze-dried to give N-[(R)-1-{3-(4-piperidyl)propionyl}-3-piperidylcarbonyl]-β-alanine ethyl ester hydrochloride (0.59 g).

IR (Film): 3320, 1700, 1605 cm⁻¹

NMR (DMSO-$d_6$, δ): 1.18 (3H, t, J=7.1 Hz), 1.26–1.65 (7H, m), 1.80 (2H, d, J=13 Hz), 2.06–2.70 (5H, m), 2.75–3.10 (3H, m), 3.17–3.30 (4H, m), 3.70–3.84 (1H, m), 4.05 (2H, q, J=7.2 Hz), 4.17–4.38 (4H, m), 8.01–8.13 (1H, m), 8.63–8.78 (1H, br), 8.95–9.06 (1H, br)

Mass (m/z): 368 (M⁺+1) free of compound

The following compounds were obtained according to a similar manner to that of Example 25 (1).

(2) (3R)-N-[(R)-1-{3-(4-Piperidyl)propionyl}-3-piperidylcarbonyl]-3-methyl-β-alanine methyl ester hydrochloride IR (Nujol): 3300, 2930, 2850, 1710, 1640, 1610 cm⁻¹

NMR (DMSO-$d_6$, δ): 1.04–1.10 (3H, m), 1.20–1.83 (12H, m), 2.29–2.46 (4H, m), 2.58–3.25 (7H, m), 3.58 (3H, s), 4.02–4.36 (2H, m), 7.91 (1H, t, J=8.2 Hz), 8.57–8.72 (1H, br), 8.84–9.00 (1H, m)

Elemental Analysis $C_{19}H_{23}N_3O_4 \cdot HCl \cdot 2.8H_2O$ (%) Calcd.: C, 50.23; H, 8.79; N, 9.25. Found: C, 50.36; H, 8.51; N, 8.97.

Mass: (m/z): 368 (M⁺+1) free of compound (3) N-[(R)-1-{3-(4-piperidyl)propionyl}-3-piperidylcarbonyl]-β-alanine benzyl ester hydrochloride IR (Film): 3400, 1710, 1630 cm⁻¹

NMR (DMSO-$d_6$, δ): 1.17–1.91 (12H, m), 2.29–2.36 (3H, m), 2.56–3.09 (4H, m), 3.17–3.33 (5H, m), 3.70–3.83 (1H, m), 4.20–4.37 (1H, m), 5.09 (2H, s), 7.31–7.38 (5H, m), 7.99–8.14 (1H, m), 8.60–8.72 (1H, br), 8.89–8.99 (1H, br)

Mass (m/z): 430 (M⁺+1) free of compound

Elemental Analysis $C_{24}H_{35}N_3O_4 \cdot HCl \cdot 1.6H_2O$ Calcd.: C, 54.26; H, 7.63; N, 7.91. Found: C, 54.23; H, 7.54; N, 7.88.

(4) N-[(R)-1-{3-(4-piperidyl)propionyl}-3-piperidylcarbonyl]-β-alanine 1-(cyclohexyloxycarbonyloxy)ethyl ester hydrochloride IR (Film): 3380, 2940, 2850, 1740, 1630 cm⁻¹

NMR (DMSO-$d_6$, δ): 1.15–1.53 (13H, m), 1.44 (3H, d, J=5.4 Hz), 1.60–1.92 (10H, m), 2.05–2.39 (3H, m), 2.46–3.08 (5H, m), 3.18–3.30 (4H, m), 4.15–4.37 (1H, m), 4.50–4.60 (1H, m), 6.60–6.68 (1H, m), 8.00–8.13 (1H, m), 8.47–8.64 (1H, br), 8.79–8.90 (1H, br)

Mass (m/z): 510 (M⁺+1) free of compound

Elemental Analysis $C_{26}H_{43}N_3O_7 \cdot HCl \cdot 3H_2O$ Calcd.: C, 52.04; H, 8.40; N, 7.00. Found: C, 51.85; H, 8.51; N, 7.14.

(5) (R)-[-1-{3-(4-piperidyl)propionyl}-3-piperidylcarbonyl]-3-piperidinecarboxylic acid ethyl ester trifluoro acetate NMR (DMSO-$d_6$, δ): 1.18 (3H, t, J=7.0 Hz), 1.27–2.02 (16H, m), 2.23–2.43 (3H, m), 2.57–3.15 (7H, m), 3.67–3.91 (2H, m), 4.07 (2H, q, J=7.0 Hz), 4.20–4.40 (1H, m), 4.54–4.75 (2H, m), 8.09–8.34 (1H, br), 8.51–8.65 (1H, br)

Mass (m/z): 408 (M⁺+1) free of compound (6) N-[(R)-1-{3-(4-piperidyl)propionyl}-3-piperidylcarbonyl]-2-phenyl-β-alanine ethyl ester hydrochloride IR (KBr, pellet): 3421, 2943, 1728, 1643, 1624 cm⁻¹

NMR (DMSO-$d_6$, δ): 1.05–1.85 (14H, m), 2.04–2.34 (3H, m), 2.69–3.06 (3H, m), 3.13–3.25 (2H, m), 3.32–3.75 (3H, m), 3.80–3.92 (1H, m), 3.99–4.34 (4H, m), 7.20–7.38 (5H, m), 8.07–8.20 (1H, m), 8.75–8.90 (1H, br), 9.04–9–15 (1H, br)

Mass (m/z): 444 (M⁺+1) free of compound (7) N-[(R)-1-{3-(4-piperidyl)propionyl}-3-piperidylcarbonyl]-3(S)-ethynyl-β-alanine 2-adamantyl ester hydrochloride IR (Nujol) 1720, 1650, 1600 cm⁻¹

NMR (DMSO-$d_6$, δ) 1.18–1.60 (8H, m), 1.70–1.99 (15H, m), 2.10–2.39 (3H, m), 2.59–3.02 (5H, m), 3.09–3.29 (3H, m), 3.69–3.84 (1H, m), 4.15–4.55 (4H, m), 4.83–4.95 (2H, m), 8.50 and 8.60 (total 1H, d, J=8.1 and 8.2 Hz), 8.72–8.89 (1H, br), 9.03–9.12 (1H, br)

Mass (m/z): 498 (M⁺+1) free of compound

Elemental Analysis $C_{29}H_{43}N_3O_4 \cdot HCl \cdot 28H_2O$ Calcd.: C, 59.58; H, 8.55; N, 7.19. Found: C, 59.57; H, 8.64; N, 7.03.

(8) N-[(R)-1-{3-(4-piperidyl)propionyl}-3-piperidylcarbonyl]-3(S)-ethynyl-β-alanine-n-butyl ester hydrochloride IR (KBr, pellet): 2958, 2872, 1734, 1647, 1616 cm⁻¹

NMR (DMSO-$d_6$, δ): 0.88 (3H, t, J=7.2 Hz), 1.27–1.69 (12H, m), 1.59 (1H, d, J=2.4 Hz), 1.75–1.86 (3H, m), 2.08–2.40 (3H, m), 2.60–3.08 (6H, m), 3.17–3.27 (3H, m), 3.69–3.84 (1H, m), 4.03 (2H, t, J=6.5 Hz), 4.79–4.92 (1H, m), 8.50 and 8.59 (total (1H, d, J=8.3 and 8.0 Hz), 8.74–8.86 (1H, br), 9.02–9.13 (1H, br)

Elemental Analysis $C_{23}H_{37}N_3O_4 \cdot HCl \cdot 1.6H_2O$ Calcd.: C, 56.98; H, 8.56; N, 8.67. Found: C, 56.99; H, 8.63; N, 8.39.

(9) N-[(R)-1-{3-(4-piperidyl)propionyl}-3-piperidylcarbonyl]-3(S)-ethynyl-β-alanine 5-methyl-2-oxo-1,3-dioxol-4-yl-methyl ester hydrochloride mp: 70° C.

IR (KBr, pellet): 2947, 2866, 2729, 1817, 1743, 1653, 1616 cm⁻¹

NMR (DMSO-$d_6$, δ): 1.29–1.85 (11H, m), 2.09–2.40 (3H, m), 2.10 (3H, s), 2.60–3.09 (5H, m), 3.13–3.29 (3H, m), 3.70–3.84 (1H, m), 4.79–4.91 (1H, m), 4.98 (2H, s), 5.12–5.40 (2H, m), 8.53 and 8.62 (total 1H, d, J=8.0 Hz), 8.76–8.90 (1H, br), 9.03–9.15 (1H, br)

Mass (m/z): 476 (M⁺+1) free of compound

(10) N-[(R)-1-{3-(4-piperidyl)propionyl}-3piperidylcarbonyl]-3(S)-ethynyl-β-alanine isobutyl ester hydrochloride IR (KBr, pellet): 3446, 3230, 3030, 2960, 2873, 1734, 1653, 1616 cm⁻¹

NMR (DMSO-$d_6$, δ): 0.89 (6H, d, J=6.6 Hz), 1.21–1.91 (12H, m), 1.99–2.37 (3H, m), 2.60–3.02 (6H, m), 3.18–3.26 (3H, m), 3.83 (2H, d, J=6.5 Hz), 4.13–4.32 (2H, m), 4.80–4.94 (1H, m), 8.46–8.57 (1H, m), 8.53–8.71 (1H, br), 8.89–9.00 (1H, br)

Mass (m/z): 420 (M⁺+1) free of compound

(11) N-[(R)-1-{3-(4-piperidyl)propionyl}-piperidylcarbonyl]-3(S)-ethynyl-β-alanine-4-trifluoromethylbenzyl ester hydrochloride IR (KBr, pellet): 3456, 3240, 2947, 2864, 2360, 1740, 1653, 1618 cm⁻¹

NMR (DMSO-d⁶, δ): 1.17–1.86 (12H, m), 2.06–2.36 (3H, m), 2.60–3.06 (6H, m), 3.12–3.31 (3H, m), 4.07–4.35 (1H, m), 4.85–4.96 (1H, m), 5.22 (2H, s), 7.60 (2H, d, J=8.2 Hz), 7.76 (2H, d, J=8.2 Hz), 8.48–8.58 (1H, m), 8.44–8.58 (1H, br), 8.74–8.85 (1H, br)

Mass (m/z): 522 (M⁺+1) free of compound

(12) N-[(R)-1-{3-(4-piperidyl)propionyl}-3-piperidylcarbonyl]-2(S)-acetylamino-β-alanine ethyl ester hydrochloride IR (KBr, pellet): 2947, 2862, 1718, 1697, 1684, 1668 cm⁻¹

NMR (DMSO-d₆, δ): 1.17 (3H, t, J=7.1 Hz), 1.24–1.69 (9H, m), 1.74–1.99 (4H, m), 2.07–2.40 (4H, m), 2.59–3.11 (4H, m), 3.15–3.28 (2H, m), 3.31–3.37 (2H, m), 3.73–3.86 (1H, m), 4.02 (2H, q, J=7.1 Hz), 4.15–4.31 (2H, m), 8.12–8.43 (2H, m), 8.63–8.75 (1H, br), 8.93–9.04 (1H, br)

Mass (m/z): 425 (M⁺+1) free of compound

(13) N-[(R)-1-{3-(4-piperidyl)propionyl}-3-piperidylcarbonyl]-2(S)-acetylamino-β-alanine benzyl ester hydrochloride IR (KBr): 3377, 2943, 2864, 2731, 1740, 1653, 1608 cm⁻¹

(14) N-[(R)-1-{3-(4-piperidyl)propionyl}-3-piperidylcarbonyl]-2(S)-acetylamino-β-alanine 1-(cyclohexyloxycarbonyloxy)ethyl ester hydrochloride IR (KBr): 3417, 3062, 2945, 2862, 1761, 1653, 1608 cm⁻¹

EXAMPLE 26

(1) To a solution of N-[2-[1-{3-(1-tert-butoxycarbonyl-4-piperidyl)propionyl}-4-piperidyl]acetyl]-β-alanine methyl ester (0.58 g) in methanol (7 ml) was added 1N NaOH aqueous solution (1.5 ml) and stirred for 1 hour at ambient temperature. The resultant mixture was poured into a mixture of ethyl acetate (20 ml) and water (10 ml) and acidified to pH 3.0 with 10% KHSO₄ aqueous solution. The organic layer was separated and washed with brine, and dried over MgSO₄. The solution was evaporated in vacuo. The residue was dissolved with ethyl acetate (5 ml) and the solution of 4N HCl in ethyl acetate (3.1 ml) was added. The resultant mixture was stirred for 1 hour at ambient temperature and evaporated in vacuo to give N-[2-[1-{3-(4-piperidyl)propionyl}-4-piperidyl]acetyl]-β-alanine hydrochloride (0.2 g).

NMR (DMSO-d₆, δ): 0.95–1.14 (1H, m), 1.21–1.62 (7H, m), 1.76–1.83 (2H, m), 2.26–2.40 (4H, m), 2.75–3.00 (3H, m), 3.17–3.24 (5H, m), 3.78–3.84 (2H, m), 4.05–4.08 (1H, m), 4.28–4.35 (2H, m), 7.93–7.97 (1H, m), 8.70 (1H, br), 8.95 (1H, br)

The following compounds were obtained according to a similar manner to that of Example 26 (1).

(2) N-[1-{3-(4-Piperidyl)propionyl}-3-piperidylcarbonyl]-N-methyl-β-alanine hydrochloride NMR (DMSO-d₆, δ): 1.39–1.45 (7H, m), 1.59–1.83 (5H, m), 2.36–2.60 (4H, m), 2.69–2.88 (2H, m), 2.77, 3.02 (total 3H, s), 3.00–3.23 (3H, m), 3.40–3.80 (3H, m), 4.30–4.40 (1H, m), 8.76 (1H, br), 9.00 (1H, br)

Mass (m/z): 354 (M⁺+1) (3) N-[(R)-1-{3-(4-piperidyl)propionyl}-3-piperidylcarbonyl]-3(S)-[2-(3-indolyl)ethyl]-β-alanine hydrochloride IR (Nujol) 3200, 1720, 1630, 1610, 1540 cm⁻¹

NMR (DMSO-d₆, δ): 1.14 (1H, t, J=7.0 Hz), 1.21–1.45 (5H, m), 1.65–1.91 (6H, m), 2.10–2.42 (3h, m), 2.60–3.00 (6H, m), 3.19–3–25 (3H, m), 3.78–4.33 (7H, m), 6.91–7.08 (3H, m), 7.32 (1H, d, J=8.0 Hz), 7.47 (1H, d, J=8.0 Hz), 7.90–7.96 (1H, m), 8.58 (1H, br), 8.84 (1H, br)

Mass (m/z): 483 (M⁺+1) free of compound

Elemental Analysis C₂₇H₃₈N₄O₄.HCl.2H₂O Calcd.: C, 57.89; H, 7.99; N, 8.71. Found: C, 57.97; H, 8.16; N, 8.31.

(4) N-[(R)-1-{3-(4-piperidyl)propionyl}-3-piperidylcarbonyl]-3(S)-vinyl-β-alanine hydrochloride IR (KBr): 3428, 2946, 1724, 1629, 1621 cm⁻¹

NMR (DMSO-d₆, δ): 1.17–1.99 (11H, m), 2.32–2.60 (5H, m), 2.75–3.00 (2H, m), 3.19–3.24 (2H, m), 3.82–4.38 (4h, m), 4.54–4.62 (1H, m), 5.05–5.12 (2H, m), 5.74–5.92 (1H, m), 8.00–8.06 (1H, m)

Mass (m/z): 366 (M⁺+1) free of compound (5) N-[(R)-1-{3-(4-piperidyl)propionyl}-3-piperidylcarbonyl]-3(S)-ethyl-β-alanine hydrochloride IR (KBr): 3407, 3257, 1724, 1637 cm⁻¹

NMR (DMSO-d₆, δ) 0.76–0.83 (3H, t, J=6.3 Hz), 1.21–1.91 (14H, m), 2.18–2.40 (5H, m), 2.59–3.23 (5H, m), 3.76–4.35 (3H, m), 7.7–7.83 (1H, m)

Mass (m/z): 368 (M⁺+1) free of compound (6) N-[(R)-1-{3-(4-piperidyl)propionyl}-3-piperidylcarbonyl]-2(S)-acetylamino-β-alanine hydrochloride $[\alpha]_D^{25}$=−21.37° (C=0.75, MeOH)

IR (Nujol): 1720, 1640, 1610 cm⁻¹

NMR (DMSO-d₆, δ): 1.20–1.82 (12H, m), 1.85 (3H, s), 2.10–2.43 (5H, m), 2.59–3.27 (4h, m), 3.74–3.83 (2H, m), 4.14–4.37 (2H, m), 8.02–8.19 (2H, m), 8.42–8.59 (1H, br), 8.72–8.84 (1H, br)

Mass (m/z): 397 (M⁺+1) free of compound (7) N-[1-{3-(4-piperidyl)propionyl}-3-pyrrolidinylcarbonyl]-3(S)-ethynyl-β-alanine hydrochloride NMR (DMSO-d₆, δ): 1.21–1.30 (4H, m), 1.76–1.83 (2H, m), 2.00–2.12 (2H, m), 2.23–2.50 (2H, m), 2.57–2.61 (2H, m), 2.76–3.06 (4H, m), 3.18–3.25 (4H, m), 3.50–3.60 (6H, m), 4.81–4.85 (1H, m)

Mass (m/z): 350 (M⁺+1) free of compound (8) N-[(R)-1-{3-(4-piperidyl)propionyl}-3-piperidylcarbonyl]-2-methyl-β-alanine NMR (D₂O, δ): 1.05 (3H, d, J=7.2 Hz), 1.33–1.76 (8H, m), 1.90–1.98 (3H, m), 2.32–2.57 (4H, m), 2.76–3.01 (3H, m), 3.11–3.42 (5H, m), 3.79–3.90 (1H, m), 4.12–4.30 (1H, m)

Mass (m/z): 354 (M⁺+1)

EXAMPLE 27

N-[(R)-1-{3-(4-Piperidyl)propionyl}-3-piperidylcarbonyl]-3(S)ethynyl-β-alanine trifluoroacetate (object compound (I) of Example 25) (80.0 g) was dissolved in water and desalted by DIAION HP-20 (trademark; prepared by Mitsubishi Chemical Industries) eluting with (isopropanol:H₂O=1:3). The eluting solution was concentrated in vacuo and freeze-dried to give N-[(R)-1-{3-(4-piperidyl)propionyl}-3-piperidylcarbonyl]-3(S)-ethynyl-β-alanine (49.8 g) as a white solid.

IR (KBr): 3430, 3270, 1722, 1622 cm⁻¹

NMR (DMSO-d₆, δ): 1.23–2.06 (11H, m), 2.30–2.35 (4H, m), 2.52–2.70 (4H, m), 2.98–3.17 (4H, m), 3.01 (1H, d, J=2.2 Hz), 3.53–3.59 (1H, m), 4.21–4.27 (1H, m), 4.68–4.72 (1H, m), 8.28–8.40 (1H, m)

Mass (m/z): 364 (M⁺+1)

Elemental Analysis C₁₉H₂₉N₃O₄.1.7H₂O (%) Calcd.: C, 57.91; H, 8.29; N, 10.66. Found: C, 57.89; H, 8.05; N, 10.41.

EXAMPLE 28

A solution of N-[(R)-1-{3-(4-piperidyl)propionyl}-3 piperidylcarbonyl]-3(S)-ethynyl-β-alanine hydrochloride (89.6 g) in water (900 ml) was purified by HPLC (C-18, 7×50 cm) eluting with a solution of 17% CH₃CN in 0.1% TFA aqueous solution and the fractions containing object compound were combined and evaporated in vacuo. The residue was dissolved in water and desalted by HP-20 eluting with (IPA:water=1:3). The eluting solution was concentrated in vacuo and freeze-dried to give N-[(R)-1-{3-(4-piperidyl)propionyl}-3-piperidylcarbonyl]-3(S)-ethynyl-β-alanine (55.8 g) as a white solid.

IR (KBr): 3430, 3270, 1722, 1622 cm$^{-1}$

NMR (DMSO-d$_6$, δ): 1.23–2.06 (11H, m), 2.30–2.35 (4H, m), 2.52–2.70 (4H, m), 2.98–3.17 (4H, m), 3.01 (1H, d, J=2.2Hz), 3.53–3.59 (1H, m), 4.21–4.27 (1H, m), 4.68–4.72 (1H, m), 8.28–8.40 (1H, m)

Elemental Analysis C$_{19}$H$_{29}$N$_3$O$_4$·1.7H$_2$O Calcd.: C, 57.91; H, 8.29; N, 10.66. Found: C, 57.89; H, 8.05; N, 10.41.

EXAMPLE 29

A solution of N-[(R)-1-{3-(4-piperidyl)propionyl}-3-piperidylcarbonyl]-3-phenyl-β-alanine hydrochloride in water (30 ml) was purified by HPLC on C18 silica gel eluting with 10.1% TFA aqueous solution:CH$_3$CN=44:11) to give N-[(1R)-1-{3-(4-piperidyl)propionyl}-3-piperidylcarbonyl]-3(S)-phenyl-β-alanine trifluoroacetate (0.08 g) as an oil.

[α]$_D^{20}$=−39.62° (C=0.45, MeOH)

IR (Film): 2910, 2850, 1710, 1630 cm$^{-1}$

NMR (DMSO-d$_6$, δ): 1.17–1.85 (11H, m), 2.12–2.36 (2+1/2H, m), 2.60–3.28 (7+1/2H, m), 3.71–3.83 (1H, m), 4.12–4.38 (2H, m), 5.18 (1H, q, J=7.8 Hz), 7.20–7.38 (5H, m), 8.18–8.32 (1H, br), 8.42 (1H, d, J=8.3 Hz), 8.54–8.64 (1H, br)

Mass (m/z): 416 (M$^+$+1) free of compound and N-[(R)-1-{3-(4-piperidyl)propionyl}-3-piperidylcarbonyl]-3(R)-phenyl-β-alanine trifluoroacetate (0.08 g) as an oil

[α]$_D^{20}$=−1.20° (C=1.0, MeOH)

IR (Film): 3250, 2960, 1710, 1600 cm$^{-1}$

NMR (DMSO-d$_6$, δ): 1.12–1.85 (11H, m), 2.11–2.36 (3H, m), 2.66 (2H, d, J=7.5 Hz), 2.79–3.11 (3H, m), 3.17–3.29 (2H, m), 3.63–3.84 (1H, m), 4.11–4.33 (2H, m), 5.11–5.23 (1H, m), 7.24–7.34 (5H, m), 8.07–8.23 (1H, br), 8.40 (1H, d, J=8.1 Hz), 8.40–8.53 (1H, br)

Mass (m/z): 416 (M$^+$+1) free of compound

The following compound was obtained according to similar manners to that of Example 13 (1) and Example 21 (1).

EXAMPLE 30

N-[(R)-1-{3-(4-piperidyl)propionyl}-3-piperidylcarbonyl]-2-benzyl-β-alanine hydrochloride IR (KBr, pellet): 3439, 2941, 1724, 1639, 1618 cm$^{-1}$ NMR (DMSO-d$_6$, δ): 1.21–1.86 (11H, m), 2.09–2.40 (3H, m), 2.55–2.89 (6H, m), 2.93–3.25 (5H, m), 3.72–3.86 (1H, m), 4.12–4.41 (1H, m), 7.17–7.31 (5H, m), 8.04–8.20 (1H, m), 8.71–8.86 (1H, br), 9.00–9.14 (1H, br)

Mass (m/z): 430 (M$^+$+1) free of compound

The following compound was obtained according to similar manners to that of Example 13 (1) and Example 21 (1).

EXAMPLE 31

N-[(R)-1-{3-(4-piperidyl)propionyl}-3-piperidylcarbonyl]-3-piperidynecarboxylic acid hydrochloride NMR (DMSO-d$_6$, δ): 1.18–1.99 (17H, m), 2.17–2.40 (3H, m), 2.57–3.11 (5H, m), 3.13–3.25 (2H, m), 3.68–3.91 (2H, m), 4.27–4.40 (2H, m), 8.68–8.86 (1H, br), 8.99–9.11 (1H, br)

Mass (m/z) 380 (M$^+$+1) free of compound

The following compound was obtained according to similar manners to that of Example 13 (1) and Example 21 (11).

EXAMPLE 32

N-[(R)-1-{3-(4-piperidyl)propionyl}-3-piperidylcarbonyl]-2-phenyl-β-alanine hydrochloride IR (KBr, pellet): 3410, 3392, 2947, 1724, 1635, 1616 cm$^{-1}$ NMR (DMSO-d$_6$, δ): 1.21–1.86 (11H, m), 2.04–2.61 (4H, m), 2.69–3.06 (3H, m), 3.16–3.27 (2H, m), 3.31–3.84 (4H, m), 4.11–4.34 (1H, m), 7.24–7.33 (5H, m), 8.01–8.15 (1H, m), 8.73–8.85 (1H, br), 9.00–9.12 (1H, br)

Mass (m/z): 416 (M$^+$+1) free of compound

The following compound was obtained to similar manners to that of Example 13 (1) and Example 21 (1).

EXAMPLE 33

N-[(R)-1-{3-(4-piperidyl)propionyl}-3-piperidylcarbonyl]-N-methyl-β-alanine trifluoroacetate IR (KBr, pellet): 3419, 2951, 2866, 1724, 1680, 1620 cm$^{-1}$ NMR (DMSO-d$_6$, δ): 1.14–1.91 (12H, m), 2.11–2.44 (3H, m), 2.70–3.15 (5H, m), 2.78 (3H, s), 3.20–3.32 (2H, m), 3.40–3.62 (2H, m), 3.73–3.88 (1H, m), 4.26–4.40 (1H, m), 8.14–8.27 (1H, br), 8.47–8.59 (1H, br)

Mass (m/z): 354 (M$^+$+1) free of compound

EXAMPLE 34

To a solution of N-[(R)-1-{3-(1-tert-butoxycarbonyl-4-piperidyl)propionyl}-3-piperidylcarbonyl]-3(S)-hydroxymethyl-β-alanine tert-butyl ester (0.2 g) in dichloromethane (3 ml) was added trifluoroacetic acid (3 ml) at ambient temperature. After stirring for 1 hour, the mixture was evaporated in vacuo. The residue was dissolved in water and freeze-dried to give (S)-4-[(R)-1-{3-(4-piperidyl)propionyl}-3-piperidylcarbonylamino]-1,2,3,4-tetrahydro-2-furanone (0.17 g) as a pale yellow oil.

IR (KBr): 3425, 1776, 1678, 1624, 1549 cm$^{-1}$

NMR (D$_2$O, δ): 1.30–2.22 (11H, m), 2.44–2.62 (4H, m), 2.81–3.10 (4H, m), 3.17–3.44 (3H, m), 3.77–3.92 (1H, m), 4.17–4.34 (2H, m), 4.61–4.82 (2H, m)

Mass (m/z): 352 (M$^+$+1) free of compound

EXAMPLE 35

(1) To a solution of N-[(R)-1-{3-(1-tert-butoxycarbonyl-4-piperidyl)propionyl}-3-piperidylcarbonyl]-3(S)-cyano-β-alanine tert-butyl ester (460.9 mg) in dichloromethane (5 ml) was added trifluoroacetic acid (4.6 ml). After stirring at ambient temperature for 2 hours, the mixture was concentrated in vacuo. The residue was dissolved in water and desalted by HP-20 eluting with (IPA:water=1:1). The eluting solution was concentrated in vacuo and freeze-dried to give N-[(R)-1-{3-(4-piperidyl)propionyl}-3-piperidylcarbonyl]-3(S)-cyano-β-alanine (0.12 g).

[α]$_D^{20}$=−31.63° (C=1.0, MeOH)

IR (Film): 3400, 2950, 2850, 1680, 1620 cm$^{-1}$

NMR (DMSO-d$_6$, δ): 0.96–1.82 (13H, m), 2.33–2.82 (6H, m), 2.90–3.34 (4H, m), 3.71–3.89 (1H, m), 4.21–4.47 (1H, m), 6.89–7.35 (1H, m)

Mass (m/z): 365 (M$^+$+1)

The following compounds were obtained according to a similar manner to that of Example 35 (1).

(2) N-[(R)-1-{3-(4-piperidyl)propionyl}-3-piperidylcarbonyl]-3(S)-(n-butanesulfonylaminomethyl)-β-alanine trifluoroacetate IR (Nujol): 1730 cm$^{-1}$ NMR (DMSO-d$_6$, δ): 0.88 (3H, t, J=7.2 Hz), 1.29–1.43 (14H, m), 1.78–1.84 (3H, m), 2.30–2.38 (3H, m), 2.60–2.64 (2H, m), 2.75–3.10 (8H, m), 3.22–3.28 (2H, m), 3.70–3.80 (1H, m)

Mass (m/z): 489 (M$^+$+1) free of compound (3) 4-[3-(4-piperidyl)propionylamino-1-piperidyl]-4-oxo-2(S)-benzoylamino-butyric acid IR (KBr, pellet): 3061, 2945, 2862, 1716, 1647, 1635 cm$^{-1}$ NMR (DMSO-d$_6$, δ): 1.04–1.83 (8H, m), 2.03–2.46 (2H, m), 2.60–2.78 (2H, m), 3.09–4.80 (13H, m), 4.98–5.23 (1H, m), 7.34–7.54 (3H, m), 7.84–7.94 (2H, m), 8.20–8.89 (1H, m)

Mass (m/z): 489 (M$^+$+1)

EXAMPLE 36

(1) A mixture of N-[(R)-1-{3-(4-piperidyl)propionyl}-3-piperidylcarbonyl]-3(S)-ethynyl-β-alanine trifluoroacetate (0.57 g) and 4.9 HCl in ethanol (30 ml) was stirred at ambient temperature for 2 hours, and the mixture was evaporated in vacuo. The residue was purified by HPLc on C18 silica gel eluting with a solution of 18% CH$_3$CN in 0.1% aqueous TFA solution, and the fractions containing object compound were combined and evaporated in vacuo and freeze-dried to give N-[(R)-1-{3-(4-piperidyl)propionyl}-3-piperidyl]-3(S)-ethynyl-β-alanine ethyl ester trifluoro acetate (0.52 g).

[α]$_D^{20}$=−25.60° (C=1.0, MeOH)

IR (Film): 3280, 2930, 2850, 1760, 2720, 1630 cm$^{-1}$

NMR (DMSO-d$_6$, δ): 1.18 (3H, t, J=7.1 Hz), 1.26–1.84 (10H, m), 2.09–2.19 (3H, m), 2.55–3.28 (9H, m), 2.66 (1H, d, J=7.5 Hz)., 3.68–3.82 (1H, m), 4.08 (2H, q, J=7.1 Hz), 4.13–4.31 (1H, m), 4.79–4.93 (1H, m), 8.10–8.63 (3H, m)

Mass (m/z): 394 (M$^+$+1) free of compound

The following compound was obtained according to a similar manner to that of Example 36 (1).

(2) N-[(R)-1-{3-(4-piperidyl)propionyl}-3-piperidylcarbonyl]-2-benzyl-β-alanine ethyl ester trifluoroacetate IR (KBr, pellet): 2945, 2862, 1726, 1680, 1647, 1624 cm$^{-1}$ NMR (DMSO-d$_6$, δ): 1.06 (3H, t, J=7.1 Hz), 1.15–1.66 (7H, m), 1.75–1.87 (4H, m), 2.07–2.39 (3H, m), 2.71–2.95 (6H, m), 3.09–3.32 (5H, m), 3.68–3.84 (1H, m), 3.96 (2H, q, J=7.1 Hz), 4.10–4.39 (1H, m), 7.14–7.39 (5H, m), 8.01–8.10 (1H, m), 8.16–8.30 (1H, br), 8.48–8.60 (1H, br)

Mass (m/z): 458 (M$^+$+1) free of compound

EXAMPLE 37

(1) To a solution of N-[(R)-1-(1-tert-butoxycarbonyl-4-piperidyl)propionyl}-3-piperidylcarbonyl]-3(S)-ethynyl-β-alanine (0.61 g) in N,N-dimethylformamide (6 ml) was added potassium carbonate (182 mg) under stirring at 0° C. After stirring at 0° C. for 15 minutes, isopropylbromide (0.91 ml) was added to the mixture. After stirring at ambient temperature for 3 days, the mixture was poured into saturated aqueous ammonium chloride, and extracted with ethyl acetate. The extract was washed with water and brine, and dried over MgSO$_4$, and evaporated in vacuo. The residue was purified by column chromatography on silica gel eluting with (CHCl$_3$:MeOH=100:1) to give N-[(R)-1-{3-(1-tert-butoxycarbonyl-4-piperidyl)propionyl}-3-piperidylcarbonyl]-3(S)-ethynyl-β-alanine isobutyl ester (0.63 g) as an oil.

IR (Film): 2920, 1720, 1660, 1620 cm$^{-1}$

NMR (CDCl$_3$, δ): 0.95 (6H, d, J=6.7 Hz), 1.01–1.22 (2H, m), 1.45 (9H, s), 1.40–1.75 (8H, m), 1.92–2.02 (3H, m), 2.27 (1H, d, J=2.2 Hz), 2.32–2.40 (3H, m), 2.61–2.73 (4H, m), 3.20–3.63 (2h, m), 3.90 (2H, d, J=6.4 Hz), 3.83–4.15 and 4.35–4.47 (total 3H, m), 5.05–5.15 (1H, m), 6.64–6.71 and 6.99–7.03 (total 1H, m)

Mass (m/z): 520 (M$^+$+1)

The following compounds were obtained according to a similar manner to that of Example 37 (1).

(2) N-[(R)-1-{3-(1-tert-butoxycarbonyl-4-piperidyl)propionyl}-3-piperidylcarbonyl]-3(S)-ethynyl-β-alanine 5-methyl-2-oxo-1,3-dioxol-4-yl-methyl ester IR (Film): 3000, 2920, 2850, 1810, 1740, 1640, 1610 cm$^{-1}$ NMR (CDCl$_3$, δ): 1.02–1.23 (2H, m), 1.45 (9H, s), 1.53–2.10 (11H, m), 2.19 (3H, s), 2.30–2.36 (4H, m), 2.60–2.81 (3H, m), 2.73 (2H, d, J=5.7 Hz), 3.20–3.61 (2H, m), 3.99–4.15 (2H, m), 4.88 (2H, s), 6.95–7.04 (1H, m)

Mass (m/z): 576 (M$^+$+1)

(3) N-[(R)-1-{3-(1-benzyloxycarbonyl-4-piperidyl)-propionyl}-3-piperidylcarbonyl]-2(S)-benzoylamino-β-alanine 1-(cyclohexyloxycarbonyloxy)ethyl ester IR (Film): 2920, 2950, 1740, 1680, 1650 cm$^{-1}$ NMR (CDCl$_3$, δ) 0.99–2.00 (30H, m), 1.83 (3H, d, J=5.8 Hz), 2.30–2.52 (3H, m), 2.64–2.80 (1H, m), 4.07–4.21 (2H, m), 4.57–4.83 (1H, m), 5.12 (2H, s), 7.35–7.51 (10H, m), 7.80–7.95 (1H, m), 8.03–8.09 (1H, m)

Mass (m/z): 763 (M$^+$+1)

(4) N-[(R)-1-{3-(1-tert-butoxycarbonyl-4-piperidyl)-propionyl}-3-piperidylcarbonyl]-3(S)-ethynyl-β-alanine pivaloyloxymethyl ester NMR (CDCl$_3$, δ): 1.09–1.21 (2H, m), 1.23 (9H, s), 1.45 (9H, s), 1.56–1.70 (5H, m), 1.88–2.05 (5H, m), 2.27–2.36 (4H, m), 2.62–2.77 (4H, m), 3.33–3.53 (2H, m), 4.07–4.18 (3H, m), 5.08–5.13 (1H, m), 5.77 (2H, s), 7.01–7.04 (1H, m)

Mass (m/z): 578 (M$^+$+1)

(5) N-[(R)-1-{3-(1-tert-butoxycarbonyl-4-piperidyl)propionyl}-3-piperidylcarbonyl]-2(S)-acetylamino-β-alanine benzyl ester IR (Film): 2920, 2850, 1730, 1650, 1620 cm$^{-1}$ NMR (CDCl$_3$, δ): 1.03–1.22 (2H, m), 1.45 (9H, s), 1.35–1.77 (7H, m), 1.99 (2H, s), 2.08 (3H, s), 2.19–2.51 (4H, m), 2.59–2.74 (2H, m), 3.21–3.43 (2H, m), 3.47–3.89 (2H, m), 4.03–4.21 (3H, m), 4.64–4.85 (1H, m), 5.00–5.18 (2H, m), 7.06–7.19 (1h, m), 7.32–7.40 (6H, m)

(6) N-[(R)-1-{3-(1-tert-butoxycarbonyl-4-piperidyl)propionyl}-3-piperidylcarbonyl]-2(S)-acetylamino-β-alanine 1-(cyclohexyloxycarbonyl)ethyl ester IR (Film): 2930, 2855, 1740, 1650, 1620 cm$^{-1}$ NMR (CDCl$_3$, δ): 1.00–1.23 (2H, m), 1.28–1.80 (21H, m), 1.45 (9H, s), 1.86–1.98 (3H, m), 2.04 (3H, s), 2.14–2.53 (4H, m), 2.60–2.76 (2H, m), 3.12–3.33 (2H, m), 3.41–3.80 (2H, m), 4.02–4.14 (2H, m), 4.25–4.44 (1H, m), 4.57–4.71 (1H, m), 6.60–6.69 (1H, m), 7.28–7.40 (1H, m)

EXAMPLE 38

(1) To a mixture of N-[(R)-1-{3-(1-tert-butoxycarbonyl-4-piperidyl)propionyl}-3-piperidylcarbonyl]-3(S)ethynyl-β-alanine (0.63 g), 4-(trifluoromethyl)benzyl alcohol (0.23 ml) and N,N-dimethylaminopyridine (18 mg) in dichloromethane (7 ml) was added 1-ethyl-3-(3-dimethylaminopropyl)carbodiimide hydrochloride (0.32 g) under stirring at 0° C. After stirring at ambient temperature for overnight, the solution was evaporated in vacuo. The residue was poured into water and extracted with ethyl acetate. The extract was washed with saturated aqueous NaHCO$_3$ solution, water and brine, and dried over MgSO$_4$, and evaporated in vacuo. The residue was purified by column chromatography on silica gel eluting with (CHCl$_3$:MeOH=100:1) to give N-[(R)-1-{3-(1-tert-butoxycarbonyl-4-piperidyl)propionyl}-3-piperidylcarbonyl]-3(S)-ethynyl-β-alanine 4-trifluoromethylbenzyl ester (0.71 g) as an oil.

IR (Film): 2920, 2850,1730, 1650, 1620 cm$^{-1}$

NMR (CDCl$_3$, δ): 1.01–1.22 (2h, m), 1.45 (9H, s), 1.43–1.72 (7H, m), 1.84–2.12 (2H, m), 2.28 (1H, d, J=2.4 Hz), 2.31–2.39 (3H, m), 2.60–2.90 (2H, m), 2.77 (2H, d, J=5.8 Hz), 3.19–3.42 (2H, m), 3.50–3.64 (1H, m), 3.98–4.16 (3H, m), 5.08–5.24 (1H, m), 5.20 (2H, s), 6.61 and 7.04 (total 1H, d, J=8.4 Hz), 7.49 (2H, d, J=8.1 Hz), 7.63 (2h, d, J=8.2 Hz)

Mass (m/z): 622 (M$^+$+1)

The following compounds were obtained according to a similar manner to that of Example 38 (1).

(2) N-[(R)-1-{3-(1-tert-butoxycarbonyl-4-piperidyl)propionyl}-3-piperidylcarbonyl]-3(S)-ethynyl-β-alanine n-butyl ester IR (Film): 2910, 2850, 1720, 1650, 1620 cm$^{-1}$ NMR (CDCl$_3$, δ): 0.94 (3H, t, J=7.2 Hz), 1.01–1.22 (2H, m), 1.31–1.77 (11H, m), 1.45 (9H, s), 1.86–2.11 (2H, m), 2.28 (1H, d, J=2.3 Hz), 2.32–2.40 (3H, m), 2.60–2.80 (4H, m), 3.20–3.41 (2H, m), 3.52–3.66 and 3.85–4.00 (total 1H, m), 4.12 (2H, t, J=6.6 Hz), 4.05–4.71 (3H, m), 5.05–5.16 (1H, m), 6.67–6.75 and 7.00–7.05 (total 1H, m)

Mass (m/z): 520 (M$^+$+1)

(3) N-[(R)-1-{3-(1-tert-butoxycarbonyl-4-piperidyl)propionyl}-3-piperidylcarbonyl]-3(S)-ethynyl-β-alanine 2-adamantyl ester IR (Nujol): 1720, 1660, 1620 cm$^{-1}$ NMR (CDCl$_3$, δ): 1.01–1.21 (2H, m), 1.45 (9H, s), 1.35–1.63 (7H, m), 1.74–1.93 (9H, m), 2.00–2.05 (4H, m), 2.27–2.39 (4H, m), 2.61–2.81 (5H, m), 3.20–3.40 (2H, m), 3.54–3.66 (1H, m), 3.85–3.98 (1H, m), 4.05–4.16 (2H, m), 4.37–4.50 (1H, m), 4.97–5.03 (1H, m), 5.07–5.17 (1H, m), 6.70–6.78 (1H, m), 6.99–7.08 (1H, m)

Mass (m/z): 598 (M$^+$+1)

EXAMPLE 39

To a solution of N-[(R)-1-{3-(4-piperidyl)propionyl}-3-piperidylcarbonyl]-3(S)-ethynyl-β-alanine ethyl ester hydrochloride (0.47 g) in N,N-dimethylformamide (5 ml) was added potassium carbonate (0.2 g) under stirring at 0° C. After stirring at 0° C. for 15 minutes, a solution of 4-bromomethyl-5-methyl-2-oxo-1,3-dioxole (0.19 g) in N,N-dimethylformamide (1 ml) was added to the mixture. After stirring at ambient temperature for overnight, the mixture was poured into saturated aqueous ammonium chloride, and extracted with ethyl acetate. The extract was washed with water and brine, and dried over MgSO$_4$, and evaporated in vacuo. The residue was purified by column chromatography on silica gel eluting with (CHCl$_3$:MeOH= 100:1) to give N-[(R)-1-[3-{1-(5-methyl-2-oxo-1,3-dioxol-4-yl-methyl)-4-piperidyl}propionyl]-3-piperidylcarbonyl]-3(S)-ethynyl-β-alanine ethyl ester (90 mg) as an oil.

IR (Film): 2930, 1810, 1730, 1700, 1655, 1620 cm$^{-1}$

NMR (CDCl$_3$, δ): 1.11–1.35 (2H, m), 1.28 (3H, t, J=7.0 Hz), 1.45–1.80 (9H, m), 1.90–2.04 (4h, m), 2.23 (2H, s), 2.21–2.42 (5H, m), 2.65–3.00 (5H, m), 3.20–3.34 (1H, m), 3.51–3.66 (1H, m), 4.06–4.61 (1H, m), 4.18 (2H, q, J=7.1 Hz), 5.05–5.15 (1H, m), 6.65–7.03 (1H, m)

Mass (m/z): 504 (M$^+$+1)

The following compounds were obtained according to similar manners to that of Example 37 (1) and Example 21 (1).

EXAMPLE 40

(1) N-[(R)-1-{3-(4-piperidyl)propionyl}-3-piperidylcarbonyl]-3(S)-ethynyl-β-alanine benzyl ester trifluoroacetate IR (KBr): 3380, 3284, 1780, 1737, 1675, 1623 cm$^{-1}$ NMR (DMSO-d$_6$, δ): 1.26–1–83 (11H, m), 2.10–2.31 (3H, m), 2.56–3.01 (6H, m), 3.23–3.27 (3H, m), 3.62–3.78 (1H, m), 4.10–4.32 (1H, m), 4.87–4.90 (1H, m), 5.41 (2H, s), 7.37 (5H, m), 8.22 (1H, br), 8.49 (1H, br)

Mass (m/z): 454 (M$^+$+1) free of compound (2) N-[(R)-1-{3-(4-piperidyl)propionyl}-3-piperidylcarbonyl]-3(S)-ethynyl-β-alanine 1-(cyclohexyloxycarbonyloxy)-1-ethyl ester trifluoroacetate IR (KBr): 3409, 3280, 1760, 1673, 1625 cm$^{-1}$ Mass (m/z): 534 (M$^+$+1) free of compound The following compound was obtained according to similar manners to that of Example 25 (1) and Example 27.

EXAMPLE 41

N-[(R)-1-{3-(4-piperidyl)propionyl}-3-piperidylcarbonyl]-3(S)-ethynyl-β-alanine pivaloyloxymethyl ester NMR (D$_2$O, δ): 1.20 (9H, s), 1.32–1.82 (7H, m), 1.95–2.02 (3H, m), 2.54–2.64 (3H, m), 2.78 (1H, d, J=2.4 Hz), 2.92–3.05 (5H, m), 3.16–3.32 (1H, m), 3.40–3.47 (2H, m), 3.82–3.87 (1H, m), 4.09–4.29 (2H, m), 4.92–5.01 (1H, m), 5.80 (2H, s)

Mass (m/z): 478 (M$^+$+1)

EXAMPLE 42

N-[1-{3-(4-piperidyl)propionyl}-3-piperidyl]-3(S)-benzoylaminosuccinamic acid hydrochloride (245 mg) was dissolved in water and purified by HPLC on C18 silica gel eluting with (0.1% TFA aqueous solution:CH$_3$CN=85:15) to give N-[1-{3-(4-piperidyl)propionyl}-3-piperidyl]-3(S)-benzoylaminosuccinamic acid trifluoroacetate (283 mg).

IR (Film): 2500, 1720, 1610 cm$^{-1}$

NMR (DMSO-d$_6$, δ): 1.12–1.88 (11H, m), 2.12–3.04 (8H, m), 3.15–3.31 (2H, m), 3.43–3.85 and 4.16–4.29 (total 3H, m), 4.69–4–83 (1H, m), 7.44–7.60 (3H, m), 7.82–7.95 (2H, m), 8.04–8.11 (1H, m), 8.13–8.26 (1H, br), 8.42–8.54 (1H, br), 8.65–8.74 (1H, m)

Mass (m/z): 459 (M$^+$+1) free of compound

The following compounds were obtained according to a similar manner to that of Example 38 (1).

EXAMPLE 43

(1) N-[(R)-1-{3-(1-tert-butoxycarbonyl-4-piperidyl)propionyl}-3-piperidylcarbonyl]-3(S)-ethynyl-β-alanine n-pentyl ester IR (Film): 2930, 2860, 1720, 1650, 1620 cm$^{-1}$ NMR (CDCl$_3$, δ): 0.91 (3H, t, J=6.7 Hz), 1.01–1.23 (2H, m), 1.31–1.37 (6H, m), 1.45 (9H, s), 1.52–1.73 (9H, m), 2.28 (1H, d, J=2.3 Hz), 2.33–2.40 (3H, m), 2.60–2.76 (4H, m), 3.19–3.71 (3H, m), 4.04–4.15 (3H, m), 4.11 (2H, t, J=6.6 Hz), 5.05–5.15 (1H, m), 6.67–7.08 (1H, m)

(2) N-[(R)-1-{3-(1-tert-butoxycarbonyl-4-piperidyl)propionyl}-3-piperidylcarbonyl]-3(S)-ethynyl-β-alanine n-hexyl ester IR (Film): 2930, 2860, 1720, 1660, 1640, 1620 cm$^{-1}$ NMR (CDCl$_3$, δ): 0.89 (3H, t, J=6.6 Hz), 1.00–1.22 (2H, m), 1.27–1.40 (7H, m), 1.45 (9H, s), 1.51–1.79 (10H, m), 2.28 (1H, d, J=2.3 Hz), 4.06–4.14 (3H, m), 4.11 (2H, t, J=6.6 Hz), 5.05–5.16 (1h, m), 6.72–7.08 (1H, m)

(3) N-[(R)-1-{3-(1-tert-butoxycarbonyl-4-piperidyl)propionyl}-3-piperidylcarbonyl]-3(S)-ethynyl-β-alanine 4-chlorobenzyl ester IR (Film): 3000, 2980, 2925, 2860, 1730, 1675, 1660, 1620 cm$^{-1}$ NMR (CDCl$_3$, δ): 1.00–1.21 (2H, m), 1.45 (9H, s), 1.39–1.77 (9H, m), 2.27 (1H, d, J=2.3 Hz), 2.31–2.39 (3H, m), 2.60–2.76 (4H, m), 3.20–3.60 (3H, m), 3.93–4.14 (3H, m), 5.05–5.19 (1H, m), 5.11 (2H, s), 6.86–7.07 (1H, m), 7.33 (4H, s)

The following compounds were obtained according to a similar manner to that of Example 25 (1).

EXAMPLE 44

(1) N-[(R)-1-3-(4-piperidyl)propionyl]-3-piperidylcarbonyl]-3(S)ethynyl-β-alanine n-pentyl ester hydrochloride IR (KBr, pellet): 3413, 3041, 2947, 2862, 1734, 1657, 1610 cm$^{-1}$ NMR (DMSO-d$_6$, δ): 0.87 (3H, t, J=6.5 Hz), 1.28–1.88 (17H, m), 2.06–2.38 (3H, m), 2.60–3.19 (8H, m), 3.32–3.80 (2H, m), 4.03 (2H, t, J=6.5 Hz), 4.10–4.32 (1H, m), 4.79–4.92 (1H, m), 8.53 (1H, dd, J=13.3 and 8.1 Hz), 8.51–8.69 (1H, br), 8.85–8.96 (1H, br)

(2) N-[(R)-1-3-(4-piperidyl)propionyl]-3-piperidylcarbonyl]-3(S)-ethynyl-β-alanine n-hexyl ester hydrochloride IR (KBr) 3408, 3035, 2958, 2933, 2858, 1736, 1653, 1616 cm$^{-1}$ (3) N-[(R)-1-{3-(4-piperidyl)propionyl}-3-piperidylcarbonyl]-3(S)-ethynyl-β-alanine 4-chlorobenzyl ester hydrochloride IR (KBr, pellet): 3458, 3034, 2949, 2862, 1736, 1649, 1618 cm$^{-1}$ NMR (DMSO-d$_6$, δ): 1.21–1.84 (11H, m), 2.09–2.36 (3H, m), 2.59–3.10 (7H, m), 3.17–3.31 (3H, m), 4.09–4.34 (1H, m), 4.82–4.94 (1H, m), 5.11 (2H, s), 7.40 (2H, d, J=9.0 Hz), 7.45 (2H, d, J=8.7 Hz), 8.47–8.58 (1H, m), 8.47–8.64 (1H, br), 8.80–8.90 (1H, br)

What we claim is:

1. A compound of the formula:

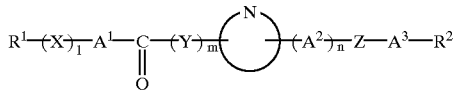

wherein:

R$^1$ is 6-membered cycloalkyl containing 1 to 3 nitrogen atoms which may have one or more amino protective groups;

X is O, S or NH, and l is an integer of either 0 or 1;

A$^1$ is lower alkylene, lower alkenylene or lower alkanylylidene, each of which may have one or more suitable substituent(s);

Y is NH, and m is an integer of either 0 or 1;

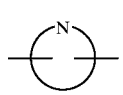

is a group of the formula:

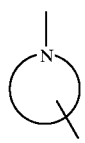

wherein

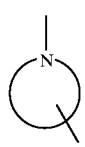

is 5 or 6-membered N-containing heterocyclic group containing 1 to 3 nitrogen atoms which may have one or more suitable substituent(s);

A$^2$ is lower alkylene, and n is an integer of either 0 or 1;

Z is

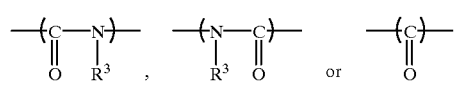

wherein

R$^3$ is hydrogen or lower alkyl;

A$^3$ is lower alkylene which has one or more suitable substituents except carboxy and protected carboxy, with the proviso that when Z is —C(O)NH—, that A$^3$ is not lower alkylene substituted with aryl, aryl(lower) alkyl or an unsaturated heterocyclic group;

and R$^2$ is carboxy or protected carboxy;

or a pharmaceutically acceptable salt thereof.

2. The compound of claim 1, wherein R$^1$ is piperidyl which may have one amino protective group, and

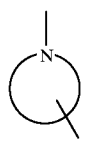

is 5 or 6-membered N-containing heterocyclic group containing 1–3 nitrogens which may have one or more suitable substituent(s), selected from the group consisting of pyrrolyl, pyrrolinyl, imidazolyl, pyrazolyl, pyridyl, dihydropyridyl, pyrimidyl, pyrazinyl, pyridazinyl, triazolyl, pyrrolidinyl, imidazolidinyl, piperidyl, and piperazinyl, each of which may have one or more suitable substituent(s).

3. The compound of claim 2, wherein

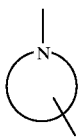

is piperidyl or pyrrolidinyl;

$A^3$ is lower alkylene which has 1 to 3 suitable substituent(s) selected from the group consisting of $(C_1-C_6)$ alkyl; $(C_2-C_6)$ alkenyl; $(C_2-C_6)$ alkynyl; phenyl; phenyl $(C_1-C_6)$ alkyl; phenyl $(C_1-C_6)$ alkyl having 1 to 4 $(C_1-C_6)$ alkoxy, halo $(C_1-C_6)$ alkyl or $(C_1-C_6)$ alkylene dioxy; $(C_1-C_6)$ alkyl having an unsaturated condensed heterocyclic group containing 1 to 4 nitrogen atom(s); cyano; amino; protected amino; and phenyl $(C_1-C_6)$ alkylcarbamoyl;

$R^2$ is carboxy or esterified carboxy, l is an integer of 0, m is an integer of 0, n is an integer of 0.

4. The compound of claim 3, wherein $A^3$ is lower alkylene which has 1 to 3 suitable substituent(s) selected from the group consisting of $(C_1-C_6)$ alkyl; $(C_2-C_6)$ alkenyl; $(C_2-C_6)$ alkynyl; phenyl; phenyl $(C_1-C_6)$ alkyl; phenyl $(C_1-C_6)$ alkyl having 1 to 4 $(C_1-C_6)$ alkoxy, halo $(C_1-C_6)$ alkyl or $(C_1-C_6)$ alkylene dioxy; $(C_1-C_6)$ alkyl having unsaturated condensed heterocyclic group containing 1 to 4 nitrogen atom(s); cyano; amino; $(C_1-C_6)$ alkanoylamino; aroylamino which may have 1 to 3 hydroxy, $(C_1-C_6)$ alkoxy, halogen or phenyl; cyclo $(C_3-C_6)$ alkylcarbonylamino; $(C_1-C_6)$ alkoxy $(C_1-C_6)$ alkylcarbonylamino; $(C_2-C_6)$ alkynylcarbonylamino; $(C_1-C_6)$ alkylsulfonylamino; phenylsulfonylamino; and phenyl $(C_1-C_6)$ alkylcarbamoyl.

5. The compound of claim 3 wherein $R^1$ is piperidyl, $A^1$ is $(C_2-C_6)$ alkylene or $(C_2-C_6)$ alkanylylidene, $A^3$ is lower alkylene which has 1 to 3 suitable substituents selected from the group consisting of $(C_1-C_6)$ alkyl, $(C_2-C_6)$ alkynyl and $(C_1-C_6)$ alkanoylamino,

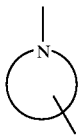

is piperidyl and

Z is

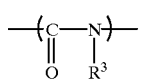

6. The compound of claim 5 wherein $R^3$ is hydrogen, $A^1$ is $(C_2-C_6)$ alkylene, and $A^3$ is lower alkylene having 1 $(C_1-C_6)$ alkanoylamino.

7. The compound of claim 5, wherein $R^3$ is hydrogen, $A^1$ is $(C_2-C_6)$ alkylene, and $A^3$ is lower alkylene having 1 $(C_2-C_6)$ alkynyl.

8. N-[(R)-1-{3-(4-piperidyl)propionyl}-3-piperidylcarbonyl]-2(S)-acetylamino-β-alanine or its hydrochloride.

9. N-[(R)-1-{3-(4-piperidyl)propionyl}-3-piperidylcarbonyl]-3(S)-ethynyl-β-alanine or its hydrochloride.

10. A pharmaceutical composition which comprises a compound of claim 1 or a pharmaceutically acceptable salt thereof in admixture with a pharmaceutically acceptable carrier or excipient.

11. A method for the prevention and/or the treatment of;

a disease caused by thrombus formation;

restenosis or reocclusion, thrombus formation in vascular surgery, valve replacement, extracorporeal circulation or transplantation;

disseminated intravascular coagulation;

thrombotic thrombocytopenia;

essential thrombocytosis;

inflammation;

an immune disease; or metastasis; or for adjuvant therapy with a thrombolytic drug or anticoagulant;

that comprises administering a therapeutically effective amount of the compound of claim 1 or a pharmaceutically acceptable salt thereof to a human being or animal.

12. A process for preparing a compound of claim 1 comprising a method selected from the group consisting of:

(i) reacting a compound of the formula:

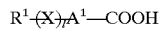

wherein $R^1$, $A^1$, X and l are each as defined in claim 1, or its reactive derivative at the carboxy group or a salt thereof, with a compound of the formula:

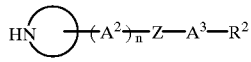

wherein $R^2$, $A^2$, $A^3$,

Z and n are each as defined in claim 1, or its reactive derivative at the amino group or a salt thereof, to give a compound of the formula:

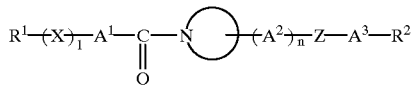

wherein $R^1$, $R^2$, $A^1$, $A^2$, $A^3$,

Z, l and n are each as defined in claim 1, or a salt thereof, (ii) reacting a compound of the formula:

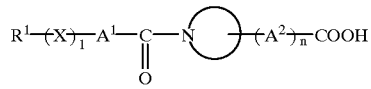

wherein $R^1$, $A^1$, $A^2$,

l and n are each as defined in claim 1, or its reactive derivative at the carboxy group or a salt thereof, with a compound of the formula:

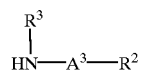

wherein $R^2$, $R^3$ and $A^3$ are each as defined in claim 1, or its reactive derivative at the amino group or a salt thereof, to give a compound of the formula:

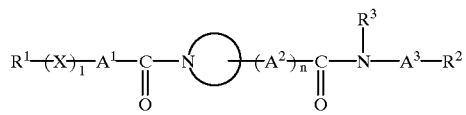

wherein $R^1$, $R^2$, $R^3$, $A^1$, $A^2$, $A^3$,

X, l, and n are each as defined in claim 1, or a salt thereof;

(iii) reacting a compound of the formula:

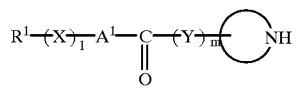

wherein $R^1$, $A^1$,

X, Y, l and m are each as defined in claim 1 or its reactive derivative at the amino group or a salt thereof, with a compound of the formula:

$$R^2-A^3-COOH$$

wherein $R^2$ and $A^3$ are each as defined in claim 1 or its reactive derivative at the carboxy group or a salt thereof, to give a compound of the formula:

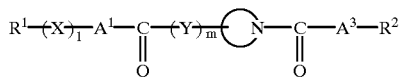

wherein $R^1$, $R^2$, $A^1$, $A^3$,

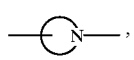

X, Y, l and m are each as defined in claim 1, or a salt thereof;

(iv) subjecting a compound of the formula:

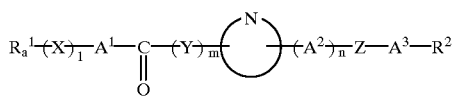

wherein $R^2$, $A^1$, $A^2$, $A^3$,

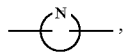

X, Y, Z, l, m and n are each as defined in claim 1 and $R^1_a$ is 6-membered cycloalkyl containing 1–3 nitrogen atoms having an amino protective group, or a salt thereof, to an elimination reaction of the amino protective group, to give a compound of the formula:

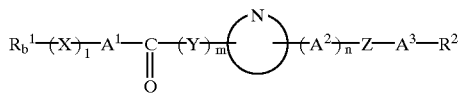

wherein $R^2$, $A^1$, $A^2$, $A^3$,

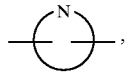

X, Y, Z, l, m and n are each as defined in claim 1, and $R^1_b$ is 6-membered cycloalkyl containing 1–3 nitrogen atoms, or a salt thereof, (v) subjecting a compound of the formula:

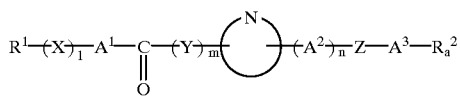

wherein $R^1$, $A^1$, $A^2$,

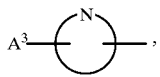

X, Y, Z, l, m and n are each as defined in claim 1, and $R^2_a$ is protected carboxy, or a salt thereof, to elimination reaction of carboxy protective group, to give a compound of the formula:

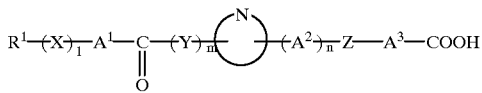

wherein $R^1$, $A^1$, $A^2$,

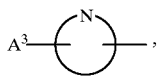

X, Y, Z, l, m and n are each as defined in claim 1, or a salt thereof;

(vi) subjecting a compound of the formula:

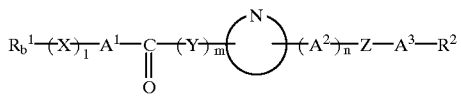

wherein $R^2$, $A^1$, $A^2$,

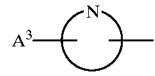

X, Y, Z, l m and n are each as defined in claim 1, and $R^1_b$ is 6-membered cycloalkyl containing 1–3 nitrogen atoms, or a salt thereof, to protecting reaction of amino, to give a compound of the formula:

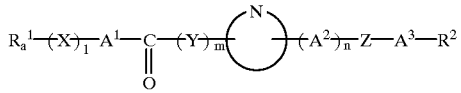

wherein $R^2$, $A^1$, $A^2$,

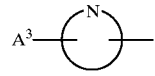

X, Y, Z, l, m and n are each as defined in claim 1, and $R^1_a$ is 6-membered cycloalkyl containing 1 to 3 nitrogens having an amino protective group, or a salt thereof, (vii) subjecting a compound of the formula:

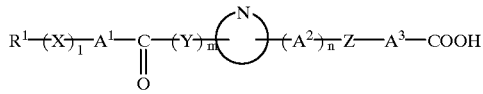

wherein $R^1$, $A^1$, $A^2$,

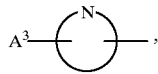

X, Y, Z, l, m and n are each as defined in claim 1, or its reactive derivative at the carboxy group or a salt thereof, to protecting reaction of the carboxy, to give a compound of the formula:

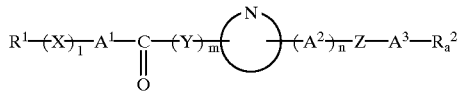

wherein $R^1$, $A^1$, $A^2$,

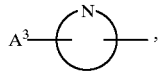

X, Y, Z, l, m and n are each as defined in claim 1, and $R^2_a$ is protected carboxy, or a salt thereof;

(viii) subjecting a compound of the formula:

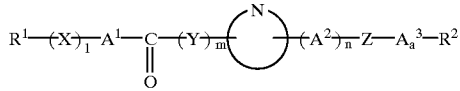

wherein $R^1$, $R^2$, $A^1$, $A^2$,

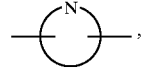

X, Y, Z, l, m and n are each as defined in claim 1, and $A^3_a$ is lower alkylene having protected amino or a salt thereof, to elimination reaction of amino protective group, to give a compound of the formula:

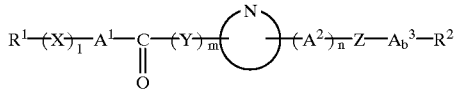

wherein $R^1$, $R^2$, $A^1$, $A^2$,

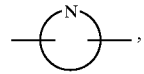

X, Y, Z, l, m and n are each as defined in claim 1, and $A^3_b$ is lower alkylene having amino or a salt thereof, and (ix) subjecting a compound of the formula:
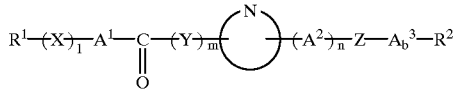
wherein $R^1$, $R^2$, $A^1$, $A^2$,
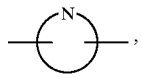
X, Y, Z, l, m and n are each as defined in claim 1, and $A^3_b$ is lower alkylene having amino, or a salt thereof, to acylation reaction of amino, to give a compound of formula:
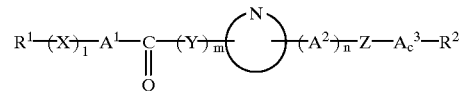
wherein $R^1$, $R^2$, $A^1$, $A^2$,
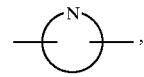
X, Y, Z, l, m and n are each as defined in claim 1, and $A^3_c$ is lower alkylene having acylamino, or a salt thereof.
* * * * *

UNITED STATES PATENT AND TRADEMARK OFFICE
CERTIFICATE OF CORRECTION

PATENT NO. : 6,380,215 B1
DATED : April 30, 2002
INVENTOR(S) : Ohkubo et al.

It is certified that error appears in the above-identified patent and that said Letters Patent is hereby corrected as shown below:

<u>Title page,</u>
Item [86], the PCT information should read:
-- [86]  PCT No.:      PCT/JP94/01550
        § 371 Date:    Aug. 4, 1995
        § 102(e) Date: Aug. 4, 1995 --

Signed and Sealed this

Twenty-fourth Day of September, 2002

*Attest:*

*Attesting Officer*

JAMES E. ROGAN
*Director of the United States Patent and Trademark Office*